(12) United States Patent
Cronin et al.

(10) Patent No.: US 7,444,273 B1
(45) Date of Patent: Oct. 28, 2008

(54) CRYSTALLIZATION OF AURORA/LPL1P-RELATED KINASE

(75) Inventors: Ciaran N. Cronin, San Diego, CA (US); Mark W. Knuth, El Cajon, CA (US); Duncan E. McRee, San Diego, CA (US); Jacek Nowakowski, San Diego, CA (US); Nikola P. Pavletich, New York, NY (US); Devon A. Thompson, San Diego, CA (US); Robert A. Wijnands, Vista, CA (US)

(73) Assignee: Takeda San Diego, Inc., San Diego, CA (US)

( * ) Notice: Subject to any disclaimer, the term of this patent is extended or adjusted under 35 U.S.C. 154(b) by 262 days.

(21) Appl. No.: 10/601,011

(22) Filed: Jun. 20, 2003

Related U.S. Application Data

(60) Provisional application No. 60/390,355, filed on Jun. 21, 2002.

(51) Int. Cl.
G06F 9/455 (2006.01)
G06F 19/00 (2006.01)
C12Q 1/48 (2006.01)
C12N 9/12 (2006.01)
G01N 31/00 (2006.01)

(52) U.S. Cl. .............. 703/11; 702/27; 435/15; 435/194; 436/4

(58) Field of Classification Search .......... None
See application file for complete search history.

(56) References Cited

U.S. PATENT DOCUMENTS 5,962,312 A * 10/1999 Plowman et al. ......... 435/320.1
2004/0137518 A1* 7/2004 Lambert et al. ............. 435/7.1
2005/0143402 A1* 6/2005 Cheetham et al. ...... 514/266.21

FOREIGN PATENT DOCUMENTS

WO 03/031606 * 4/2003

OTHER PUBLICATIONS

"Encyclopedia of Molecular Biology" (Creighton, T., John Wiley and Sons, Inc. New York, 1999, pp. 586 and 2725.*
"Introduction to Protein Structure Second Edition," Branden and Tooze, Garland Publishing Inc., New York, 1999, p. 374-375.*
"Principles of X-ray Crystallography," Drenth, Springer, New York, 1995, p. 1.*
Kierzek et al. (2001) Biophys Chem 91:1-20.*
Wiencek (1999) Ann Rev Biomed Eng 1:505-534.*
Witkowski et al. (1999) Biochemistry 38:11643-11650.*
Sigma Chemical 1993 Catalog, p. 1089.*
Aleshin et al. FEBS Lett 434:42-46, 1998.*
Buts et al. Acta Crystallogr. D., vol. 61, pp. 1149-1159, 2005.*
"Introduction to Protein Structure Second Edition," Branden and Tooze, Garland Publishing Inc., New York, 1999, p. 382.*
Branden et al., "Introduction to Protein Structure Second Edition", Garland Publishing Inc., New York, 1999, p. 382.*
Skarzynski et al., "Industrial perspective on X-ray data collection and analysis", Acta Crystallogr D Biol Crystallogr D62:102-107, 2006.*
Drenth, "Principles of X-Ray Crystallography", Second Edition, Springer, New York, NY, 1999, p. 1.*
McPherson et al. "Current approaches to macromolecular crystallization", Eur. J. Biochem. 189:1-23, 1990.*
Brunger, Axel T. et al., "Crystallography & NMR System: A New Software Suite for Macromolecular Structure Determination", Acta Cryst. (1998) D54, pp. 905-921.
Hegyi, Heidi et al., "The Relationship between Protein Structure and Function: a Comprehensive Survey with Application to the Yeast Genome", J. Mol. Biol. (1999) 288, 147-164.
Vankayalapati, Daruka Mahadevan, et al., "Structure based design of aurora kinase-2 inhibitors: Homology modeling and molecular dynamics docking simulation studies", Proceedings of the American Association for Cancer Research Annual Meeting, Mar. 2002, vol. 43, Abstract #4209, p. 849.

* cited by examiner

Primary Examiner—David J Steadman
(74) Attorney, Agent, or Firm—David J. Weitz

(57) ABSTRACT

Provided are crystals relating to Aurora/LPL1P-related kinase and its various uses.

12 Claims, 49 Drawing Sheets

FIGURE 1

Amino acid sequence for full-length human wild type AIK [SEQ. ID No. 1]

(Residues 125-391 are underlined)

```
MDRSKENCIS GPVKATAPVG GPKRVLVTQQ IPCQNPLPVN SGQAQRVLCP SNSSQRVPLQ   60
AQKLVSSHKP VQNQKQKQLQ ATSVPHPVSR PLNNTQKSKQ PLPSAPENNP EEELASKQKN  120
EESKKRQWAL EDFEIGRPLG KGKFGNVYLA REKQSKFILA LKVLFKAQLE KAGVEHQLRR  180
EVEIQSHLRH PNILRLYGYF HDATRVYLIL EYAPLGTVYR ELQKLSKFDE QRTATYITEL  240
ANALSYCHSK RVIHRDIKPE NLLLGSAGEL KIADFGWSVH APSSRRTTLC GTLDYLPPEM  300
IEGRMHDEKV DLWSLGVLCY EFLVGKPPFE ANTYQETYKR ISRVEFTFPD FVTEGARDLI  360
SRLLKHNPSQ RPMLREVLEH PWITANSSKP SNCQNKESAS KQS                   403
```

Human cDNA sequence encoding residues 125-391 of AIK [SEQ. ID No. 2]

```
AAGAGGCAGT GGGCTTTGGA AGACTTTGAA ATTGGTCGCC CTCTGGGTAA AGGAAAGTTT   60
GGTAATGTTT ATTTGGCAAG AGAAAAGCAA AGCAAGTTTA TTCTGGCTCT TAAAGTGTTA  120
TTTAAAGCTC AGCTGGAGAA AGCCGGAGTG GAGCATCAGC TCAGAAGAGA AGTAGAAATA  180
CAGTCCCACC TTCGGCATCC TAATATTCTT AGACTGTATG GTTATTTCCA TGATGCTACC  240
AGAGTCTACC TAATTCTGGA ATATGCACCA CTTGGAACAG TTTATAGAGA ACTTCAGAAA  300
CTTTCAAAGT TTGATGAGCA GAGAACTGCT ACTTATATAA CAGAATTGGC AAATGCCCTG  360
TCTTACTGTC ATTCGAAGAG AGTTATTCAT AGAGACATTA AGCCAGAGAA CTTACTTCTT  420
GGATCAGCTG GAGAGCTTAA AATTGCAGAT TTTGGGTGGT CAGTACATGC TCCATCTTCC  480
AGGAGGACCA CTCTCTGTGG CACCCTGGAC TACCTGCCCC CTGAAATGAT TGAAGGTCGG  540
ATGCATGATG AGAAGGTGGA TCTCTGGAGC CTTGGAGTTC TTTGCTATGA ATTTTTAGTT  600
GGGAAGCCTC CTTTTGAGGC AAACACATAC CAAGAGACCT ACAAAAGAAT ATCACGGGTT  660
GAATTCACAT TCCCTGACTT TGTAACAGAG GGAGCCAGGG ACCTCATTTC AAGACTGTTG  720
AAGCATAATC CCAGCCAGAG GCCAATGCTC AGAGAAGTAC TTGAACACCC CTGGATCACA  780
GCAAATTCAT CAAAACCATC A                                           801
```

Amino acid sequence for residues 125-391 of AIK with a cleavable (rTev) N-terminal 6x-histidine tag [SEQ. ID No. 3]

(6x-histidine tag and cleavage site are underlined)

```
MSYYHHHHHH DYDIPTTENL YFQGAMGSKR QWALEDFEIG RPLGKGKFGN VYLAREKQSK   60
FILALKVLFK AQLEKAGVEH QLRREVEIQS HLRHPNILRL YGYFHDATRV YLILEYAPLG  120
TVYRELQKLS KFDEQRTATY ITELANALSY CHSKRVIHRD IKPENLLLGS AGELKIADFG  180
WSVHAPSSRR TTLCGTLDYL PPEMIEGRMH DEKVDLWSLG VLCYEFLVGK PPFEANTYQE  240
TYKRISRVEF TFPDFVTEGA RDLISRLLKH NPSQRPMLRE VLEHPWITAN SSKPS       295
```

FIGURE 3

LEGEND

Column headings from left to right are (A)'Atom Number', (B)'Atom Type', (C)'Amino Acid', (D)'Chain Identifier', (E)'Amino Acid Number', (F)'X Coordinate', (G)'Y Coordinate', (H)'Z Coordinate', (I)'Occupancy' (OCC) and (J)'B factor'.

| A | B | C | D | E | F | G | H | I | J |
|---|---|---|---|---|---|---|---|---|---|
| 1 | N | ALA | A | 126 | -1.225 | 18.275 | 58.949 | 1.00 | 62.30 |
| 2 | CA | ALA | A | 126 | -0.160 | 18.687 | 59.906 | 1.00 | 61.70 |
| 3 | CB | ALA | A | 126 | -0.351 | 20.162 | 60.315 | 1.00 | 62.19 |
| 4 | C | ALA | A | 126 | -0.137 | 17.763 | 61.129 | 1.00 | 60.66 |
| 5 | O | ALA | A | 126 | -0.940 | 17.908 | 62.044 | 1.00 | 61.53 |
| 6 | N | ALA | A | 127 | 0.784 | 16.805 | 61.123 | 1.00 | 59.08 |
| 7 | CA | ALA | A | 127 | 0.859 | 15.815 | 62.173 | 1.00 | 57.38 |
| 8 | CB | ALA | A | 127 | 1.255 | 14.482 | 61.599 | 1.00 | 57.77 |
| 9 | C | ALA | A | 127 | 1.878 | 16.247 | 63.205 | 1.00 | 56.23 |
| 10 | O | ALA | A | 127 | 3.075 | 16.075 | 63.000 | 1.00 | 56.65 |
| 11 | N | TRP | A | 128 | 1.401 | 16.816 | 64.301 | 1.00 | 53.28 |
| 12 | CA | TRP | A | 128 | 2.263 | 17.245 | 65.380 | 1.00 | 50.98 |
| 13 | CB | TRP | A | 128 | 1.566 | 18.369 | 66.133 | 1.00 | 51.50 |
| 14 | CG | TRP | A | 128 | 1.402 | 19.546 | 65.268 | 1.00 | 52.38 |
| 15 | CD1 | TRP | A | 128 | 0.246 | 20.024 | 64.714 | 1.00 | 53.18 |
| 16 | NE1 | TRP | A | 128 | 0.515 | 21.153 | 63.973 | 1.00 | 53.05 |
| 17 | CE2 | TRP | A | 128 | 1.862 | 21.394 | 64.017 | 1.00 | 54.15 |
| 18 | CD2 | TRP | A | 128 | 2.442 | 20.405 | 64.834 | 1.00 | 53.19 |
| 19 | CE3 | TRP | A | 128 | 3.820 | 20.440 | 65.049 | 1.00 | 54.16 |
| 20 | CZ3 | TRP | A | 128 | 4.554 | 21.416 | 64.458 | 1.00 | 53.73 |
| 21 | CH2 | TRP | A | 128 | 3.949 | 22.391 | 63.660 | 1.00 | 54.15 |
| 22 | CZ2 | TRP | A | 128 | 2.606 | 22.395 | 63.431 | 1.00 | 54.51 |
| 23 | C | TRP | A | 128 | 2.517 | 16.093 | 66.332 | 1.00 | 49.09 |
| 24 | O | TRP | A | 128 | 1.747 | 15.154 | 66.370 | 1.00 | 48.80 |
| 25 | N | ALA | A | 129 | 3.598 | 16.200 | 67.100 | 1.00 | 47.28 |
| 26 | CA | ALA | A | 129 | 3.992 | 15.236 | 68.114 | 1.00 | 46.51 |
| 27 | CB | ALA | A | 129 | 5.028 | 14.287 | 67.555 | 1.00 | 45.67 |
| 28 | C | ALA | A | 129 | 4.596 | 16.072 | 69.262 | 1.00 | 45.56 |
| 29 | O | ALA | A | 129 | 4.980 | 17.220 | 69.037 | 1.00 | 43.83 |
| 30 | N | LEU | A | 130 | 4.659 | 15.530 | 70.480 | 1.00 | 46.03 |
| 31 | CA | LEU | A | 130 | 5.155 | 16.302 | 71.628 | 1.00 | 46.26 |
| 32 | CB | LEU | A | 130 | 5.119 | 15.469 | 72.909 | 1.00 | 46.46 |
| 33 | CG | LEU | A | 130 | 4.612 | 16.028 | 74.261 | 1.00 | 49.12 |
| 34 | CD1 | LEU | A | 130 | 5.469 | 15.546 | 75.419 | 1.00 | 47.91 |
| 35 | CD2 | LEU | A | 130 | 4.470 | 17.523 | 74.311 | 1.00 | 46.43 |
| 36 | C | LEU | A | 130 | 6.570 | 16.796 | 71.348 | 1.00 | 46.06 |
| 37 | O | LEU | A | 130 | 6.933 | 17.927 | 71.722 | 1.00 | 45.86 |
| 38 | N | GLU | A | 131 | 7.349 | 15.967 | 70.657 | 1.00 | 44.57 |
| 39 | CA | GLU | A | 131 | 8.736 | 16.309 | 70.328 | 1.00 | 43.80 |
| 40 | CB | GLU | A | 131 | 9.506 | 15.118 | 69.669 | 1.00 | 45.34 |
| 41 | CG | GLU | A | 131 | 9.077 | 14.915 | 68.219 | 1.00 | 50.12 |
| 42 | CD | GLU | A | 131 | 9.560 | 13.599 | 67.616 | 1.00 | 59.64 |

FIGURE 3A

| A | B | C | D | E | F | G | H | I | J |
|---|---|---|---|---|---|---|---|---|---|
| 43 | OE1 | GLU | A | 131 | 8.836 | 13.078 | 66.726 | 1.00 | 64.32 |
| 44 | OE2 | GLU | A | 131 | 10.648 | 13.084 | 67.993 | 1.00 | 63.67 |
| 45 | C | GLU | A | 131 | 8.937 | 17.577 | 69.485 | 1.00 | 41.74 |
| 46 | O | GLU | A | 131 | 10.041 | 18.101 | 69.415 | 1.00 | 41.77 |
| 47 | N | ASP | A | 132 | 7.881 | 18.078 | 68.841 | 1.00 | 39.05 |
| 48 | CA | ASP | A | 132 | 8.010 | 19.323 | 68.100 | 1.00 | 38.32 |
| 49 | CB | ASP | A | 132 | 6.935 | 19.466 | 67.028 | 1.00 | 39.96 |
| 50 | CG | ASP | A | 132 | 6.946 | 18.299 | 66.066 | 1.00 | 41.30 |
| 51 | OD1 | ASP | A | 132 | 8.056 | 17.837 | 65.689 | 1.00 | 46.10 |
| 52 | OD2 | ASP | A | 132 | 5.894 | 17.772 | 65.723 | 1.00 | 42.94 |
| 53 | C | ASP | A | 132 | 7.926 | 20.559 | 68.989 | 1.00 | 37.33 |
| 54 | O | ASP | A | 132 | 8.094 | 21.640 | 68.472 | 1.00 | 36.39 |
| 55 | N | PHE | A | 133 | 7.692 | 20.370 | 70.289 | 1.00 | 36.67 |
| 56 | CA | PHE | A | 133 | 7.485 | 21.498 | 71.213 | 1.00 | 37.49 |
| 57 | CB | PHE | A | 133 | 5.998 | 21.569 | 71.740 | 1.00 | 36.30 |
| 58 | CG | PHE | A | 133 | 4.958 | 21.474 | 70.656 | 1.00 | 38.62 |
| 59 | CD1 | PHE | A | 133 | 4.504 | 22.602 | 69.999 | 1.00 | 38.46 |
| 60 | CE1 | PHE | A | 133 | 3.564 | 22.499 | 68.993 | 1.00 | 41.24 |
| 61 | CZ | PHE | A | 133 | 3.108 | 21.250 | 68.611 | 1.00 | 39.81 |
| 62 | CE2 | PHE | A | 133 | 3.564 | 20.125 | 69.246 | 1.00 | 38.63 |
| 63 | CD2 | PHE | A | 133 | 4.495 | 20.235 | 70.252 | 1.00 | 39.61 |
| 64 | C | PHE | A | 133 | 8.475 | 21.593 | 72.399 | 1.00 | 38.04 |
| 65 | O | PHE | A | 133 | 8.934 | 20.578 | 72.922 | 1.00 | 37.77 |
| 66 | N | GLU | A | 134 | 8.825 | 22.817 | 72.801 | 1.00 | 37.74 |
| 67 | CA | GLU | A | 134 | 9.511 | 22.989 | 74.079 | 1.00 | 38.18 |
| 68 | CB | GLU | A | 134 | 10.583 | 24.031 | 73.989 | 1.00 | 38.70 |
| 69 | CG | GLU | A | 134 | 11.692 | 23.627 | 73.052 | 1.00 | 45.76 |
| 70 | CD | GLU | A | 134 | 12.863 | 24.551 | 73.142 | 1.00 | 52.60 |
| 71 | OE1 | GLU | A | 134 | 14.009 | 24.040 | 72.996 | 1.00 | 57.17 |
| 72 | OE2 | GLU | A | 134 | 12.635 | 25.768 | 73.380 | 1.00 | 57.77 |
| 73 | C | GLU | A | 134 | 8.424 | 23.456 | 74.979 | 1.00 | 37.78 |
| 74 | O | GLU | A | 134 | 7.697 | 24.400 | 74.647 | 1.00 | 37.67 |
| 75 | N | ILE | A | 135 | 8.295 | 22.825 | 76.123 | 1.00 | 35.90 |
| 76 | CA | ILE | A | 135 | 7.223 | 23.145 | 76.998 | 1.00 | 37.06 |
| 77 | CB | ILE | A | 135 | 6.657 | 21.878 | 77.499 | 1.00 | 37.79 |
| 78 | CG1 | ILE | A | 135 | 5.960 | 21.157 | 76.334 | 1.00 | 41.64 |
| 79 | CD1 | ILE | A | 135 | 4.794 | 20.341 | 76.792 | 1.00 | 48.55 |
| 80 | CG2 | ILE | A | 135 | 5.700 | 22.126 | 78.593 | 1.00 | 37.59 |
| 81 | C | ILE | A | 135 | 7.682 | 24.058 | 78.152 | 1.00 | 36.78 |
| 82 | O | ILE | A | 135 | 8.778 | 23.906 | 78.672 | 1.00 | 34.54 |
| 83 | N | GLY | A | 136 | 6.819 | 24.998 | 78.533 | 1.00 | 37.69 |
| 84 | CA | GLY | A | 136 | 7.179 | 25.975 | 79.541 | 1.00 | 36.95 |
| 85 | C | GLY | A | 136 | 6.383 | 25.807 | 80.792 | 1.00 | 37.86 |
| 86 | O | GLY | A | 136 | 6.052 | 24.706 | 81.139 | 1.00 | 38.85 |
| 87 | N | ARG | A | 137 | 6.052 | 26.917 | 81.449 | 1.00 | 38.75 |
| 88 | CA | ARG | A | 137 | 5.311 | 26.886 | 82.699 | 1.00 | 39.01 |
| 89 | CB | ARG | A | 137 | 5.392 | 28.252 | 83.369 | 1.00 | 40.79 |
| 90 | CG | ARG | A | 137 | 4.941 | 29.390 | 82.494 | 1.00 | 39.62 |
| 91 | CD | ARG | A | 137 | 4.835 | 30.762 | 83.163 | 1.00 | 45.72 |
| 92 | NE | ARG | A | 137 | 3.554 | 30.754 | 83.754 | 1.00 | 48.61 |

FIGURE 3B

| A | B | C | D | E | F | G | H | I | J |
|---|---|---|---|---|---|---|---|---|---|
| 93 | CZ | ARG | A | 137 | 2.501 | 31.519 | 83.484 | 1.00 | 42.31 |
| 94 | NH1 | ARG | A | 137 | 2.481 | 32.576 | 82.674 | 1.00 | 39.40 |
| 95 | NH2 | ARG | A | 137 | 1.423 | 31.205 | 84.148 | 1.00 | 40.08 |
| 96 | C | ARG | A | 137 | 3.841 | 26.591 | 82.437 | 1.00 | 38.31 |
| 97 | O | ARG | A | 137 | 3.319 | 26.884 | 81.363 | 1.00 | 35.25 |
| 98 | N | PRO | A | 138 | 3.186 | 26.035 | 83.432 | 1.00 | 38.59 |
| 99 | CA | PRO | A | 138 | 1.741 | 25.812 | 83.367 | 1.00 | 37.99 |
| 100 | CB | PRO | A | 138 | 1.416 | 25.119 | 84.688 | 1.00 | 38.79 |
| 101 | CG | PRO | A | 138 | 2.691 | 24.697 | 85.283 | 1.00 | 38.62 |
| 102 | CD | PRO | A | 138 | 3.782 | 25.569 | 84.712 | 1.00 | 40.69 |
| 103 | C | PRO | A | 138 | 1.059 | 27.163 | 83.333 | 1.00 | 37.95 |
| 104 | O | PRO | A | 138 | 1.369 | 28.068 | 84.123 | 1.00 | 36.30 |
| 105 | N | LEU | A | 139 | 0.165 | 27.313 | 82.368 | 1.00 | 37.66 |
| 106 | CA | LEU | A | 139 | -0.617 | 28.512 | 82.249 | 1.00 | 35.85 |
| 107 | CB | LEU | A | 139 | -1.012 | 28.701 | 80.804 | 1.00 | 34.42 |
| 108 | CG | LEU | A | 139 | 0.147 | 29.153 | 79.918 | 1.00 | 35.08 |
| 109 | CD1 | LEU | A | 139 | -0.222 | 29.021 | 78.419 | 1.00 | 33.54 |
| 110 | CD2 | LEU | A | 139 | 0.576 | 30.644 | 80.230 | 1.00 | 35.10 |
| 111 | C | LEU | A | 139 | -1.861 | 28.421 | 83.112 | 1.00 | 36.45 |
| 112 | O | LEU | A | 139 | -2.410 | 29.451 | 83.532 | 1.00 | 35.77 |
| 113 | N | GLY | A | 140 | -2.322 | 27.205 | 83.377 | 1.00 | 36.33 |
| 114 | CA | GLY | A | 140 | -3.533 | 27.031 | 84.172 | 1.00 | 36.31 |
| 115 | C | GLY | A | 140 | -3.900 | 25.579 | 84.428 | 1.00 | 37.85 |
| 116 | O | GLY | A | 140 | -3.285 | 24.651 | 83.886 | 1.00 | 38.33 |
| 117 | N | LYS | A | 141 | -4.872 | 25.372 | 85.301 | 1.00 | 38.89 |
| 118 | CA | LYS | A | 141 | -5.255 | 24.016 | 85.681 | 1.00 | 40.43 |
| 119 | CB | LYS | A | 141 | -5.479 | 23.905 | 87.204 | 1.00 | 41.81 |
| 120 | CG | LYS | A | 141 | -4.305 | 23.314 | 88.006 | 1.00 | 47.61 |
| 121 | CD | LYS | A | 141 | -4.581 | 23.141 | 89.534 | 1.00 | 54.52 |
| 122 | CE | LYS | A | 141 | -4.243 | 24.411 | 90.322 | 1.00 | 58.25 |
| 123 | NZ | LYS | A | 141 | -3.204 | 25.271 | 89.614 | 1.00 | 61.08 |
| 124 | C | LYS | A | 141 | -6.575 | 23.809 | 84.999 | 1.00 | 39.72 |
| 125 | O | LYS | A | 141 | -7.461 | 24.608 | 85.185 | 1.00 | 39.23 |
| 126 | N | GLY | A | 142 | -6.677 | 22.773 | 84.167 | 1.00 | 39.64 |
| 127 | CA | GLY | A | 142 | -7.934 | 22.410 | 83.523 | 1.00 | 40.24 |
| 128 | C | GLY | A | 142 | -8.491 | 21.213 | 84.310 | 1.00 | 41.17 |
| 129 | O | GLY | A | 142 | -7.897 | 20.741 | 85.294 | 1.00 | 41.10 |
| 130 | N | LYS | A | 143 | -9.640 | 20.722 | 83.907 | 1.00 | 41.52 |
| 131 | CA | LYS | A | 143 | -10.245 | 19.612 | 84.630 | 1.00 | 42.27 |
| 132 | CB | LYS | A | 143 | -11.686 | 19.435 | 84.202 | 1.00 | 43.00 |
| 133 | CG | LYS | A | 143 | -12.432 | 18.544 | 85.170 | 1.00 | 48.58 |
| 134 | CD | LYS | A | 143 | -13.719 | 18.034 | 84.570 | 1.00 | 52.87 |
| 135 | CE | LYS | A | 143 | -14.622 | 17.577 | 85.684 | 1.00 | 56.82 |
| 136 | NZ | LYS | A | 143 | -14.896 | 16.117 | 85.592 | 1.00 | 61.41 |
| 137 | C | LYS | A | 143 | -9.471 | 18.292 | 84.453 | 1.00 | 41.56 |
| 138 | O | LYS | A | 143 | -9.248 | 17.572 | 85.412 | 1.00 | 40.75 |
| 139 | N | PHE | A | 144 | -9.014 | 18.045 | 83.228 | 1.00 | 40.56 |
| 140 | CA | PHE | A | 144 | -8.344 | 16.807 | 82.827 | 1.00 | 40.12 |
| 141 | CB | PHE | A | 144 | -9.010 | 16.315 | 81.546 | 1.00 | 40.15 |
| 142 | CG | PHE | A | 144 | -10.461 | 16.037 | 81.725 | 1.00 | 42.78 |
| 143 | CD1 | PHE | A | 144 | -10.877 | 14.867 | 82.383 | 1.00 | 45.37 |

FIGURE 3C

| A | B | C | D | E | F | G | H | I | J |
|---|---|---|---|---|---|---|---|---|---|
| 144 | CE1 | PHE | A | 144 | -12.211 | 14.607 | 82.568 | 1.00 | 42.37 |
| 145 | CZ | PHE | A | 144 | -13.160 | 15.517 | 82.120 | 1.00 | 44.22 |
| 146 | CE2 | PHE | A | 144 | -12.757 | 16.679 | 81.499 | 1.00 | 43.36 |
| 147 | CD2 | PHE | A | 144 | -11.420 | 16.948 | 81.315 | 1.00 | 39.89 |
| 148 | C | PHE | A | 144 | -6.842 | 16.866 | 82.611 | 1.00 | 38.97 |
| 149 | O | PHE | A | 144 | -6.253 | 15.909 | 82.150 | 1.00 | 36.84 |
| 150 | N | GLY | A | 145 | -6.208 | 17.962 | 83.020 | 1.00 | 37.37 |
| 151 | CA | GLY | A | 145 | -4.783 | 18.120 | 82.806 | 1.00 | 38.17 |
| 152 | C | GLY | A | 145 | -4.486 | 19.606 | 82.814 | 1.00 | 37.75 |
| 153 | O | GLY | A | 145 | -5.404 | 20.395 | 82.853 | 1.00 | 38.54 |
| 154 | N | ASN | A | 146 | -3.230 | 19.999 | 82.753 | 1.00 | 38.01 |
| 155 | CA | ASN | A | 146 | -2.930 | 21.412 | 82.804 | 1.00 | 37.94 |
| 156 | CB | ASN | A | 146 | -1.619 | 21.626 | 83.563 | 1.00 | 38.27 |
| 157 | CG | ASN | A | 146 | -1.718 | 21.186 | 85.022 | 1.00 | 43.37 |
| 158 | OD1 | ASN | A | 146 | -2.704 | 21.454 | 85.695 | 1.00 | 49.18 |
| 159 | ND2 | ASN | A | 146 | -0.698 | 20.506 | 85.499 | 1.00 | 48.99 |
| 160 | C | ASN | A | 146 | -2.821 | 21.982 | 81.391 | 1.00 | 36.46 |
| 161 | O | ASN | A | 146 | -2.732 | 21.209 | 80.411 | 1.00 | 35.01 |
| 162 | N | VAL | A | 147 | -2.830 | 23.317 | 81.293 | 1.00 | 34.34 |
| 163 | CA | VAL | A | 147 | -2.512 | 23.965 | 80.024 | 1.00 | 32.03 |
| 164 | CB | VAL | A | 147 | -3.518 | 25.083 | 79.686 | 1.00 | 32.73 |
| 165 | CG1 | VAL | A | 147 | -3.098 | 25.767 | 78.335 | 1.00 | 31.49 |
| 166 | CG2 | VAL | A | 147 | -4.929 | 24.556 | 79.623 | 1.00 | 33.51 |
| 167 | C | VAL | A | 147 | -1.081 | 24.524 | 80.153 | 1.00 | 32.07 |
| 168 | O | VAL | A | 147 | -0.748 | 25.168 | 81.197 | 1.00 | 31.84 |
| 169 | N | TYR | A | 148 | -0.227 | 24.312 | 79.148 | 1.00 | 29.65 |
| 170 | CA | TYR | A | 148 | 1.167 | 24.744 | 79.257 | 1.00 | 30.70 |
| 171 | CB | TYR | A | 148 | 2.135 | 23.546 | 79.082 | 1.00 | 30.68 |
| 172 | CG | TYR | A | 148 | 1.969 | 22.547 | 80.199 | 1.00 | 34.98 |
| 173 | CD1 | TYR | A | 148 | 1.006 | 21.542 | 80.117 | 1.00 | 36.63 |
| 174 | CE1 | TYR | A | 148 | 0.800 | 20.623 | 81.187 | 1.00 | 43.31 |
| 175 | CZ | TYR | A | 148 | 1.568 | 20.721 | 82.344 | 1.00 | 43.61 |
| 176 | OH | TYR | A | 148 | 1.362 | 19.826 | 83.394 | 1.00 | 45.34 |
| 177 | CE2 | TYR | A | 148 | 2.513 | 21.730 | 82.456 | 1.00 | 43.40 |
| 178 | CD2 | TYR | A | 148 | 2.719 | 22.648 | 81.356 | 1.00 | 40.12 |
| 179 | C | TYR | A | 148 | 1.532 | 25.740 | 78.197 | 1.00 | 30.72 |
| 180 | O | TYR | A | 148 | 1.079 | 25.648 | 77.054 | 1.00 | 30.29 |
| 181 | N | LEU | A | 149 | 2.386 | 26.675 | 78.554 | 1.00 | 30.08 |
| 182 | CA | LEU | A | 149 | 3.001 | 27.513 | 77.534 | 1.00 | 30.86 |
| 183 | CB | LEU | A | 149 | 3.880 | 28.526 | 78.247 | 1.00 | 32.09 |
| 184 | CG | LEU | A | 149 | 4.108 | 29.924 | 77.676 | 1.00 | 36.09 |
| 185 | CD1 | LEU | A | 149 | 5.567 | 30.516 | 77.808 | 1.00 | 34.85 |
| 186 | CD2 | LEU | A | 149 | 3.332 | 30.344 | 76.361 | 1.00 | 32.07 |
| 187 | C | LEU | A | 149 | 3.902 | 26.615 | 76.717 | 1.00 | 29.91 |
| 188 | O | LEU | A | 149 | 4.557 | 25.743 | 77.269 | 1.00 | 31.11 |
| 189 | N | ALA | A | 150 | 4.008 | 26.837 | 75.417 | 1.00 | 29.95 |
| 190 | CA | ALA | A | 150 | 4.879 | 25.986 | 74.645 | 1.00 | 29.87 |
| 191 | CB | ALA | A | 150 | 4.091 | 24.697 | 74.127 | 1.00 | 29.08 |
| 192 | C | ALA | A | 150 | 5.435 | 26.770 | 73.456 | 1.00 | 30.54 |
| 193 | O | ALA | A | 150 | 4.860 | 27.774 | 72.966 | 1.00 | 29.82 |
| 194 | N | ARG | A | 151 | 6.558 | 26.299 | 72.990 | 1.00 | 30.55 |

FIGURE 3D

| A | B | C | D | E | F | G | H | I | J |
|---|---|---|---|---|---|---|---|---|---|
| 195 | CA | ARG | A | 151 | 7.164 | 26.847 | 71.809 | 1.00 | 32.81 |
| 196 | CB | ARG | A | 151 | 8.465 | 27.561 | 72.162 | 1.00 | 33.58 |
| 197 | CG | ARG | A | 151 | 8.864 | 28.606 | 71.141 | 1.00 | 34.41 |
| 198 | CD | ARG | A | 151 | 10.216 | 29.272 | 71.493 | 1.00 | 37.68 |
| 199 | NE | ARG | A | 151 | 11.314 | 28.358 | 71.774 | 1.00 | 41.98 |
| 200 | CZ | ARG | A | 151 | 12.579 | 28.754 | 71.840 | 1.00 | 45.91 |
| 201 | NH1 | ARG | A | 151 | 12.855 | 30.033 | 71.642 | 1.00 | 45.17 |
| 202 | NH2 | ARG | A | 151 | 13.554 | 27.891 | 72.109 | 1.00 | 48.67 |
| 203 | C | ARG | A | 151 | 7.393 | 25.735 | 70.792 | 1.00 | 33.58 |
| 204 | O | ARG | A | 151 | 7.806 | 24.623 | 71.151 | 1.00 | 36.75 |
| 205 | N | GLU | A | 152 | 6.998 | 26.037 | 69.557 | 1.00 | 35.31 |
| 206 | CA | GLU | A | 152 | 7.214 | 25.150 | 68.433 | 1.00 | 38.01 |
| 207 | CB | GLU | A | 152 | 6.339 | 25.554 | 67.232 | 1.00 | 38.19 |
| 208 | CG | GLU | A | 152 | 6.245 | 24.450 | 66.177 | 1.00 | 44.01 |
| 209 | CD | GLU | A | 152 | 7.475 | 24.363 | 65.241 | 1.00 | 48.90 |
| 210 | OE1 | GLU | A | 152 | 7.735 | 25.334 | 64.489 | 1.00 | 52.00 |
| 211 | OE2 | GLU | A | 152 | 8.192 | 23.320 | 65.250 | 1.00 | 51.05 |
| 212 | C | GLU | A | 152 | 8.677 | 25.296 | 68.065 | 1.00 | 37.84 |
| 213 | O | GLU | A | 152 | 9.161 | 26.382 | 67.791 | 1.00 | 38.28 |
| 214 | N | LYS | A | 153 | 9.392 | 24.200 | 68.043 | 1.00 | 39.21 |
| 215 | CA | LYS | A | 153 | 10.819 | 24.306 | 67.841 | 1.00 | 42.09 |
| 216 | CB | LYS | A | 153 | 11.481 | 22.967 | 68.153 | 1.00 | 42.63 |
| 217 | CG | LYS | A | 153 | 11.928 | 22.851 | 69.590 | 1.00 | 48.61 |
| 218 | CD | LYS | A | 153 | 11.539 | 21.510 | 70.175 | 1.00 | 55.42 |
| 219 | CE | LYS | A | 153 | 11.720 | 20.374 | 69.179 | 1.00 | 60.62 |
| 220 | NZ | LYS | A | 153 | 13.095 | 19.664 | 69.260 | 1.00 | 68.26 |
| 221 | C | LYS | A | 153 | 11.287 | 24.885 | 66.509 | 1.00 | 42.57 |
| 222 | O | LYS | A | 153 | 12.262 | 25.589 | 66.449 | 1.00 | 43.65 |
| 223 | N | GLN | A | 154 | 10.603 | 24.623 | 65.421 | 1.00 | 43.01 |
| 224 | CA | GLN | A | 154 | 11.158 | 25.126 | 64.163 | 1.00 | 44.19 |
| 225 | CB | GLN | A | 154 | 10.676 | 24.231 | 63.015 | 1.00 | 44.67 |
| 226 | CG | GLN | A | 154 | 11.442 | 22.952 | 63.045 | 1.00 | 53.28 |
| 227 | CD | GLN | A | 154 | 11.408 | 22.213 | 61.740 | 1.00 | 60.70 |
| 228 | OE1 | GLN | A | 154 | 10.328 | 21.982 | 61.174 | 1.00 | 66.15 |
| 229 | NE2 | GLN | A | 154 | 12.586 | 21.838 | 61.246 | 1.00 | 64.53 |
| 230 | C | GLN | A | 154 | 10.856 | 26.600 | 63.884 | 1.00 | 41.49 |
| 231 | O | GLN | A | 154 | 11.660 | 27.356 | 63.358 | 1.00 | 42.67 |
| 232 | N | SER | A | 155 | 9.675 | 27.022 | 64.254 | 1.00 | 38.39 |
| 233 | CA | SER | A | 155 | 9.313 | 28.371 | 63.946 | 1.00 | 35.68 |
| 234 | CB | SER | A | 155 | 7.840 | 28.364 | 63.594 | 1.00 | 34.74 |
| 235 | OG | SER | A | 155 | 7.196 | 27.875 | 64.746 | 1.00 | 34.70 |
| 236 | C | SER | A | 155 | 9.532 | 29.313 | 65.140 | 1.00 | 33.68 |
| 237 | O | SER | A | 155 | 9.505 | 30.517 | 64.946 | 1.00 | 33.85 |
| 238 | N | LYS | A | 156 | 9.672 | 28.739 | 66.331 | 1.00 | 32.82 |
| 239 | CA | LYS | A | 156 | 9.704 | 29.445 | 67.645 | 1.00 | 34.59 |
| 240 | CB | LYS | A | 156 | 10.858 | 30.467 | 67.753 | 1.00 | 34.66 |
| 241 | CG | LYS | A | 156 | 12.319 | 29.876 | 67.480 | 1.00 | 36.79 |
| 242 | CD | LYS | A | 156 | 13.429 | 30.907 | 67.970 | 1.00 | 44.57 |
| 243 | CE | LYS | A | 156 | 14.696 | 31.115 | 67.056 | 1.00 | 47.52 |
| 244 | NZ | LYS | A | 156 | 14.787 | 32.563 | 66.539 | 1.00 | 46.31 |
| 245 | C | LYS | A | 156 | 8.335 | 30.102 | 67.987 | 1.00 | 33.10 |

FIGURE 3E

| A | B | C | D | E | F | G | H | I | J |
|---|---|---|---|---|---|---|---|---|---|
| 246 | O | LYS | A | 156 | 8.218 | 31.065 | 68.804 | 1.00 | 31.56 |
| 247 | N | PHE | A | 157 | 7.302 | 29.553 | 67.386 | 1.00 | 31.13 |
| 248 | CA | PHE | A | 157 | 5.948 | 30.020 | 67.646 | 1.00 | 31.45 |
| 249 | CB | PHE | A | 157 | 5.016 | 29.469 | 66.575 | 1.00 | 32.15 |
| 250 | CG | PHE | A | 157 | 3.713 | 30.177 | 66.469 | 1.00 | 34.87 |
| 251 | CD1 | PHE | A | 157 | 3.527 | 31.155 | 65.492 | 1.00 | 38.48 |
| 252 | CE1 | PHE | A | 157 | 2.274 | 31.786 | 65.329 | 1.00 | 40.08 |
| 253 | CZ | PHE | A | 157 | 1.209 | 31.427 | 66.143 | 1.00 | 37.15 |
| 254 | CE2 | PHE | A | 157 | 1.368 | 30.425 | 67.104 | 1.00 | 34.69 |
| 255 | CD2 | PHE | A | 157 | 2.644 | 29.795 | 67.253 | 1.00 | 36.13 |
| 256 | C | PHE | A | 157 | 5.466 | 29.641 | 69.057 | 1.00 | 29.29 |
| 257 | O | PHE | A | 157 | 5.395 | 28.469 | 69.412 | 1.00 | 29.48 |
| 258 | N | ILE | A | 158 | 5.022 | 30.656 | 69.813 | 1.00 | 29.61 |
| 259 | CA | ILE | A | 158 | 4.651 | 30.447 | 71.207 | 1.00 | 30.50 |
| 260 | CB | ILE | A | 158 | 4.899 | 31.717 | 72.032 | 1.00 | 31.00 |
| 261 | CG1 | ILE | A | 158 | 6.366 | 31.797 | 72.339 | 1.00 | 36.27 |
| 262 | CD1 | ILE | A | 158 | 6.687 | 30.925 | 73.512 | 1.00 | 37.94 |
| 263 | CG2 | ILE | A | 158 | 4.419 | 31.510 | 73.466 | 1.00 | 32.23 |
| 264 | C | ILE | A | 158 | 3.209 | 30.163 | 71.230 | 1.00 | 29.07 |
| 265 | O | ILE | A | 158 | 2.473 | 30.911 | 70.644 | 1.00 | 30.88 |
| 266 | N | LEU | A | 159 | 2.745 | 29.157 | 71.935 | 1.00 | 28.37 |
| 267 | CA | LEU | A | 159 | 1.339 | 28.868 | 71.885 | 1.00 | 28.41 |
| 268 | CB | LEU | A | 159 | 1.085 | 27.936 | 70.692 | 1.00 | 28.97 |
| 269 | CG | LEU | A | 159 | 1.953 | 26.777 | 70.259 | 1.00 | 34.00 |
| 270 | CD1 | LEU | A | 159 | 1.782 | 25.602 | 71.203 | 1.00 | 35.94 |
| 271 | CD2 | LEU | A | 159 | 1.737 | 26.341 | 68.787 | 1.00 | 39.02 |
| 272 | C | LEU | A | 159 | 1.079 | 28.193 | 73.204 | 1.00 | 27.83 |
| 273 | O | LEU | A | 159 | 1.957 | 28.166 | 74.034 | 1.00 | 27.51 |
| 274 | N | ALA | A | 160 | -0.120 | 27.685 | 73.409 | 1.00 | 29.15 |
| 275 | CA | ALA | A | 160 | -0.450 | 27.016 | 74.661 | 1.00 | 30.37 |
| 276 | CB | ALA | A | 160 | -1.651 | 27.684 | 75.323 | 1.00 | 28.84 |
| 277 | C | ALA | A | 160 | -0.818 | 25.602 | 74.297 | 1.00 | 32.10 |
| 278 | O | ALA | A | 160 | -1.472 | 25.371 | 73.269 | 1.00 | 31.99 |
| 279 | N | LEU | A | 161 | -0.434 | 24.654 | 75.163 | 1.00 | 33.02 |
| 280 | CA | LEU | A | 161 | -0.741 | 23.261 | 74.941 | 1.00 | 34.14 |
| 281 | CB | LEU | A | 161 | 0.577 | 22.495 | 74.913 | 1.00 | 34.88 |
| 282 | CG | LEU | A | 161 | 0.908 | 21.455 | 73.868 | 1.00 | 39.45 |
| 283 | CD1 | LEU | A | 161 | 0.455 | 21.854 | 72.442 | 1.00 | 35.63 |
| 284 | CD2 | LEU | A | 161 | 2.466 | 21.138 | 73.933 | 1.00 | 40.14 |
| 285 | C | LEU | A | 161 | -1.648 | 22.780 | 76.036 | 1.00 | 33.03 |
| 286 | O | LEU | A | 161 | -1.271 | 22.762 | 77.217 | 1.00 | 33.04 |
| 287 | N | LYS | A | 162 | -2.885 | 22.456 | 75.657 | 1.00 | 31.43 |
| 288 | CA | LYS | A | 162 | -3.856 | 21.979 | 76.610 | 1.00 | 32.34 |
| 289 | CB | LYS | A | 162 | -5.251 | 22.451 | 76.196 | 1.00 | 32.99 |
| 290 | CG | LYS | A | 162 | -6.391 | 21.951 | 77.087 | 1.00 | 29.62 |
| 291 | CD | LYS | A | 162 | -7.595 | 22.831 | 76.855 | 1.00 | 29.33 |
| 292 | CE | LYS | A | 162 | -8.841 | 22.204 | 77.533 | 1.00 | 27.32 |
| 293 | NZ | LYS | A | 162 | -10.098 | 22.987 | 77.412 | 1.00 | 31.96 |
| 294 | C | LYS | A | 162 | -3.772 | 20.441 | 76.654 | 1.00 | 33.11 |
| 295 | O | LYS | A | 162 | -4.017 | 19.775 | 75.666 | 1.00 | 33.31 |
| 296 | N | VAL | A | 163 | -3.364 | 19.907 | 77.790 | 1.00 | 35.02 |

FIGURE 3F

| A | B | C | D | E | F | G | H | I | J |
|---|---|---|---|---|---|---|---|---|---|
| 297 | CA | VAL | A | 163 | -3.205 | 18.471 | 77.983 | 1.00 | 37.14 |
| 298 | CB | VAL | A | 163 | -1.971 | 18.203 | 78.854 | 1.00 | 36.58 |
| 299 | CG1 | VAL | A | 163 | -1.720 | 16.660 | 79.039 | 1.00 | 37.74 |
| 300 | CG2 | VAL | A | 163 | -0.709 | 18.909 | 78.260 | 1.00 | 38.41 |
| 301 | C | VAL | A | 163 | -4.445 | 17.854 | 78.653 | 1.00 | 37.59 |
| 302 | O | VAL | A | 163 | -4.960 | 18.395 | 79.644 | 1.00 | 37.22 |
| 303 | N | LEU | A | 164 | -4.977 | 16.767 | 78.073 | 1.00 | 39.14 |
| 304 | CA | LEU | A | 164 | -6.104 | 16.048 | 78.686 | 1.00 | 39.01 |
| 305 | CB | LEU | A | 164 | -7.427 | 16.202 | 77.930 | 1.00 | 39.22 |
| 306 | CG | LEU | A | 164 | -7.961 | 17.622 | 77.781 | 1.00 | 38.09 |
| 307 | CD1 | LEU | A | 164 | -7.363 | 18.125 | 76.508 | 1.00 | 38.01 |
| 308 | CD2 | LEU | A | 164 | -9.453 | 17.647 | 77.711 | 1.00 | 37.35 |
| 309 | C | LEU | A | 164 | -5.759 | 14.562 | 78.783 | 1.00 | 39.97 |
| 310 | O | LEU | A | 164 | -5.369 | 13.952 | 77.798 | 1.00 | 38.76 |
| 311 | N | PHE | A | 165 | -5.880 | 14.004 | 79.986 | 1.00 | 40.67 |
| 312 | CA | PHE | A | 165 | -5.535 | 12.599 | 80.211 | 1.00 | 42.42 |
| 313 | CB | PHE | A | 165 | -5.191 | 12.355 | 81.686 | 1.00 | 42.83 |
| 314 | CG | PHE | A | 165 | -3.815 | 12.784 | 82.030 | 1.00 | 46.45 |
| 315 | CD1 | PHE | A | 165 | -3.573 | 14.040 | 82.560 | 1.00 | 47.62 |
| 316 | CE1 | PHE | A | 165 | -2.290 | 14.434 | 82.868 | 1.00 | 47.96 |
| 317 | CZ | PHE | A | 165 | -1.227 | 13.574 | 82.628 | 1.00 | 50.56 |
| 318 | CE2 | PHE | A | 165 | -1.446 | 12.349 | 82.067 | 1.00 | 48.72 |
| 319 | CD2 | PHE | A | 165 | -2.740 | 11.951 | 81.775 | 1.00 | 48.08 |
| 320 | C | PHE | A | 165 | -6.665 | 11.709 | 79.743 | 1.00 | 42.46 |
| 321 | O | PHE | A | 165 | -7.788 | 11.832 | 80.199 | 1.00 | 40.57 |
| 322 | N | LYS | A | 166 | -6.360 | 10.867 | 78.768 | 1.00 | 43.35 |
| 323 | CA | LYS | A | 166 | -7.342 | 9.957 | 78.209 | 1.00 | 45.50 |
| 324 | CB | LYS | A | 166 | -6.696 | 9.043 | 77.155 | 1.00 | 46.27 |
| 325 | CG | LYS | A | 166 | -6.559 | 9.666 | 75.786 | 1.00 | 46.27 |
| 326 | CD | LYS | A | 166 | -5.423 | 8.956 | 75.032 | 1.00 | 53.89 |
| 327 | CE | LYS | A | 166 | -5.279 | 9.445 | 73.581 | 1.00 | 55.13 |
| 328 | NZ | LYS | A | 166 | -5.709 | 8.444 | 72.569 | 1.00 | 59.86 |
| 329 | C | LYS | A | 166 | -8.040 | 9.102 | 79.273 | 1.00 | 45.98 |
| 330 | O | LYS | A | 166 | -9.230 | 8.981 | 79.250 | 1.00 | 46.56 |
| 331 | N | ALA | A | 167 | -7.324 | 8.561 | 80.240 | 1.00 | 47.94 |
| 332 | CA | ALA | A | 167 | -8.025 | 7.699 | 81.191 | 1.00 | 49.17 |
| 333 | CB | ALA | A | 167 | -7.091 | 7.201 | 82.220 | 1.00 | 49.16 |
| 334 | C | ALA | A | 167 | -9.168 | 8.457 | 81.848 | 1.00 | 49.92 |
| 335 | O | ALA | A | 167 | -10.305 | 7.957 | 81.995 | 1.00 | 49.78 |
| 336 | N | GLN | A | 168 | -8.859 | 9.696 | 82.218 | 1.00 | 49.84 |
| 337 | CA | GLN | A | 168 | -9.787 | 10.502 | 82.960 | 1.00 | 49.29 |
| 338 | CB | GLN | A | 168 | -9.058 | 11.694 | 83.591 | 1.00 | 50.22 |
| 339 | CG | GLN | A | 168 | -8.451 | 11.419 | 84.993 | 1.00 | 54.78 |
| 340 | CD | GLN | A | 168 | -7.028 | 10.830 | 84.965 | 1.00 | 62.45 |
| 341 | OE1 | GLN | A | 168 | -6.053 | 11.569 | 84.788 | 1.00 | 65.02 |
| 342 | NE2 | GLN | A | 168 | -6.908 | 9.511 | 85.190 | 1.00 | 64.80 |
| 343 | C | GLN | A | 168 | -10.953 | 10.939 | 82.088 | 1.00 | 48.29 |
| 344 | O | GLN | A | 168 | -12.085 | 10.976 | 82.553 | 1.00 | 47.87 |
| 345 | N | LEU | A | 169 | -10.702 | 11.245 | 80.814 | 1.00 | 48.22 |
| 346 | CA | LEU | A | 169 | -11.808 | 11.676 | 79.964 | 1.00 | 48.39 |
| 347 | CB | LEU | A | 169 | -11.322 | 12.112 | 78.575 | 1.00 | 47.89 |

FIGURE 3G

| A | B | C | D | E | F | G | H | I | J |
|---|---|---|---|---|---|---|---|---|---|
| 348 | CG | LEU | A | 169 | -10.644 | 13.461 | 78.330 | 1.00 | 49.67 |
| 349 | CD1 | LEU | A | 169 | -10.181 | 13.552 | 76.882 | 1.00 | 48.91 |
| 350 | CD2 | LEU | A | 169 | -11.615 | 14.580 | 78.615 | 1.00 | 45.84 |
| 351 | C | LEU | A | 169 | -12.819 | 10.538 | 79.785 | 1.00 | 47.86 |
| 352 | O | LEU | A | 169 | -14.027 | 10.733 | 79.875 | 1.00 | 47.83 |
| 353 | N | ALA | A | 170 | -12.316 | 9.368 | 79.451 | 1.00 | 48.31 |
| 354 | CA | ALA | A | 170 | -13.220 | 8.238 | 79.195 | 1.00 | 48.55 |
| 355 | CB | ALA | A | 170 | -12.468 | 7.070 | 78.581 | 1.00 | 49.34 |
| 356 | C | ALA | A | 170 | -13.927 | 7.860 | 80.494 | 1.00 | 48.26 |
| 357 | O | ALA | A | 170 | -15.118 | 7.692 | 80.501 | 1.00 | 49.17 |
| 358 | N | ALA | A | 171 | -13.207 | 7.806 | 81.606 | 1.00 | 48.63 |
| 359 | CA | ALA | A | 171 | -13.857 | 7.578 | 82.885 | 1.00 | 48.78 |
| 360 | CB | ALA | A | 171 | -12.858 | 7.685 | 84.058 | 1.00 | 49.66 |
| 361 | C | ALA | A | 171 | -14.996 | 8.561 | 83.082 | 1.00 | 48.71 |
| 362 | O | ALA | A | 171 | -16.113 | 8.179 | 83.429 | 1.00 | 48.35 |
| 363 | N | ALA | A | 172 | -14.723 | 9.841 | 82.844 | 1.00 | 48.29 |
| 364 | CA | ALA | A | 172 | -15.740 | 10.846 | 83.012 | 1.00 | 47.44 |
| 365 | CB | ALA | A | 172 | -15.093 | 12.246 | 83.064 | 1.00 | 48.07 |
| 366 | C | ALA | A | 172 | -16.759 | 10.737 | 81.888 | 1.00 | 47.98 |
| 367 | O | ALA | A | 172 | -17.893 | 11.232 | 81.984 | 1.00 | 48.40 |
| 368 | N | GLY | A | 173 | -16.371 | 10.067 | 80.815 | 1.00 | 48.12 |
| 369 | CA | GLY | A | 173 | -17.262 | 9.907 | 79.674 | 1.00 | 47.85 |
| 370 | C | GLY | A | 173 | -17.733 | 11.166 | 78.995 | 1.00 | 47.73 |
| 371 | O | GLY | A | 173 | -18.926 | 11.308 | 78.705 | 1.00 | 49.07 |
| 372 | N | VAL | A | 174 | -16.790 | 12.075 | 78.736 | 1.00 | 46.88 |
| 373 | CA | VAL | A | 174 | -17.030 | 13.322 | 78.021 | 1.00 | 45.99 |
| 374 | CB | VAL | A | 174 | -16.674 | 14.572 | 78.873 | 1.00 | 45.74 |
| 375 | CG1 | VAL | A | 174 | -17.722 | 14.810 | 79.913 | 1.00 | 49.76 |
| 376 | CG2 | VAL | A | 174 | -15.330 | 14.425 | 79.472 | 1.00 | 46.00 |
| 377 | C | VAL | A | 174 | -16.132 | 13.394 | 76.798 | 1.00 | 44.25 |
| 378 | O | VAL | A | 174 | -15.792 | 14.483 | 76.300 | 1.00 | 43.32 |
| 379 | N | ALA | A | 175 | -15.708 | 12.236 | 76.322 | 1.00 | 42.33 |
| 380 | CA | ALA | A | 175 | -14.879 | 12.221 | 75.125 | 1.00 | 41.82 |
| 381 | CB | ALA | A | 175 | -14.563 | 10.748 | 74.679 | 1.00 | 41.75 |
| 382 | C | ALA | A | 175 | -15.577 | 13.026 | 74.008 | 1.00 | 40.98 |
| 383 | O | ALA | A | 175 | -14.920 | 13.683 | 73.189 | 1.00 | 42.44 |
| 384 | N | HIS | A | 176 | -16.899 | 13.030 | 74.009 | 1.00 | 40.16 |
| 385 | CA | HIS | A | 176 | -17.657 | 13.751 | 72.980 | 1.00 | 41.39 |
| 386 | CB | HIS | A | 176 | -19.146 | 13.385 | 73.068 | 1.00 | 41.58 |
| 387 | CG | HIS | A | 176 | -19.803 | 13.903 | 74.318 | 1.00 | 45.86 |
| 388 | ND1 | HIS | A | 176 | -19.695 | 13.259 | 75.543 | 1.00 | 47.14 |
| 389 | CE1 | HIS | A | 176 | -20.355 | 13.949 | 76.460 | 1.00 | 47.79 |
| 390 | NE2 | HIS | A | 176 | -20.854 | 15.035 | 75.885 | 1.00 | 49.44 |
| 391 | CD2 | HIS | A | 176 | -20.532 | 15.023 | 74.545 | 1.00 | 46.34 |
| 392 | C | HIS | A | 176 | -17.477 | 15.312 | 73.096 | 1.00 | 40.21 |
| 393 | O | HIS | A | 176 | -17.529 | 16.043 | 72.107 | 1.00 | 38.56 |
| 394 | N | GLN | A | 177 | -17.282 | 15.793 | 74.320 | 1.00 | 39.05 |
| 395 | CA | GLN | A | 177 | -17.021 | 17.231 | 74.544 | 1.00 | 39.77 |
| 396 | CB | GLN | A | 177 | -17.008 | 17.567 | 76.019 | 1.00 | 38.88 |
| 397 | CG | GLN | A | 177 | -18.343 | 17.312 | 76.675 | 1.00 | 38.17 |
| 398 | CD | GLN | A | 177 | -18.467 | 17.978 | 78.032 | 1.00 | 36.45 |

FIGURE 3H

| A | B | C | D | E | F | G | H | I | J |
|---|---|---|---|---|---|---|---|---|---|
| 399 | OE1 | GLN | A | 177 | -19.540 | 18.436 | 78.382 | 1.00 | 43.55 |
| 400 | NE2 | GLN | A | 177 | -17.393 | 17.992 | 78.801 | 1.00 | 32.42 |
| 401 | C | GLN | A | 177 | -15.672 | 17.586 | 73.966 | 1.00 | 39.55 |
| 402 | O | GLN | A | 177 | -15.519 | 18.636 | 73.379 | 1.00 | 40.58 |
| 403 | N | LEU | A | 178 | -14.691 | 16.722 | 74.144 | 1.00 | 38.53 |
| 404 | CA | LEU | A | 178 | -13.396 | 17.016 | 73.556 | 1.00 | 38.40 |
| 405 | CB | LEU | A | 178 | -12.332 | 16.028 | 73.974 | 1.00 | 37.56 |
| 406 | CG | LEU | A | 178 | -10.937 | 16.463 | 73.548 | 1.00 | 39.19 |
| 407 | CD1 | LEU | A | 178 | -10.647 | 17.912 | 74.074 | 1.00 | 42.88 |
| 408 | CD2 | LEU | A | 178 | -9.892 | 15.543 | 74.112 | 1.00 | 42.48 |
| 409 | C | LEU | A | 178 | -13.537 | 17.041 | 72.039 | 1.00 | 38.85 |
| 410 | O | LEU | A | 178 | -12.977 | 17.902 | 71.384 | 1.00 | 38.48 |
| 411 | N | ARG | A | 179 | -14.362 | 16.156 | 71.478 | 1.00 | 38.80 |
| 412 | CA | ARG | A | 179 | -14.528 | 16.156 | 70.027 | 1.00 | 38.95 |
| 413 | CB | ARG | A | 179 | -15.552 | 15.134 | 69.583 | 1.00 | 41.23 |
| 414 | CG | ARG | A | 179 | -15.211 | 14.622 | 68.199 | 1.00 | 45.48 |
| 415 | CD | ARG | A | 179 | -15.384 | 13.090 | 68.099 | 1.00 | 56.58 |
| 416 | NE | ARG | A | 179 | -16.441 | 12.637 | 69.012 | 1.00 | 57.68 |
| 417 | CZ | ARG | A | 179 | -16.275 | 11.730 | 69.973 | 1.00 | 57.26 |
| 418 | NH1 | ARG | A | 179 | -17.291 | 11.381 | 70.749 | 1.00 | 53.81 |
| 419 | NH2 | ARG | A | 179 | -15.093 | 11.162 | 70.159 | 1.00 | 59.58 |
| 420 | C | ARG | A | 179 | -15.092 | 17.456 | 69.558 | 1.00 | 38.62 |
| 421 | O | ARG | A | 179 | -14.762 | 17.995 | 68.508 | 1.00 | 38.21 |
| 422 | N | ARG | A | 180 | -16.042 | 17.943 | 70.318 | 1.00 | 39.35 |
| 423 | CA | ARG | A | 180 | -16.739 | 19.126 | 69.851 | 1.00 | 41.02 |
| 424 | CB | ARG | A | 180 | -18.096 | 19.338 | 70.575 | 1.00 | 41.10 |
| 425 | CG | ARG | A | 180 | -19.359 | 19.248 | 69.686 | 1.00 | 48.65 |
| 426 | CD | ARG | A | 180 | -20.364 | 18.182 | 70.125 | 1.00 | 56.75 |
| 427 | NE | ARG | A | 180 | -20.662 | 18.254 | 71.551 | 1.00 | 60.82 |
| 428 | CZ | ARG | A | 180 | -21.716 | 17.672 | 72.127 | 1.00 | 64.30 |
| 429 | NH1 | ARG | A | 180 | -21.941 | 17.819 | 73.430 | 1.00 | 64.17 |
| 430 | NH2 | ARG | A | 180 | -22.566 | 16.958 | 71.400 | 1.00 | 65.87 |
| 431 | C | ARG | A | 180 | -15.888 | 20.374 | 69.923 | 1.00 | 39.65 |
| 432 | O | ARG | A | 180 | -15.924 | 21.204 | 69.026 | 1.00 | 38.25 |
| 433 | N | GLU | A | 181 | -15.136 | 20.501 | 71.003 | 1.00 | 39.01 |
| 434 | CA | GLU | A | 181 | -14.302 | 21.665 | 71.254 | 1.00 | 38.98 |
| 435 | CB | GLU | A | 181 | -13.453 | 21.368 | 72.514 | 1.00 | 39.58 |
| 436 | CG | GLU | A | 181 | -12.421 | 22.429 | 72.937 | 1.00 | 41.25 |
| 437 | CD | GLU | A | 181 | -11.926 | 22.254 | 74.396 | 1.00 | 44.88 |
| 438 | OE1 | GLU | A | 181 | -10.944 | 22.921 | 74.792 | 1.00 | 48.21 |
| 439 | OE2 | GLU | A | 181 | -12.528 | 21.477 | 75.192 | 1.00 | 45.90 |
| 440 | C | GLU | A | 181 | -13.361 | 21.802 | 70.074 | 1.00 | 38.90 |
| 441 | O | GLU | A | 181 | -13.111 | 22.894 | 69.576 | 1.00 | 38.31 |
| 442 | N | VAL | A | 182 | -12.803 | 20.667 | 69.651 | 1.00 | 38.34 |
| 443 | CA | VAL | A | 182 | -11.850 | 20.639 | 68.537 | 1.00 | 38.73 |
| 444 | CB | VAL | A | 182 | -11.090 | 19.274 | 68.390 | 1.00 | 40.09 |
| 445 | CG1 | VAL | A | 182 | -10.416 | 19.128 | 66.980 | 1.00 | 40.39 |
| 446 | CG2 | VAL | A | 182 | -10.051 | 19.079 | 69.506 | 1.00 | 38.26 |
| 447 | C | VAL | A | 182 | -12.541 | 20.959 | 67.237 | 1.00 | 38.65 |
| 448 | O | VAL | A | 182 | -12.119 | 21.839 | 66.516 | 1.00 | 39.07 |
| 449 | N | ALA | A | 183 | -13.656 | 20.285 | 66.957 | 1.00 | 39.36 |

FIGURE 3I

| A | B | C | D | E | F | G | H | I | J |
|---|---|---|---|---|---|---|---|---|---|
| 450 | CA | ALA | A | 183 | -14.312 | 20.503 | 65.679 | 1.00 | 40.14 |
| 451 | CB | ALA | A | 183 | -15.334 | 19.370 | 65.405 | 1.00 | 41.08 |
| 452 | C | ALA | A | 183 | -14.965 | 21.870 | 65.636 | 1.00 | 40.80 |
| 453 | O | ALA | A | 183 | -14.972 | 22.545 | 64.609 | 1.00 | 41.84 |
| 454 | N | ILE | A | 184 | -15.524 | 22.312 | 66.748 | 1.00 | 38.99 |
| 455 | CA | ILE | A | 184 | -16.157 | 23.595 | 66.678 | 1.00 | 39.48 |
| 456 | CB | ILE | A | 184 | -17.210 | 23.754 | 67.766 | 1.00 | 38.90 |
| 457 | CG1 | ILE | A | 184 | -18.387 | 22.819 | 67.472 | 1.00 | 42.19 |
| 458 | CD1 | ILE | A | 184 | -19.459 | 22.799 | 68.584 | 1.00 | 40.68 |
| 459 | CG2 | ILE | A | 184 | -17.715 | 25.164 | 67.777 | 1.00 | 40.73 |
| 460 | C | ILE | A | 184 | -15.124 | 24.703 | 66.747 | 1.00 | 39.32 |
| 461 | O | ILE | A | 184 | -15.148 | 25.635 | 65.929 | 1.00 | 38.88 |
| 462 | N | GLN | A | 185 | -14.209 | 24.612 | 67.723 | 1.00 | 38.82 |
| 463 | CA | GLN | A | 185 | -13.281 | 25.717 | 67.911 | 1.00 | 38.20 |
| 464 | CB | GLN | A | 185 | -12.446 | 25.531 | 69.185 | 1.00 | 38.61 |
| 465 | CG | GLN | A | 185 | -12.426 | 26.806 | 70.015 | 1.00 | 36.79 |
| 466 | CD | GLN | A | 185 | -11.623 | 26.663 | 71.277 | 1.00 | 38.97 |
| 467 | OE1 | GLN | A | 185 | -10.817 | 27.519 | 71.599 | 1.00 | 35.32 |
| 468 | NE2 | GLN | A | 185 | -11.869 | 25.627 | 71.997 | 1.00 | 32.38 |
| 469 | C | GLN | A | 185 | -12.337 | 25.905 | 66.754 | 1.00 | 38.81 |
| 470 | O | GLN | A | 185 | -11.936 | 27.027 | 66.479 | 1.00 | 37.38 |
| 471 | N | SER | A | 186 | -11.946 | 24.823 | 66.083 | 1.00 | 39.57 |
| 472 | CA | SER | A | 186 | -10.957 | 25.005 | 65.007 | 1.00 | 41.86 |
| 473 | CB | SER | A | 186 | -10.302 | 23.684 | 64.569 | 1.00 | 41.93 |
| 474 | OG | SER | A | 186 | -11.289 | 22.671 | 64.412 | 1.00 | 42.48 |
| 475 | C | SER | A | 186 | -11.509 | 25.748 | 63.798 | 1.00 | 42.50 |
| 476 | O | SER | A | 186 | -10.761 | 26.297 | 63.017 | 1.00 | 43.08 |
| 477 | N | HIS | A | 187 | -12.817 | 25.781 | 63.656 | 1.00 | 43.53 |
| 478 | CA | HIS | A | 187 | -13.397 | 26.411 | 62.471 | 1.00 | 45.61 |
| 479 | CB | HIS | A | 187 | -14.585 | 25.580 | 61.955 | 1.00 | 46.41 |
| 480 | CG | HIS | A | 187 | -14.173 | 24.264 | 61.396 | 1.00 | 52.65 |
| 481 | ND1 | HIS | A | 187 | -14.352 | 23.934 | 60.072 | 1.00 | 58.39 |
| 482 | CE1 | HIS | A | 187 | -13.863 | 22.725 | 59.855 | 1.00 | 58.68 |
| 483 | NE2 | HIS | A | 187 | -13.354 | 22.269 | 60.986 | 1.00 | 59.03 |
| 484 | CD2 | HIS | A | 187 | -13.527 | 23.215 | 61.965 | 1.00 | 56.31 |
| 485 | C | HIS | A | 187 | -13.815 | 27.843 | 62.684 | 1.00 | 44.76 |
| 486 | O | HIS | A | 187 | -13.962 | 28.608 | 61.725 | 1.00 | 44.78 |
| 487 | N | LEU | A | 188 | -13.984 | 28.229 | 63.945 | 1.00 | 44.38 |
| 488 | CA | LEU | A | 188 | -14.351 | 29.612 | 64.257 | 1.00 | 43.43 |
| 489 | CB | LEU | A | 188 | -14.767 | 29.748 | 65.747 | 1.00 | 43.01 |
| 490 | CG | LEU | A | 188 | -15.964 | 28.891 | 66.146 | 1.00 | 43.56 |
| 491 | CD1 | LEU | A | 188 | -16.328 | 29.051 | 67.640 | 1.00 | 41.71 |
| 492 | CD2 | LEU | A | 188 | -17.109 | 29.282 | 65.302 | 1.00 | 41.54 |
| 493 | C | LEU | A | 188 | -13.143 | 30.477 | 64.001 | 1.00 | 42.37 |
| 494 | O | LEU | A | 188 | -12.036 | 30.079 | 64.321 | 1.00 | 43.11 |
| 495 | N | ARG | A | 189 | -13.365 | 31.677 | 63.478 | 1.00 | 42.12 |
| 496 | CA | ARG | A | 189 | -12.293 | 32.644 | 63.200 | 1.00 | 42.01 |
| 497 | CB | ARG | A | 189 | -11.962 | 32.682 | 61.695 | 1.00 | 42.31 |
| 498 | CG | ARG | A | 189 | -11.239 | 31.477 | 61.229 | 1.00 | 44.33 |
| 499 | CD | ARG | A | 189 | -9.871 | 31.267 | 61.898 | 1.00 | 46.81 |
| 500 | NE | ARG | A | 189 | -9.128 | 30.280 | 61.109 | 1.00 | 54.20 |

FIGURE 3J

| A | B | C | D | E | F | G | H | I | J |
|---|---|---|---|---|---|---|---|---|---|
| 501 | CZ | ARG | A | 189 | -9.335 | 28.979 | 61.187 | 1.00 | 56.68 |
| 502 | NH1 | ARG | A | 189 | -8.643 | 28.153 | 60.419 | 1.00 | 58.82 |
| 503 | NH2 | ARG | A | 189 | -10.230 | 28.496 | 62.049 | 1.00 | 57.84 |
| 504 | C | ARG | A | 189 | -12.809 | 34.010 | 63.580 | 1.00 | 41.15 |
| 505 | O | ARG | A | 189 | -13.554 | 34.620 | 62.819 | 1.00 | 41.64 |
| 506 | N | HIS | A | 190 | -12.402 | 34.506 | 64.739 | 1.00 | 40.04 |
| 507 | CA | HIS | A | 190 | -12.901 | 35.775 | 65.194 | 1.00 | 38.65 |
| 508 | CB | HIS | A | 190 | -14.316 | 35.605 | 65.760 | 1.00 | 38.81 |
| 509 | CG | HIS | A | 190 | -14.925 | 36.886 | 66.202 | 1.00 | 39.63 |
| 510 | ND1 | HIS | A | 190 | -15.866 | 37.557 | 65.454 | 1.00 | 40.19 |
| 511 | CE1 | HIS | A | 190 | -16.189 | 38.680 | 66.071 | 1.00 | 37.93 |
| 512 | NE2 | HIS | A | 190 | -15.486 | 38.762 | 67.184 | 1.00 | 36.58 |
| 513 | CD2 | HIS | A | 190 | -14.671 | 37.664 | 67.284 | 1.00 | 33.70 |
| 514 | C | HIS | A | 190 | -11.906 | 36.363 | 66.185 | 1.00 | 37.98 |
| 515 | O | HIS | A | 190 | -11.329 | 35.649 | 66.986 | 1.00 | 38.30 |
| 516 | N | PRO | A | 191 | -11.640 | 37.657 | 66.113 | 1.00 | 38.45 |
| 517 | CA | PRO | A | 191 | -10.581 | 38.239 | 66.953 | 1.00 | 36.82 |
| 518 | CB | PRO | A | 191 | -10.615 | 39.701 | 66.553 | 1.00 | 37.97 |
| 519 | CG | PRO | A | 191 | -12.033 | 39.881 | 66.066 | 1.00 | 38.87 |
| 520 | CD | PRO | A | 191 | -12.253 | 38.668 | 65.234 | 1.00 | 38.97 |
| 521 | C | PRO | A | 191 | -10.903 | 38.055 | 68.457 | 1.00 | 35.66 |
| 522 | O | PRO | A | 191 | -9.992 | 38.127 | 69.276 | 1.00 | 34.96 |
| 523 | N | ASN | A | 192 | -12.158 | 37.814 | 68.804 | 1.00 | 34.30 |
| 524 | CA | ASN | A | 192 | -12.523 | 37.581 | 70.217 | 1.00 | 33.52 |
| 525 | CB | ASN | A | 192 | -13.612 | 38.556 | 70.663 | 1.00 | 32.97 |
| 526 | CG | ASN | A | 192 | -13.207 | 40.027 | 70.497 | 1.00 | 35.71 |
| 527 | OD1 | ASN | A | 192 | -12.286 | 40.503 | 71.178 | 1.00 | 35.61 |
| 528 | ND2 | ASN | A | 192 | -13.823 | 40.714 | 69.556 | 1.00 | 31.27 |
| 529 | C | ASN | A | 192 | -12.871 | 36.123 | 70.646 | 1.00 | 32.20 |
| 530 | O | ASN | A | 192 | -13.603 | 35.887 | 71.624 | 1.00 | 31.19 |
| 531 | N | ILE | A | 193 | -12.368 | 35.159 | 69.890 | 1.00 | 30.72 |
| 532 | CA | ILE | A | 193 | -12.535 | 33.743 | 70.202 | 1.00 | 31.30 |
| 533 | CB | ILE | A | 193 | -13.428 | 33.071 | 69.151 | 1.00 | 31.25 |
| 534 | CG1 | ILE | A | 193 | -14.862 | 33.600 | 69.252 | 1.00 | 32.94 |
| 535 | CD1 | ILE | A | 193 | -15.777 | 33.149 | 68.134 | 1.00 | 36.50 |
| 536 | CG2 | ILE | A | 193 | -13.371 | 31.550 | 69.293 | 1.00 | 29.33 |
| 537 | C | ILE | A | 193 | -11.166 | 33.124 | 70.102 | 1.00 | 30.85 |
| 538 | O | ILE | A | 193 | -10.472 | 33.376 | 69.121 | 1.00 | 31.20 |
| 539 | N | LEU | A | 194 | -10.764 | 32.311 | 71.085 | 1.00 | 29.48 |
| 540 | CA | LEU | A | 194 | -9.497 | 31.652 | 71.065 | 1.00 | 30.26 |
| 541 | CB | LEU | A | 194 | -9.165 | 31.043 | 72.422 | 1.00 | 28.89 |
| 542 | CG | LEU | A | 194 | -7.685 | 30.760 | 72.565 | 1.00 | 31.38 |
| 543 | CD1 | LEU | A | 194 | -6.957 | 32.083 | 72.928 | 1.00 | 27.79 |
| 544 | CD2 | LEU | A | 194 | -7.565 | 29.741 | 73.655 | 1.00 | 30.09 |
| 545 | C | LEU | A | 194 | -9.417 | 30.580 | 69.984 | 1.00 | 30.59 |
| 546 | O | LEU | A | 194 | -10.224 | 29.651 | 69.930 | 1.00 | 31.64 |
| 547 | N | ARG | A | 195 | -8.411 | 30.745 | 69.139 | 1.00 | 31.20 |
| 548 | CA | ARG | A | 195 | -8.121 | 29.904 | 68.003 | 1.00 | 32.25 |
| 549 | CB | ARG | A | 195 | -7.026 | 30.648 | 67.258 | 1.00 | 33.95 |
| 550 | CG | ARG | A | 195 | -6.742 | 30.234 | 65.886 | 1.00 | 42.54 |
| 551 | CD | ARG | A | 195 | -7.805 | 30.522 | 64.863 | 1.00 | 46.96 |

FIGURE 3K

| A | B | C | D | E | F | G | H | I | J |
|---|---|---|---|---|---|---|---|---|---|
| 552 | NE | ARG | A | 195 | -7.275 | 29.900 | 63.663 | 1.00 | 52.66 |
| 553 | CZ | ARG | A | 195 | -6.358 | 30.480 | 62.912 | 1.00 | 56.14 |
| 554 | NH1 | ARG | A | 195 | -5.941 | 31.694 | 63.224 | 1.00 | 56.04 |
| 555 | NH2 | ARG | A | 195 | -5.861 | 29.867 | 61.844 | 1.00 | 60.45 |
| 556 | C | ARG | A | 195 | -7.580 | 28.611 | 68.529 | 1.00 | 30.98 |
| 557 | O | ARG | A | 195 | -6.771 | 28.614 | 69.450 | 1.00 | 28.95 |
| 558 | N | LEU | A | 196 | -8.015 | 27.509 | 67.984 | 1.00 | 31.25 |
| 559 | CA | LEU | A | 196 | -7.440 | 26.226 | 68.277 | 1.00 | 31.50 |
| 560 | CB | LEU | A | 196 | -8.517 | 25.265 | 68.720 | 1.00 | 32.30 |
| 561 | CG | LEU | A | 196 | -8.057 | 23.870 | 69.131 | 1.00 | 33.64 |
| 562 | CD1 | LEU | A | 196 | -9.058 | 23.370 | 70.151 | 1.00 | 36.24 |
| 563 | CD2 | LEU | A | 196 | -8.117 | 23.052 | 67.904 | 1.00 | 34.95 |
| 564 | C | LEU | A | 196 | -6.795 | 25.867 | 66.932 | 1.00 | 35.11 |
| 565 | O | LEU | A | 196 | -7.445 | 25.957 | 65.875 | 1.00 | 34.69 |
| 566 | N | TYR | A | 197 | -5.509 | 25.518 | 66.972 | 1.00 | 36.02 |
| 567 | CA | TYR | A | 197 | -4.765 | 25.276 | 65.763 | 1.00 | 37.91 |
| 568 | CB | TYR | A | 197 | -3.331 | 25.747 | 65.950 | 1.00 | 39.49 |
| 569 | CG | TYR | A | 197 | -3.243 | 27.233 | 66.128 | 1.00 | 40.35 |
| 570 | CD1 | TYR | A | 197 | -2.704 | 27.782 | 67.278 | 1.00 | 43.33 |
| 571 | CE1 | TYR | A | 197 | -2.619 | 29.122 | 67.439 | 1.00 | 43.54 |
| 572 | CZ | TYR | A | 197 | -3.072 | 29.953 | 66.451 | 1.00 | 44.37 |
| 573 | OH | TYR | A | 197 | -2.949 | 31.310 | 66.604 | 1.00 | 48.37 |
| 574 | CE2 | TYR | A | 197 | -3.603 | 29.455 | 65.296 | 1.00 | 45.10 |
| 575 | CD2 | TYR | A | 197 | -3.697 | 28.087 | 65.139 | 1.00 | 44.72 |
| 576 | C | TYR | A | 197 | -4.762 | 23.826 | 65.380 | 1.00 | 38.77 |
| 577 | O | TYR | A | 197 | -4.536 | 23.490 | 64.216 | 1.00 | 39.64 |
| 578 | N | GLY | A | 198 | -4.976 | 22.955 | 66.351 | 1.00 | 37.60 |
| 579 | CA | GLY | A | 198 | -5.013 | 21.553 | 66.019 | 1.00 | 38.52 |
| 580 | C | GLY | A | 198 | -4.785 | 20.771 | 67.265 | 1.00 | 38.86 |
| 581 | O | GLY | A | 198 | -4.900 | 21.311 | 68.409 | 1.00 | 36.64 |
| 582 | N | TYR | A | 199 | -4.428 | 19.511 | 67.066 | 1.00 | 38.68 |
| 583 | CA | TYR | A | 199 | -4.334 | 18.597 | 68.185 | 1.00 | 40.56 |
| 584 | CB | TYR | A | 199 | -5.731 | 18.163 | 68.637 | 1.00 | 39.96 |
| 585 | CG | TYR | A | 199 | -6.334 | 17.067 | 67.753 | 1.00 | 44.40 |
| 586 | CD1 | TYR | A | 199 | -7.074 | 17.385 | 66.618 | 1.00 | 44.98 |
| 587 | CE1 | TYR | A | 199 | -7.626 | 16.382 | 65.807 | 1.00 | 48.78 |
| 588 | CZ | TYR | A | 199 | -7.420 | 15.058 | 66.132 | 1.00 | 50.76 |
| 589 | OH | TYR | A | 199 | -7.947 | 14.040 | 65.357 | 1.00 | 58.47 |
| 590 | CE2 | TYR | A | 199 | -6.697 | 14.722 | 67.244 | 1.00 | 51.67 |
| 591 | CD2 | TYR | A | 199 | -6.160 | 15.736 | 68.060 | 1.00 | 46.05 |
| 592 | C | TYR | A | 199 | -3.517 | 17.369 | 67.877 | 1.00 | 40.55 |
| 593 | O | TYR | A | 199 | -3.291 | 17.055 | 66.728 | 1.00 | 40.45 |
| 594 | N | PHE | A | 200 | -3.066 | 16.670 | 68.911 | 1.00 | 40.86 |
| 595 | CA | PHE | A | 200 | -2.416 | 15.411 | 68.656 | 1.00 | 42.07 |
| 596 | CB | PHE | A | 200 | -0.963 | 15.636 | 68.198 | 1.00 | 41.03 |
| 597 | CG | PHE | A | 200 | -0.122 | 16.422 | 69.173 | 1.00 | 44.63 |
| 598 | CD1 | PHE | A | 200 | 0.713 | 15.760 | 70.035 | 1.00 | 42.87 |
| 599 | CE1 | PHE | A | 200 | 1.515 | 16.436 | 70.934 | 1.00 | 44.73 |
| 600 | CZ | PHE | A | 200 | 1.477 | 17.801 | 71.010 | 1.00 | 43.50 |
| 601 | CE2 | PHE | A | 200 | 0.655 | 18.492 | 70.162 | 1.00 | 43.78 |
| 602 | CD2 | PHE | A | 200 | -0.191 | 17.817 | 69.254 | 1.00 | 43.04 |

FIGURE 3L

| A | B | C | D | E | F | G | H | I | J |
|---|---|---|---|---|---|---|---|---|---|
| 603 | C | PHE | A | 200 | -2.610 | 14.522 | 69.888 | 1.00 | 42.82 |
| 604 | O | PHE | A | 200 | -3.188 | 14.961 | 70.897 | 1.00 | 39.88 |
| 605 | N | HIS | A | 201 | -2.268 | 13.251 | 69.770 | 1.00 | 44.66 |
| 606 | CA | HIS | A | 201 | -2.394 | 12.350 | 70.911 | 1.00 | 48.80 |
| 607 | CB | HIS | A | 201 | -3.807 | 11.739 | 70.991 | 1.00 | 49.16 |
| 608 | CG | HIS | A | 201 | -4.132 | 10.793 | 69.870 | 1.00 | 53.25 |
| 609 | ND1 | HIS | A | 201 | -3.940 | 9.429 | 69.956 | 1.00 | 57.68 |
| 610 | CE1 | HIS | A | 201 | -4.339 | 8.855 | 68.832 | 1.00 | 58.86 |
| 611 | NE2 | HIS | A | 201 | -4.794 | 9.797 | 68.024 | 1.00 | 58.83 |
| 612 | CD2 | HIS | A | 201 | -4.676 | 11.018 | 68.650 | 1.00 | 57.09 |
| 613 | C | HIS | A | 201 | -1.323 | 11.281 | 70.980 | 1.00 | 49.89 |
| 614 | O | HIS | A | 201 | -0.807 | 10.810 | 69.960 | 1.00 | 50.59 |
| 615 | N | ASP | A | 202 | -0.983 | 10.943 | 72.219 | 1.00 | 52.70 |
| 616 | CA | ASP | A | 202 | -0.084 | 9.828 | 72.492 | 1.00 | 53.99 |
| 617 | CB | ASP | A | 202 | 1.241 | 10.287 | 73.079 | 1.00 | 54.12 |
| 618 | CG | ASP | A | 202 | 1.098 | 10.887 | 74.444 | 1.00 | 55.69 |
| 619 | OD1 | ASP | A | 202 | 0.064 | 10.619 | 75.099 | 1.00 | 54.93 |
| 620 | OD2 | ASP | A | 202 | 2.000 | 11.609 | 74.943 | 1.00 | 54.23 |
| 621 | C | ASP | A | 202 | -0.819 | 8.790 | 73.330 | 1.00 | 54.16 |
| 622 | O | ASP | A | 202 | -2.064 | 8.730 | 73.308 | 1.00 | 54.26 |
| 623 | N | ALA | A | 203 | -0.084 | 7.976 | 74.067 | 1.00 | 54.51 |
| 624 | CA | ALA | A | 203 | -0.738 | 6.843 | 74.732 | 1.00 | 54.56 |
| 625 | CB | ALA | A | 203 | 0.314 | 5.869 | 75.285 | 1.00 | 54.78 |
| 626 | C | ALA | A | 203 | -1.716 | 7.242 | 75.824 | 1.00 | 54.14 |
| 627 | O | ALA | A | 203 | -2.869 | 6.753 | 75.887 | 1.00 | 54.14 |
| 628 | N | THR | A | 204 | -1.254 | 8.141 | 76.681 | 1.00 | 52.74 |
| 629 | CA | THR | A | 204 | -2.040 | 8.535 | 77.833 | 1.00 | 51.77 |
| 630 | CB | THR | A | 204 | -1.114 | 8.467 | 79.073 | 1.00 | 52.77 |
| 631 | OG1 | THR | A | 204 | -1.821 | 8.827 | 80.286 | 1.00 | 56.55 |
| 632 | CG2 | THR | A | 204 | -0.003 | 9.483 | 78.940 | 1.00 | 51.61 |
| 633 | C | THR | A | 204 | -2.689 | 9.929 | 77.704 | 1.00 | 50.02 |
| 634 | O | THR | A | 204 | -3.546 | 10.290 | 78.496 | 1.00 | 48.39 |
| 635 | N | ARG | A | 205 | -2.312 | 10.702 | 76.693 | 1.00 | 48.75 |
| 636 | CA | ARG | A | 205 | -2.797 | 12.093 | 76.643 | 1.00 | 47.39 |
| 637 | CB | ARG | A | 205 | -1.740 | 13.047 | 77.192 | 1.00 | 47.22 |
| 638 | CG | ARG | A | 205 | -1.295 | 12.746 | 78.573 | 1.00 | 50.14 |
| 639 | CD | ARG | A | 205 | 0.224 | 12.732 | 78.698 | 1.00 | 59.09 |
| 640 | NE | ARG | A | 205 | 0.805 | 13.946 | 79.262 | 1.00 | 65.81 |
| 641 | CZ | ARG | A | 205 | 2.118 | 14.116 | 79.455 | 1.00 | 71.17 |
| 642 | NH1 | ARG | A | 205 | 2.587 | 15.256 | 79.974 | 1.00 | 73.74 |
| 643 | NH2 | ARG | A | 205 | 2.968 | 13.142 | 79.123 | 1.00 | 72.85 |
| 644 | C | ARG | A | 205 | -3.228 | 12.598 | 75.293 | 1.00 | 44.76 |
| 645 | O | ARG | A | 205 | -2.831 | 12.070 | 74.258 | 1.00 | 44.49 |
| 646 | N | VAL | A | 206 | -4.119 | 13.582 | 75.354 | 1.00 | 42.03 |
| 647 | CA | VAL | A | 206 | -4.578 | 14.339 | 74.206 | 1.00 | 40.02 |
| 648 | CB | VAL | A | 206 | -6.136 | 14.273 | 74.061 | 1.00 | 40.51 |
| 649 | CG1 | VAL | A | 206 | -6.638 | 15.182 | 72.954 | 1.00 | 41.85 |
| 650 | CG2 | VAL | A | 206 | -6.580 | 12.851 | 73.737 | 1.00 | 41.32 |
| 651 | C | VAL | A | 206 | -4.039 | 15.785 | 74.414 | 1.00 | 38.80 |
| 652 | O | VAL | A | 206 | -3.996 | 16.298 | 75.539 | 1.00 | 38.31 |
| 653 | N | TYR | A | 207 | -3.593 | 16.409 | 73.341 | 1.00 | 37.44 |
| 654 | CA | TYR | A | 207 | -2.976 | 17.737 | 73.430 | 1.00 | 38.03 |

FIGURE 3M

| A | B | C | D | E | F | G | H | I | J |
|---|---|---|---|---|---|---|---|---|---|
| 655 | CB | TYR | A | 207 | -1.549 | 17.670 | 72.968 | 1.00 | 36.40 |
| 656 | CG | TYR | A | 207 | -0.688 | 16.778 | 73.766 | 1.00 | 39.00 |
| 657 | CD1 | TYR | A | 207 | -0.010 | 17.249 | 74.881 | 1.00 | 39.70 |
| 658 | CE1 | TYR | A | 207 | 0.818 | 16.417 | 75.590 | 1.00 | 44.38 |
| 659 | CZ | TYR | A | 207 | 0.948 | 15.092 | 75.187 | 1.00 | 45.91 |
| 660 | OH | TYR | A | 207 | 1.734 | 14.246 | 75.900 | 1.00 | 50.45 |
| 661 | CE2 | TYR | A | 207 | 0.290 | 14.609 | 74.090 | 1.00 | 43.62 |
| 662 | CD2 | TYR | A | 207 | -0.539 | 15.439 | 73.398 | 1.00 | 40.40 |
| 663 | C | TYR | A | 207 | -3.595 | 18.728 | 72.511 | 1.00 | 37.21 |
| 664 | O | TYR | A | 207 | -3.384 | 18.643 | 71.286 | 1.00 | 39.25 |
| 665 | N | LEU | A | 208 | -4.323 | 19.685 | 73.049 | 1.00 | 35.21 |
| 666 | CA | LEU | A | 208 | -4.858 | 20.693 | 72.172 | 1.00 | 32.76 |
| 667 | CB | LEU | A | 208 | -6.177 | 21.235 | 72.710 | 1.00 | 32.84 |
| 668 | CG | LEU | A | 208 | -7.403 | 20.429 | 72.312 | 1.00 | 36.54 |
| 669 | CD1 | LEU | A | 208 | -7.148 | 18.880 | 72.249 | 1.00 | 39.94 |
| 670 | CD2 | LEU | A | 208 | -8.584 | 20.792 | 73.169 | 1.00 | 34.97 |
| 671 | C | LEU | A | 208 | -3.851 | 21.827 | 71.975 | 1.00 | 31.94 |
| 672 | O | LEU | A | 208 | -3.292 | 22.378 | 72.960 | 1.00 | 31.89 |
| 673 | N | ILE | A | 209 | -3.605 | 22.175 | 70.710 | 1.00 | 27.64 |
| 674 | CA | ILE | A | 209 | -2.719 | 23.286 | 70.374 | 1.00 | 29.03 |
| 675 | CB | ILE | A | 209 | -2.034 | 23.047 | 69.043 | 1.00 | 29.46 |
| 676 | CG1 | ILE | A | 209 | -1.424 | 21.632 | 68.983 | 1.00 | 33.03 |
| 677 | CD1 | ILE | A | 209 | -0.629 | 21.353 | 67.616 | 1.00 | 36.54 |
| 678 | CG2 | ILE | A | 209 | -0.996 | 24.092 | 68.833 | 1.00 | 27.57 |
| 679 | C | ILE | A | 209 | -3.518 | 24.572 | 70.249 | 1.00 | 29.27 |
| 680 | O | ILE | A | 209 | -4.206 | 24.763 | 69.258 | 1.00 | 30.08 |
| 681 | N | LEU | A | 210 | -3.372 | 25.462 | 71.226 | 1.00 | 27.89 |
| 682 | CA | LEU | A | 210 | -4.143 | 26.671 | 71.304 | 1.00 | 28.36 |
| 683 | CB | LEU | A | 210 | -4.768 | 26.757 | 72.729 | 1.00 | 26.97 |
| 684 | CG | LEU | A | 210 | -5.603 | 25.569 | 73.209 | 1.00 | 31.79 |
| 685 | CD1 | LEU | A | 210 | -6.165 | 25.926 | 74.613 | 1.00 | 31.27 |
| 686 | CD2 | LEU | A | 210 | -6.798 | 25.282 | 72.204 | 1.00 | 34.08 |
| 687 | C | LEU | A | 210 | -3.346 | 27.967 | 71.066 | 1.00 | 26.61 |
| 688 | O | LEU | A | 210 | -2.177 | 28.060 | 71.382 | 1.00 | 27.93 |
| 689 | N | GLU | A | 211 | -3.994 | 28.972 | 70.520 | 1.00 | 29.15 |
| 690 | CA | GLU | A | 211 | -3.501 | 30.350 | 70.621 | 1.00 | 29.81 |
| 691 | CB | GLU | A | 211 | -4.498 | 31.350 | 70.047 | 1.00 | 31.22 |
| 692 | CG | GLU | A | 211 | -3.984 | 32.779 | 70.020 | 1.00 | 35.70 |
| 693 | CD | GLU | A | 211 | -5.147 | 33.799 | 70.050 | 1.00 | 39.08 |
| 694 | OE1 | GLU | A | 211 | -4.932 | 34.950 | 70.489 | 1.00 | 43.39 |
| 695 | OE2 | GLU | A | 211 | -6.288 | 33.455 | 69.653 | 1.00 | 38.36 |
| 696 | C | GLU | A | 211 | -3.161 | 30.663 | 72.128 | 1.00 | 29.58 |
| 697 | O | GLU | A | 211 | -3.948 | 30.404 | 73.014 | 1.00 | 28.54 |
| 698 | N | TYR | A | 212 | -1.957 | 31.153 | 72.381 | 1.00 | 28.23 |
| 699 | CA | TYR | A | 212 | -1.550 | 31.606 | 73.725 | 1.00 | 28.20 |
| 700 | CB | TYR | A | 212 | -0.028 | 31.697 | 73.739 | 1.00 | 28.08 |
| 701 | CG | TYR | A | 212 | 0.592 | 32.494 | 74.874 | 1.00 | 29.44 |
| 702 | CD1 | TYR | A | 212 | 1.521 | 33.489 | 74.601 | 1.00 | 30.49 |
| 703 | CE1 | TYR | A | 212 | 2.131 | 34.197 | 75.639 | 1.00 | 36.30 |
| 704 | CZ | TYR | A | 212 | 1.773 | 33.945 | 76.903 | 1.00 | 33.49 |
| 705 | OH | TYR | A | 212 | 2.383 | 34.655 | 77.887 | 1.00 | 37.20 |

FIGURE 3N

| A | B | C | D | E | F | G | H | I | J |
|---|---|---|---|---|---|---|---|---|---|
| 706 | CE2 | TYR | A | 212 | 0.802 | 32.977 | 77.225 | 1.00 | 33.16 |
| 707 | CD2 | TYR | A | 212 | 0.234 | 32.258 | 76.188 | 1.00 | 28.40 |
| 708 | C | TYR | A | 212 | -2.183 | 33.022 | 74.034 | 1.00 | 28.48 |
| 709 | O | TYR | A | 212 | -2.089 | 33.924 | 73.211 | 1.00 | 27.53 |
| 710 | N | ALA | A | 213 | -2.836 | 33.156 | 75.205 | 1.00 | 28.23 |
| 711 | CA | ALA | A | 213 | -3.431 | 34.424 | 75.650 | 1.00 | 30.33 |
| 712 | CB | ALA | A | 213 | -4.884 | 34.284 | 76.103 | 1.00 | 28.94 |
| 713 | C | ALA | A | 213 | -2.550 | 34.953 | 76.780 | 1.00 | 30.02 |
| 714 | O | ALA | A | 213 | -2.634 | 34.540 | 77.872 | 1.00 | 31.02 |
| 715 | N | PRO | A | 214 | -1.720 | 35.904 | 76.442 | 1.00 | 31.54 |
| 716 | CA | PRO | A | 214 | -0.632 | 36.365 | 77.313 | 1.00 | 32.57 |
| 717 | CB | PRO | A | 214 | 0.219 | 37.264 | 76.395 | 1.00 | 32.48 |
| 718 | CG | PRO | A | 214 | -0.495 | 37.305 | 75.047 | 1.00 | 35.80 |
| 719 | CD | PRO | A | 214 | -1.853 | 36.639 | 75.171 | 1.00 | 30.79 |
| 720 | C | PRO | A | 214 | -1.070 | 37.096 | 78.596 | 1.00 | 34.06 |
| 721 | O | PRO | A | 214 | -0.408 | 36.972 | 79.644 | 1.00 | 35.53 |
| 722 | N | LEU | A | 215 | -2.187 | 37.789 | 78.548 | 1.00 | 33.98 |
| 723 | CA | LEU | A | 215 | -2.641 | 38.503 | 79.718 | 1.00 | 36.04 |
| 724 | CB | LEU | A | 215 | -3.341 | 39.786 | 79.296 | 1.00 | 34.70 |
| 725 | CG | LEU | A | 215 | -2.394 | 41.003 | 79.195 | 1.00 | 36.83 |
| 726 | CD1 | LEU | A | 215 | -1.157 | 40.725 | 78.377 | 1.00 | 35.83 |
| 727 | CD2 | LEU | A | 215 | -3.180 | 42.190 | 78.627 | 1.00 | 35.88 |
| 728 | C | LEU | A | 215 | -3.521 | 37.689 | 80.677 | 1.00 | 35.81 |
| 729 | O | LEU | A | 215 | -4.121 | 38.247 | 81.571 | 1.00 | 35.82 |
| 730 | N | GLY | A | 216 | -3.603 | 36.381 | 80.470 | 1.00 | 35.32 |
| 731 | CA | GLY | A | 216 | -4.326 | 35.503 | 81.372 | 1.00 | 34.32 |
| 732 | C | GLY | A | 216 | -5.848 | 35.530 | 81.287 | 1.00 | 32.64 |
| 733 | O | GLY | A | 216 | -6.426 | 35.895 | 80.257 | 1.00 | 32.48 |
| 734 | N | THR | A | 217 | -6.500 | 35.138 | 82.367 | 1.00 | 31.56 |
| 735 | CA | THR | A | 217 | -7.962 | 35.119 | 82.396 | 1.00 | 31.29 |
| 736 | CB | THR | A | 217 | -8.511 | 33.951 | 83.212 | 1.00 | 32.13 |
| 737 | OG1 | THR | A | 217 | -8.082 | 34.088 | 84.587 | 1.00 | 30.67 |
| 738 | CG2 | THR | A | 217 | -7.974 | 32.629 | 82.730 | 1.00 | 31.12 |
| 739 | C | THR | A | 217 | -8.613 | 36.355 | 83.020 | 1.00 | 31.68 |
| 740 | O | THR | A | 217 | -8.041 | 37.069 | 83.856 | 1.00 | 28.84 |
| 741 | N | VAL | A | 218 | -9.881 | 36.498 | 82.686 | 1.00 | 30.86 |
| 742 | CA | VAL | A | 218 | -10.694 | 37.528 | 83.283 | 1.00 | 32.14 |
| 743 | CB | VAL | A | 218 | -11.953 | 37.675 | 82.526 | 1.00 | 33.13 |
| 744 | CG1 | VAL | A | 218 | -12.978 | 38.466 | 83.328 | 1.00 | 35.75 |
| 745 | CG2 | VAL | A | 218 | -11.616 | 38.289 | 81.172 | 1.00 | 31.98 |
| 746 | C | VAL | A | 218 | -10.920 | 37.150 | 84.768 | 1.00 | 32.06 |
| 747 | O | VAL | A | 218 | -11.039 | 38.023 | 85.642 | 1.00 | 32.00 |
| 748 | N | TYR | A | 219 | -10.958 | 35.849 | 85.032 | 1.00 | 32.11 |
| 749 | CA | TYR | A | 219 | -11.062 | 35.374 | 86.402 | 1.00 | 33.66 |
| 750 | CB | TYR | A | 219 | -11.049 | 33.838 | 86.406 | 1.00 | 33.98 |
| 751 | CG | TYR | A | 219 | -11.116 | 33.234 | 87.785 | 1.00 | 35.91 |
| 752 | CD1 | TYR | A | 219 | -12.335 | 32.895 | 88.354 | 1.00 | 38.53 |
| 753 | CE1 | TYR | A | 219 | -12.412 | 32.339 | 89.620 | 1.00 | 46.18 |
| 754 | CZ | TYR | A | 219 | -11.236 | 32.109 | 90.335 | 1.00 | 47.58 |
| 755 | OH | TYR | A | 219 | -11.326 | 31.532 | 91.592 | 1.00 | 53.35 |
| 756 | CE2 | TYR | A | 219 | -10.001 | 32.451 | 89.785 | 1.00 | 42.92 |

FIGURE 3O

| A | B | C | D | E | F | G | H | I | J |
|---|---|---|---|---|---|---|---|---|---|
| 757 | CD2 | TYR | A | 219 | -9.954 | 32.999 | 88.517 | 1.00 | 37.24 |
| 758 | C | TYR | A | 219 | -9.883 | 35.936 | 87.269 | 1.00 | 33.62 |
| 759 | O | TYR | A | 219 | -10.105 | 36.423 | 88.379 | 1.00 | 33.27 |
| 760 | N | ARG | A | 220 | -8.703 | 35.924 | 86.725 | 1.00 | 34.37 |
| 761 | CA | ARG | A | 220 | -7.506 | 36.322 | 87.508 | 1.00 | 36.06 |
| 762 | CB | ARG | A | 220 | -6.243 | 35.827 | 86.810 | 1.00 | 37.28 |
| 763 | CG | ARG | A | 220 | -5.058 | 35.372 | 87.750 | 1.00 | 44.07 |
| 764 | CD | ARG | A | 220 | -3.665 | 35.138 | 87.075 | 1.00 | 53.39 |
| 765 | NE | ARG | A | 220 | -3.131 | 36.401 | 86.587 | 1.00 | 57.56 |
| 766 | CZ | ARG | A | 220 | -3.067 | 36.736 | 85.300 | 1.00 | 63.45 |
| 767 | NH1 | ARG | A | 220 | -2.583 | 37.921 | 84.937 | 1.00 | 62.86 |
| 768 | NH2 | ARG | A | 220 | -3.473 | 35.882 | 84.365 | 1.00 | 65.24 |
| 769 | C | ARG | A | 220 | -7.561 | 37.846 | 87.621 | 1.00 | 35.84 |
| 770 | O | ARG | A | 220 | -7.328 | 38.467 | 88.683 | 1.00 | 34.61 |
| 771 | N | GLU | A | 221 | -7.928 | 38.427 | 86.490 | 1.00 | 35.98 |
| 772 | CA | GLU | A | 221 | -8.145 | 39.852 | 86.355 | 1.00 | 38.35 |
| 773 | CB | GLU | A | 221 | -8.573 | 40.154 | 84.930 | 1.00 | 39.07 |
| 774 | CG | GLU | A | 221 | -8.452 | 41.597 | 84.521 | 1.00 | 47.19 |
| 775 | CD | GLU | A | 221 | -7.205 | 42.221 | 85.080 | 1.00 | 57.25 |
| 776 | OE1 | GLU | A | 221 | -6.259 | 42.459 | 84.291 | 1.00 | 60.27 |
| 777 | OE2 | GLU | A | 221 | -7.178 | 42.474 | 86.314 | 1.00 | 62.91 |
| 778 | C | GLU | A | 221 | -9.149 | 40.339 | 87.416 | 1.00 | 38.74 |
| 779 | O | GLU | A | 221 | -8.832 | 41.307 | 88.117 | 1.00 | 38.67 |
| 780 | N | LEU | A | 222 | -10.296 | 39.663 | 87.575 | 1.00 | 37.69 |
| 781 | CA | LEU | A | 222 | -11.188 | 40.011 | 88.668 | 1.00 | 39.29 |
| 782 | CB | LEU | A | 222 | -12.513 | 39.256 | 88.615 | 1.00 | 40.21 |
| 783 | CG | LEU | A | 222 | -13.754 | 39.901 | 88.040 | 1.00 | 44.66 |
| 784 | CD1 | LEU | A | 222 | -13.892 | 41.386 | 88.378 | 1.00 | 44.76 |
| 785 | CD2 | LEU | A | 222 | -13.856 | 39.644 | 86.553 | 1.00 | 52.48 |
| 786 | C | LEU | A | 222 | -10.654 | 39.766 | 90.079 | 1.00 | 40.79 |
| 787 | O | LEU | A | 222 | -10.981 | 40.510 | 91.025 | 1.00 | 40.30 |
| 788 | N | GLN | A | 223 | -9.904 | 38.712 | 90.272 | 1.00 | 40.08 |
| 789 | CA | GLN | A | 223 | -9.456 | 38.509 | 91.612 | 1.00 | 43.39 |
| 790 | CB | GLN | A | 223 | -9.120 | 37.025 | 91.889 | 1.00 | 44.71 |
| 791 | CG | GLN | A | 223 | -7.754 | 36.535 | 91.538 | 1.00 | 49.87 |
| 792 | CD | GLN | A | 223 | -7.627 | 34.996 | 91.712 | 1.00 | 56.56 |
| 793 | OE1 | GLN | A | 223 | -6.942 | 34.309 | 90.918 | 1.00 | 58.11 |
| 794 | NE2 | GLN | A | 223 | -8.286 | 34.460 | 92.747 | 1.00 | 58.77 |
| 795 | C | GLN | A | 223 | -8.380 | 39.560 | 91.978 | 1.00 | 43.05 |
| 796 | O | GLN | A | 223 | -8.307 | 39.976 | 93.113 | 1.00 | 43.64 |
| 797 | N | LYS | A | 224 | -7.673 | 40.083 | 90.988 | 1.00 | 42.20 |
| 798 | CA | LYS | A | 224 | -6.690 | 41.126 | 91.203 | 1.00 | 42.99 |
| 799 | CB | LYS | A | 224 | -5.815 | 41.282 | 89.985 | 1.00 | 43.53 |
| 800 | CG | LYS | A | 224 | -4.818 | 42.422 | 90.066 | 1.00 | 48.88 |
| 801 | CD | LYS | A | 224 | -4.028 | 42.585 | 88.762 | 1.00 | 53.83 |
| 802 | CE | LYS | A | 224 | -4.857 | 43.218 | 87.650 | 1.00 | 57.23 |
| 803 | NZ | LYS | A | 224 | -4.028 | 43.546 | 86.442 | 1.00 | 60.62 |
| 804 | C | LYS | A | 224 | -7.356 | 42.461 | 91.560 | 1.00 | 43.04 |
| 805 | O | LYS | A | 224 | -7.042 | 43.032 | 92.599 | 1.00 | 42.77 |
| 806 | N | LEU | A | 225 | -8.297 | 42.913 | 90.732 | 1.00 | 40.83 |
| 807 | CA | LEU | A | 225 | -9.019 | 44.181 | 90.897 | 1.00 | 41.08 |

FIGURE 3P

| A | B | C | D | E | F | G | H | I | J |
|---|---|---|---|---|---|---|---|---|---|
| 808 | CB | LEU | A | 225 | -9.501 | 44.691 | 89.533 | 1.00 | 39.93 |
| 809 | CG | LEU | A | 225 | -8.469 | 45.241 | 88.540 | 1.00 | 43.97 |
| 810 | CD1 | LEU | A | 225 | -9.133 | 45.930 | 87.345 | 1.00 | 46.75 |
| 811 | CD2 | LEU | A | 225 | -7.332 | 46.154 | 89.189 | 1.00 | 43.17 |
| 812 | C | LEU | A | 225 | -10.254 | 44.157 | 91.818 | 1.00 | 40.68 |
| 813 | O | LEU | A | 225 | -10.784 | 45.218 | 92.182 | 1.00 | 40.10 |
| 814 | N | SER | A | 226 | -10.732 | 42.961 | 92.147 | 1.00 | 40.56 |
| 815 | CA | SER | A | 226 | -11.977 | 42.780 | 92.913 | 1.00 | 41.73 |
| 816 | CB | SER | A | 226 | -11.943 | 43.579 | 94.225 | 1.00 | 43.22 |
| 817 | OG | SER | A | 226 | -12.999 | 43.112 | 95.048 | 1.00 | 50.73 |
| 818 | C | SER | A | 226 | -13.295 | 43.050 | 92.126 | 1.00 | 40.15 |
| 819 | O | SER | A | 226 | -14.238 | 42.256 | 92.215 | 1.00 | 40.02 |
| 820 | N | LYS | A | 227 | -13.373 | 44.163 | 91.397 | 1.00 | 38.66 |
| 821 | CA | LYS | A | 227 | -14.500 | 44.424 | 90.506 | 1.00 | 38.28 |
| 822 | CB | LYS | A | 227 | -15.744 | 44.876 | 91.241 | 1.00 | 39.83 |
| 823 | CG | LYS | A | 227 | -15.527 | 46.112 | 92.107 | 1.00 | 43.19 |
| 824 | CD | LYS | A | 227 | -16.763 | 46.395 | 92.964 | 1.00 | 47.23 |
| 825 | CE | LYS | A | 227 | -17.009 | 47.898 | 93.037 | 1.00 | 50.59 |
| 826 | NZ | LYS | A | 227 | -15.847 | 48.527 | 93.755 | 1.00 | 50.07 |
| 827 | C | LYS | A | 227 | -14.057 | 45.437 | 89.453 | 1.00 | 37.32 |
| 828 | O | LYS | A | 227 | -13.032 | 46.114 | 89.637 | 1.00 | 35.43 |
| 829 | N | PHE | A | 228 | -14.784 | 45.541 | 88.339 | 1.00 | 34.98 |
| 830 | CA | PHE | A | 228 | -14.287 | 46.384 | 87.241 | 1.00 | 34.36 |
| 831 | CB | PHE | A | 228 | -14.483 | 45.686 | 85.908 | 1.00 | 32.60 |
| 832 | CG | PHE | A | 228 | -13.706 | 44.403 | 85.761 | 1.00 | 32.22 |
| 833 | CD1 | PHE | A | 228 | -12.556 | 44.214 | 86.480 | 1.00 | 30.96 |
| 834 | CE1 | PHE | A | 228 | -11.797 | 43.063 | 86.350 | 1.00 | 34.49 |
| 835 | CZ | PHE | A | 228 | -12.178 | 42.076 | 85.495 | 1.00 | 33.23 |
| 836 | CE2 | PHE | A | 228 | -13.374 | 42.246 | 84.752 | 1.00 | 34.03 |
| 837 | CD2 | PHE | A | 228 | -14.105 | 43.409 | 84.862 | 1.00 | 33.41 |
| 838 | C | PHE | A | 228 | -15.057 | 47.675 | 87.146 | 1.00 | 35.43 |
| 839 | O | PHE | A | 228 | -16.228 | 47.733 | 87.549 | 1.00 | 34.99 |
| 840 | N | ASP | A | 229 | -14.441 | 48.714 | 86.591 | 1.00 | 36.24 |
| 841 | CA | ASP | A | 229 | -15.233 | 49.943 | 86.453 | 1.00 | 38.49 |
| 842 | CB | ASP | A | 229 | -14.302 | 51.205 | 86.331 | 1.00 | 39.70 |
| 843 | CG | ASP | A | 229 | -13.484 | 51.241 | 85.072 | 1.00 | 44.65 |
| 844 | OD1 | ASP | A | 229 | -13.729 | 50.465 | 84.121 | 1.00 | 47.75 |
| 845 | OD2 | ASP | A | 229 | -12.527 | 52.046 | 84.948 | 1.00 | 52.81 |
| 846 | C | ASP | A | 229 | -16.211 | 49.721 | 85.300 | 1.00 | 37.35 |
| 847 | O | ASP | A | 229 | -16.187 | 48.669 | 84.633 | 1.00 | 35.10 |
| 848 | N | GLU | A | 230 | -17.038 | 50.715 | 85.027 | 1.00 | 37.87 |
| 849 | CA | GLU | A | 230 | -18.077 | 50.513 | 84.040 | 1.00 | 37.66 |
| 850 | CB | GLU | A | 230 | -19.054 | 51.668 | 84.115 | 1.00 | 39.25 |
| 851 | CG | GLU | A | 230 | -19.840 | 51.650 | 85.412 | 1.00 | 42.58 |
| 852 | CD | GLU | A | 230 | -21.045 | 52.566 | 85.320 | 1.00 | 49.54 |
| 853 | OE1 | GLU | A | 230 | -22.168 | 52.129 | 85.629 | 1.00 | 52.06 |
| 854 | OE2 | GLU | A | 230 | -20.868 | 53.740 | 84.896 | 1.00 | 52.95 |
| 855 | C | GLU | A | 230 | -17.483 | 50.440 | 82.659 | 1.00 | 36.98 |
| 856 | O | GLU | A | 230 | -18.015 | 49.782 | 81.767 | 1.00 | 34.19 |
| 857 | N | GLN | A | 231 | -16.382 | 51.159 | 82.461 | 1.00 | 36.82 |
| 858 | CA | GLN | A | 231 | -15.764 | 51.174 | 81.152 | 1.00 | 36.74 |

FIGURE 3Q

| A | B | C | D | E | F | G | H | I | J |
|---|---|---|---|---|---|---|---|---|---|
| 859 | CB | GLN | A | 231 | -14.587 | 52.171 | 81.128 | 1.00 | 37.55 |
| 860 | CG | GLN | A | 231 | -14.995 | 53.671 | 81.393 | 1.00 | 43.18 |
| 861 | CD | GLN | A | 231 | -16.011 | 53.956 | 82.522 | 1.00 | 46.32 |
| 862 | OE1 | GLN | A | 231 | -15.731 | 53.743 | 83.729 | 1.00 | 42.61 |
| 863 | NE2 | GLN | A | 231 | -17.181 | 54.488 | 82.121 | 1.00 | 47.58 |
| 864 | C | GLN | A | 231 | -15.212 | 49.784 | 80.817 | 1.00 | 35.85 |
| 865 | O | GLN | A | 231 | -15.382 | 49.294 | 79.724 | 1.00 | 36.28 |
| 866 | N | ARG | A | 232 | -14.495 | 49.186 | 81.746 | 1.00 | 33.62 |
| 867 | CA | ARG | A | 232 | -13.858 | 47.928 | 81.426 | 1.00 | 33.95 |
| 868 | CB | ARG | A | 232 | -12.832 | 47.530 | 82.509 | 1.00 | 33.54 |
| 869 | CG | ARG | A | 232 | -12.260 | 46.109 | 82.347 | 1.00 | 36.13 |
| 870 | CD | ARG | A | 232 | -11.433 | 45.610 | 83.520 | 1.00 | 40.91 |
| 871 | NE | ARG | A | 232 | -10.425 | 46.602 | 83.868 | 1.00 | 49.70 |
| 872 | CZ | ARG | A | 232 | -9.221 | 46.706 | 83.323 | 1.00 | 52.36 |
| 873 | NH1 | ARG | A | 232 | -8.817 | 45.862 | 82.371 | 1.00 | 53.98 |
| 874 | NH2 | ARG | A | 232 | -8.409 | 47.659 | 83.757 | 1.00 | 55.77 |
| 875 | C | ARG | A | 232 | -14.931 | 46.853 | 81.238 | 1.00 | 31.99 |
| 876 | O | ARG | A | 232 | -14.813 | 46.023 | 80.341 | 1.00 | 31.18 |
| 877 | N | THR | A | 233 | -15.971 | 46.890 | 82.072 | 1.00 | 30.75 |
| 878 | CA | THR | A | 233 | -17.071 | 45.931 | 82.002 | 1.00 | 30.48 |
| 879 | CB | THR | A | 233 | -18.080 | 46.242 | 83.085 | 1.00 | 31.41 |
| 880 | OG1 | THR | A | 233 | -17.464 | 45.953 | 84.337 | 1.00 | 28.31 |
| 881 | CG2 | THR | A | 233 | -19.358 | 45.267 | 82.986 | 1.00 | 28.26 |
| 882 | C | THR | A | 233 | -17.783 | 46.052 | 80.670 | 1.00 | 30.81 |
| 883 | O | THR | A | 233 | -17.937 | 45.050 | 79.937 | 1.00 | 29.48 |
| 884 | N | ALA | A | 234 | -18.283 | 47.261 | 80.402 | 1.00 | 30.12 |
| 885 | CA | ALA | A | 234 | -18.959 | 47.533 | 79.118 | 1.00 | 30.91 |
| 886 | CB | ALA | A | 234 | -19.319 | 48.998 | 78.963 | 1.00 | 29.68 |
| 887 | C | ALA | A | 234 | -18.104 | 47.102 | 77.946 | 1.00 | 30.58 |
| 888 | O | ALA | A | 234 | -18.611 | 46.555 | 76.947 | 1.00 | 31.37 |
| 889 | N | THR | A | 235 | -16.815 | 47.389 | 78.028 | 1.00 | 30.80 |
| 890 | CA | THR | A | 235 | -15.928 | 46.948 | 76.953 | 1.00 | 32.35 |
| 891 | CB | THR | A | 235 | -14.533 | 47.546 | 77.129 | 1.00 | 32.78 |
| 892 | OG1 | THR | A | 235 | -14.654 | 48.951 | 77.006 | 1.00 | 34.77 |
| 893 | CG2 | THR | A | 235 | -13.580 | 47.153 | 75.967 | 1.00 | 34.42 |
| 894 | C | THR | A | 235 | -15.860 | 45.400 | 76.799 | 1.00 | 32.27 |
| 895 | O | THR | A | 235 | -16.000 | 44.850 | 75.656 | 1.00 | 31.74 |
| 896 | N | TYR | A | 236 | -15.711 | 44.693 | 77.914 | 1.00 | 30.81 |
| 897 | CA | TYR | A | 236 | -15.676 | 43.199 | 77.861 | 1.00 | 29.77 |
| 898 | CB | TYR | A | 236 | -15.384 | 42.639 | 79.250 | 1.00 | 29.80 |
| 899 | CG | TYR | A | 236 | -13.950 | 42.738 | 79.720 | 1.00 | 32.58 |
| 900 | CD1 | TYR | A | 236 | -12.913 | 42.926 | 78.818 | 1.00 | 33.58 |
| 901 | CE1 | TYR | A | 236 | -11.617 | 42.996 | 79.243 | 1.00 | 36.97 |
| 902 | CZ | TYR | A | 236 | -11.324 | 42.872 | 80.601 | 1.00 | 36.77 |
| 903 | OH | TYR | A | 236 | -10.025 | 42.971 | 81.016 | 1.00 | 37.51 |
| 904 | CE2 | TYR | A | 236 | -12.330 | 42.686 | 81.516 | 1.00 | 35.78 |
| 905 | CD2 | TYR | A | 236 | -13.643 | 42.634 | 81.065 | 1.00 | 36.22 |
| 906 | C | TYR | A | 236 | -17.042 | 42.628 | 77.377 | 1.00 | 29.01 |
| 907 | O | TYR | A | 236 | -17.103 | 41.680 | 76.632 | 1.00 | 29.48 |
| 908 | N | ILE | A | 237 | -18.139 | 43.236 | 77.814 | 1.00 | 30.01 |
| 909 | CA | ILE | A | 237 | -19.472 | 42.788 | 77.378 | 1.00 | 30.81 |

FIGURE 3R

| A | B | C | D | E | F | G | H | I | J |
|---|---|---|---|---|---|---|---|---|---|
| 910 | CB | ILE | A | 237 | -20.591 | 43.548 | 78.061 | 1.00 | 29.26 |
| 911 | CG1 | ILE | A | 237 | -20.580 | 43.141 | 79.541 | 1.00 | 31.33 |
| 912 | CD1 | ILE | A | 237 | -20.607 | 41.494 | 79.786 | 1.00 | 32.72 |
| 913 | CG2 | ILE | A | 237 | -21.938 | 43.089 | 77.553 | 1.00 | 30.76 |
| 914 | C | ILE | A | 237 | -19.524 | 42.975 | 75.874 | 1.00 | 30.97 |
| 915 | O | ILE | A | 237 | -20.024 | 42.110 | 75.165 | 1.00 | 28.59 |
| 916 | N | THR | A | 238 | -19.071 | 44.126 | 75.413 | 1.00 | 29.66 |
| 917 | CA | THR | A | 238 | -19.074 | 44.331 | 73.936 | 1.00 | 31.58 |
| 918 | CB | THR | A | 238 | -18.483 | 45.699 | 73.600 | 1.00 | 30.71 |
| 919 | OG1 | THR | A | 238 | -19.345 | 46.681 | 74.169 | 1.00 | 33.26 |
| 920 | CG2 | THR | A | 238 | -18.547 | 45.948 | 72.092 | 1.00 | 36.01 |
| 921 | C | THR | A | 238 | -18.279 | 43.281 | 73.177 | 1.00 | 31.08 |
| 922 | O | THR | A | 238 | -18.744 | 42.785 | 72.179 | 1.00 | 31.90 |
| 923 | N | GLU | A | 239 | -17.037 | 43.029 | 73.578 | 1.00 | 30.93 |
| 924 | CA | GLU | A | 239 | -16.252 | 41.972 | 72.973 | 1.00 | 33.24 |
| 925 | CB | GLU | A | 239 | -14.875 | 41.829 | 73.619 | 1.00 | 34.28 |
| 926 | CG | GLU | A | 239 | -14.045 | 43.126 | 73.458 | 1.00 | 41.57 |
| 927 | CD | GLU | A | 239 | -12.704 | 43.109 | 74.200 | 1.00 | 50.78 |
| 928 | OE1 | GLU | A | 239 | -11.654 | 43.089 | 73.518 | 1.00 | 59.72 |
| 929 | OE2 | GLU | A | 239 | -12.655 | 43.120 | 75.451 | 1.00 | 51.19 |
| 930 | C | GLU | A | 239 | -16.947 | 40.625 | 72.977 | 1.00 | 32.47 |
| 931 | O | GLU | A | 239 | -16.890 | 39.912 | 72.000 | 1.00 | 31.96 |
| 932 | N | LEU | A | 240 | -17.585 | 40.307 | 74.093 | 1.00 | 31.66 |
| 933 | CA | LEU | A | 240 | -18.252 | 39.033 | 74.293 | 1.00 | 32.00 |
| 934 | CB | LEU | A | 240 | -18.793 | 38.941 | 75.749 | 1.00 | 32.28 |
| 935 | CG | LEU | A | 240 | -17.918 | 38.368 | 76.879 | 1.00 | 38.51 |
| 936 | CD1 | LEU | A | 240 | -17.987 | 39.156 | 78.226 | 1.00 | 40.94 |
| 937 | CD2 | LEU | A | 240 | -18.427 | 36.978 | 77.180 | 1.00 | 46.36 |
| 938 | C | LEU | A | 240 | -19.433 | 38.992 | 73.363 | 1.00 | 31.20 |
| 939 | O | LEU | A | 240 | -19.674 | 37.997 | 72.730 | 1.00 | 30.06 |
| 940 | N | ALA | A | 241 | -20.189 | 40.074 | 73.311 | 1.00 | 30.48 |
| 941 | CA | ALA | A | 241 | -21.385 | 40.079 | 72.470 | 1.00 | 30.85 |
| 942 | CB | ALA | A | 241 | -22.161 | 41.336 | 72.673 | 1.00 | 28.64 |
| 943 | C | ALA | A | 241 | -21.046 | 39.875 | 70.996 | 1.00 | 32.63 |
| 944 | O | ALA | A | 241 | -21.803 | 39.233 | 70.268 | 1.00 | 34.13 |
| 945 | N | ASN | A | 242 | -19.946 | 40.476 | 70.547 | 1.00 | 32.98 |
| 946 | CA | ASN | A | 242 | -19.501 | 40.301 | 69.176 | 1.00 | 34.79 |
| 947 | CB | ASN | A | 242 | -18.342 | 41.225 | 68.806 | 1.00 | 35.05 |
| 948 | CG | ASN | A | 242 | -18.735 | 42.668 | 68.801 | 1.00 | 37.46 |
| 949 | OD1 | ASN | A | 242 | -19.820 | 43.009 | 68.356 | 1.00 | 41.91 |
| 950 | ND2 | ASN | A | 242 | -17.838 | 43.531 | 69.270 | 1.00 | 36.72 |
| 951 | C | ASN | A | 242 | -19.045 | 38.878 | 68.944 | 1.00 | 33.66 |
| 952 | O | ASN | A | 242 | -19.384 | 38.322 | 67.926 | 1.00 | 34.14 |
| 953 | N | ALA | A | 243 | -18.284 | 38.287 | 69.871 | 1.00 | 33.13 |
| 954 | CA | ALA | A | 243 | -17.846 | 36.899 | 69.686 | 1.00 | 33.50 |
| 955 | CB | ALA | A | 243 | -16.883 | 36.413 | 70.821 | 1.00 | 32.46 |
| 956 | C | ALA | A | 243 | -19.100 | 36.026 | 69.596 | 1.00 | 33.00 |
| 957 | O | ALA | A | 243 | -19.170 | 35.121 | 68.775 | 1.00 | 34.04 |
| 958 | N | LEU | A | 244 | -20.063 | 36.281 | 70.460 | 1.00 | 32.30 |
| 959 | CA | LEU | A | 244 | -21.290 | 35.495 | 70.486 | 1.00 | 34.17 |
| 960 | CB | LEU | A | 244 | -22.109 | 35.794 | 71.761 | 1.00 | 32.72 |

FIGURE 3S

| A | B | C | D | E | F | G | H | I | J |
|---|---|---|---|---|---|---|---|---|---|
| 961 | CG | LEU | A | 244 | -21.487 | 35.248 | 73.091 | 1.00 | 33.90 |
| 962 | CD1 | LEU | A | 244 | -22.375 | 35.636 | 74.211 | 1.00 | 34.58 |
| 963 | CD2 | LEU | A | 244 | -21.346 | 33.731 | 73.053 | 1.00 | 36.04 |
| 964 | C | LEU | A | 244 | -22.155 | 35.710 | 69.239 | 1.00 | 35.07 |
| 965 | O | LEU | A | 244 | -22.795 | 34.770 | 68.771 | 1.00 | 35.54 |
| 966 | N | SER | A | 245 | -22.205 | 36.935 | 68.736 | 1.00 | 36.14 |
| 967 | CA | SER | A | 245 | -22.968 | 37.144 | 67.497 | 1.00 | 37.32 |
| 968 | CB | SER | A | 245 | -22.881 | 38.566 | 66.993 | 1.00 | 36.71 |
| 969 | OG | SER | A | 245 | -23.518 | 39.430 | 67.885 | 1.00 | 40.23 |
| 970 | C | SER | A | 245 | -22.396 | 36.244 | 66.430 | 1.00 | 37.77 |
| 971 | O | SER | A | 245 | -23.168 | 35.561 | 65.712 | 1.00 | 39.78 |
| 972 | N | TYR | A | 246 | -21.062 | 36.236 | 66.324 | 1.00 | 36.62 |
| 973 | CA | TYR | A | 246 | -20.388 | 35.397 | 65.334 | 1.00 | 36.75 |
| 974 | CB | TYR | A | 246 | -18.867 | 35.666 | 65.303 | 1.00 | 35.63 |
| 975 | CG | TYR | A | 246 | -18.040 | 34.768 | 64.415 | 1.00 | 36.74 |
| 976 | CD1 | TYR | A | 246 | -17.752 | 35.114 | 63.086 | 1.00 | 41.06 |
| 977 | CE1 | TYR | A | 246 | -16.991 | 34.283 | 62.293 | 1.00 | 40.63 |
| 978 | CZ | TYR | A | 246 | -16.491 | 33.118 | 62.824 | 1.00 | 42.34 |
| 979 | OH | TYR | A | 246 | -15.711 | 32.256 | 62.077 | 1.00 | 41.50 |
| 980 | CE2 | TYR | A | 246 | -16.782 | 32.766 | 64.151 | 1.00 | 40.05 |
| 981 | CD2 | TYR | A | 246 | -17.538 | 33.590 | 64.897 | 1.00 | 34.12 |
| 982 | C | TYR | A | 246 | -20.730 | 33.925 | 65.554 | 1.00 | 36.80 |
| 983 | O | TYR | A | 246 | -21.143 | 33.248 | 64.624 | 1.00 | 36.65 |
| 984 | N | CYS | A | 247 | -20.608 | 33.425 | 66.778 | 1.00 | 36.48 |
| 985 | CA | CYS | A | 247 | -21.015 | 32.049 | 67.085 | 1.00 | 36.90 |
| 986 | CB | CYS | A | 247 | -20.803 | 31.722 | 68.595 | 1.00 | 37.60 |
| 987 | SG | CYS | A | 247 | -19.067 | 31.666 | 69.093 | 1.00 | 42.84 |
| 988 | C | CYS | A | 247 | -22.473 | 31.711 | 66.758 | 1.00 | 37.39 |
| 989 | O | CYS | A | 247 | -22.746 | 30.672 | 66.121 | 1.00 | 37.58 |
| 990 | N | HIS | A | 248 | -23.400 | 32.529 | 67.256 | 1.00 | 36.67 |
| 991 | CA | HIS | A | 248 | -24.817 | 32.267 | 67.094 | 1.00 | 37.58 |
| 992 | CB | HIS | A | 248 | -25.698 | 33.244 | 67.876 | 1.00 | 37.99 |
| 993 | CG | HIS | A | 248 | -25.520 | 33.191 | 69.372 | 1.00 | 34.73 |
| 994 | ND1 | HIS | A | 248 | -26.053 | 34.149 | 70.204 | 1.00 | 36.33 |
| 995 | CE1 | HIS | A | 248 | -25.718 | 33.886 | 71.452 | 1.00 | 37.79 |
| 996 | NE2 | HIS | A | 248 | -24.957 | 32.807 | 71.458 | 1.00 | 33.84 |
| 997 | CD2 | HIS | A | 248 | -24.812 | 32.354 | 70.168 | 1.00 | 33.28 |
| 998 | C | HIS | A | 248 | -25.189 | 32.338 | 65.601 | 1.00 | 39.08 |
| 999 | O | HIS | A | 248 | -26.098 | 31.629 | 65.132 | 1.00 | 39.68 |
| 1000 | N | SER | A | 249 | -24.443 | 33.132 | 64.854 | 1.00 | 39.67 |
| 1001 | CA | SER | A | 249 | -24.748 | 33.244 | 63.437 | 1.00 | 41.50 |
| 1002 | CB | SER | A | 249 | -23.805 | 34.207 | 62.715 | 1.00 | 40.00 |
| 1003 | OG | SER | A | 249 | -22.561 | 33.599 | 62.481 | 1.00 | 41.00 |
| 1004 | C | SER | A | 249 | -24.644 | 31.857 | 62.870 | 1.00 | 42.73 |
| 1005 | O | SER | A | 249 | -25.312 | 31.550 | 61.894 | 1.00 | 43.62 |
| 1006 | N | LYS | A | 250 | -23.799 | 31.026 | 63.476 | 1.00 | 43.39 |
| 1007 | CA | LYS | A | 250 | -23.626 | 29.655 | 63.026 | 1.00 | 44.23 |
| 1008 | CB | LYS | A | 250 | -22.163 | 29.299 | 63.057 | 1.00 | 45.26 |
| 1009 | CG | LYS | A | 250 | -21.329 | 30.154 | 62.111 | 1.00 | 46.88 |
| 1010 | CD | LYS | A | 250 | -19.847 | 29.989 | 62.369 | 1.00 | 46.41 |
| 1011 | CE | LYS | A | 250 | -19.102 | 31.086 | 61.674 | 1.00 | 50.41 |

FIGURE 3T

| A | B | C | D | E | F | G | H | I | J |
|---|---|---|---|---|---|---|---|---|---|
| 1012 | NZ | LYS | A | 250 | -18.101 | 30.510 | 60.721 | 1.00 | 55.71 |
| 1013 | C | LYS | A | 250 | -24.430 | 28.706 | 63.912 | 1.00 | 44.23 |
| 1014 | O | LYS | A | 250 | -24.318 | 27.494 | 63.813 | 1.00 | 44.92 |
| 1015 | N | ARG | A | 251 | -25.252 | 29.280 | 64.771 | 1.00 | 43.03 |
| 1016 | CA | ARG | A | 251 | -26.013 | 28.499 | 65.722 | 1.00 | 43.09 |
| 1017 | CB | ARG | A | 251 | -27.003 | 27.566 | 65.025 | 1.00 | 44.17 |
| 1018 | CG | ARG | A | 251 | -28.079 | 28.334 | 64.298 | 1.00 | 48.00 |
| 1019 | CD | ARG | A | 251 | -29.293 | 28.613 | 65.135 | 1.00 | 52.94 |
| 1020 | NE | ARG | A | 251 | -30.316 | 27.613 | 64.935 | 1.00 | 57.46 |
| 1021 | CZ | ARG | A | 251 | -31.409 | 27.504 | 65.694 | 1.00 | 59.77 |
| 1022 | NH1 | ARG | A | 251 | -32.301 | 26.573 | 65.421 | 1.00 | 58.50 |
| 1023 | NH2 | ARG | A | 251 | -31.617 | 28.329 | 66.721 | 1.00 | 60.29 |
| 1024 | C | ARG | A | 251 | -25.133 | 27.719 | 66.694 | 1.00 | 40.87 |
| 1025 | O | ARG | A | 251 | -25.579 | 26.725 | 67.287 | 1.00 | 41.62 |
| 1026 | N | VAL | A | 252 | -23.890 | 28.136 | 66.866 | 1.00 | 38.05 |
| 1027 | CA | VAL | A | 252 | -23.090 | 27.469 | 67.883 | 1.00 | 35.63 |
| 1028 | CB | VAL | A | 252 | -21.605 | 27.579 | 67.574 | 1.00 | 36.71 |
| 1029 | CG1 | VAL | A | 252 | -20.757 | 27.253 | 68.833 | 1.00 | 36.16 |
| 1030 | CG2 | VAL | A | 252 | -21.267 | 26.671 | 66.408 | 1.00 | 32.96 |
| 1031 | C | VAL | A | 252 | -23.398 | 28.171 | 69.217 | 1.00 | 35.05 |
| 1032 | O | VAL | A | 252 | -23.342 | 29.421 | 69.278 | 1.00 | 34.28 |
| 1033 | N | ILE | A | 253 | -23.751 | 27.394 | 70.238 | 1.00 | 34.78 |
| 1034 | CA | ILE | A | 253 | -24.036 | 27.990 | 71.537 | 1.00 | 34.21 |
| 1035 | CB | ILE | A | 253 | -25.528 | 27.772 | 72.035 | 1.00 | 36.92 |
| 1036 | CG1 | ILE | A | 253 | -26.008 | 26.317 | 72.080 | 1.00 | 34.92 |
| 1037 | CD1 | ILE | A | 253 | -27.473 | 26.046 | 72.506 | 1.00 | 33.07 |
| 1038 | CG2 | ILE | A | 253 | -26.490 | 28.538 | 71.085 | 1.00 | 39.25 |
| 1039 | C | ILE | A | 253 | -22.899 | 27.570 | 72.441 | 1.00 | 32.53 |
| 1040 | O | ILE | A | 253 | -22.459 | 26.397 | 72.378 | 1.00 | 32.33 |
| 1041 | N | HIS | A | 254 | -22.352 | 28.508 | 73.234 | 1.00 | 30.81 |
| 1042 | CA | HIS | A | 254 | -21.118 | 28.158 | 73.987 | 1.00 | 29.80 |
| 1043 | CB | HIS | A | 254 | -20.268 | 29.410 | 74.275 | 1.00 | 29.82 |
| 1044 | CG | HIS | A | 254 | -19.012 | 29.095 | 75.010 | 1.00 | 27.09 |
| 1045 | ND1 | HIS | A | 254 | -19.012 | 28.695 | 76.327 | 1.00 | 28.08 |
| 1046 | CE1 | HIS | A | 254 | -17.763 | 28.515 | 76.729 | 1.00 | 29.12 |
| 1047 | NE2 | HIS | A | 254 | -16.960 | 28.776 | 75.712 | 1.00 | 31.85 |
| 1048 | CD2 | HIS | A | 254 | -17.712 | 29.137 | 74.622 | 1.00 | 26.39 |
| 1049 | C | HIS | A | 254 | -21.449 | 27.412 | 75.287 | 1.00 | 29.59 |
| 1050 | O | HIS | A | 254 | -20.897 | 26.345 | 75.563 | 1.00 | 28.85 |
| 1051 | N | ARG | A | 255 | -22.405 | 27.957 | 76.024 | 1.00 | 30.83 |
| 1052 | CA | ARG | A | 255 | -22.920 | 27.309 | 77.234 | 1.00 | 30.64 |
| 1053 | CB | ARG | A | 255 | -23.388 | 25.859 | 76.916 | 1.00 | 30.22 |
| 1054 | CG | ARG | A | 255 | -24.321 | 25.716 | 75.687 | 1.00 | 32.25 |
| 1055 | CD | ARG | A | 255 | -25.189 | 24.432 | 75.685 | 1.00 | 31.75 |
| 1056 | NE | ARG | A | 255 | -24.362 | 23.256 | 75.649 | 1.00 | 30.77 |
| 1057 | CZ | ARG | A | 255 | -24.820 | 22.017 | 75.669 | 1.00 | 31.35 |
| 1058 | NH1 | ARG | A | 255 | -26.095 | 21.798 | 75.751 | 1.00 | 31.83 |
| 1059 | NH2 | ARG | A | 255 | -23.977 | 21.003 | 75.617 | 1.00 | 33.16 |
| 1060 | C | ARG | A | 255 | -21.983 | 27.279 | 78.449 | 1.00 | 31.38 |
| 1061 | O | ARG | A | 255 | -22.363 | 26.734 | 79.477 | 1.00 | 32.65 |
| 1062 | N | ASP | A | 256 | -20.758 | 27.768 | 78.356 | 1.00 | 31.39 |

FIGURE 3U

| A | B | C | D | E | F | G | H | I | J |
|---|---|---|---|---|---|---|---|---|---|
| 1063 | CA | ASP | A | 256 | -19.870 | 27.725 | 79.524 | 1.00 | 31.75 |
| 1064 | CB | ASP | A | 256 | -18.964 | 26.468 | 79.453 | 1.00 | 33.11 |
| 1065 | CG | ASP | A | 256 | -18.280 | 26.139 | 80.746 | 1.00 | 35.07 |
| 1066 | OD1 | ASP | A | 256 | -18.773 | 26.510 | 81.850 | 1.00 | 40.12 |
| 1067 | OD2 | ASP | A | 256 | -17.221 | 25.488 | 80.765 | 1.00 | 36.02 |
| 1068 | C | ASP | A | 256 | -19.086 | 29.003 | 79.566 | 1.00 | 31.14 |
| 1069 | O | ASP | A | 256 | -17.867 | 29.025 | 79.770 | 1.00 | 30.07 |
| 1070 | N | ILE | A | 257 | -19.785 | 30.091 | 79.314 | 1.00 | 29.90 |
| 1071 | CA | ILE | A | 257 | -19.166 | 31.390 | 79.385 | 1.00 | 32.07 |
| 1072 | CB | ILE | A | 257 | -20.057 | 32.311 | 78.676 | 1.00 | 32.32 |
| 1073 | CG1 | ILE | A | 257 | -19.935 | 31.982 | 77.143 | 1.00 | 33.96 |
| 1074 | CD1 | ILE | A | 257 | -21.111 | 32.476 | 76.377 | 1.00 | 40.55 |
| 1075 | CG2 | ILE | A | 257 | -19.737 | 33.701 | 78.956 | 1.00 | 34.18 |
| 1076 | C | ILE | A | 257 | -19.064 | 31.704 | 80.897 | 1.00 | 33.31 |
| 1077 | O | ILE | A | 257 | -20.100 | 31.754 | 81.616 | 1.00 | 34.68 |
| 1078 | N | LYS | A | 258 | -17.824 | 31.761 | 81.371 | 1.00 | 31.48 |
| 1079 | CA | LYS | A | 258 | -17.519 | 32.187 | 82.750 | 1.00 | 30.84 |
| 1080 | CB | LYS | A | 258 | -17.738 | 31.082 | 83.740 | 1.00 | 30.14 |
| 1081 | CG | LYS | A | 258 | -16.926 | 29.870 | 83.529 | 1.00 | 34.40 |
| 1082 | CD | LYS | A | 258 | -17.629 | 28.644 | 84.283 | 1.00 | 38.03 |
| 1083 | CE | LYS | A | 258 | -16.742 | 27.431 | 84.270 | 1.00 | 41.53 |
| 1084 | NZ | LYS | A | 258 | -17.580 | 26.165 | 84.236 | 1.00 | 42.89 |
| 1085 | C | LYS | A | 258 | -16.097 | 32.737 | 82.755 | 1.00 | 30.04 |
| 1086 | O | LYS | A | 258 | -15.324 | 32.537 | 81.785 | 1.00 | 26.95 |
| 1087 | N | PRO | A | 259 | -15.775 | 33.505 | 83.792 | 1.00 | 28.33 |
| 1088 | CA | PRO | A | 259 | -14.498 | 34.201 | 83.824 | 1.00 | 28.63 |
| 1089 | CB | PRO | A | 259 | -14.480 | 34.892 | 85.200 | 1.00 | 27.18 |
| 1090 | CG | PRO | A | 259 | -15.974 | 35.164 | 85.421 | 1.00 | 28.54 |
| 1091 | CD | PRO | A | 259 | -16.648 | 33.843 | 84.942 | 1.00 | 29.43 |
| 1092 | C | PRO | A | 259 | -13.330 | 33.301 | 83.615 | 1.00 | 27.22 |
| 1093 | O | PRO | A | 259 | -12.411 | 33.740 | 82.963 | 1.00 | 28.73 |
| 1094 | N | GLU | A | 260 | -13.331 | 32.086 | 84.121 | 1.00 | 27.82 |
| 1095 | CA | GLU | A | 260 | -12.176 | 31.226 | 83.876 | 1.00 | 28.92 |
| 1096 | CB | GLU | A | 260 | -12.107 | 30.028 | 84.836 | 1.00 | 31.10 |
| 1097 | CG | GLU | A | 260 | -13.445 | 29.310 | 84.935 | 1.00 | 35.20 |
| 1098 | CD | GLU | A | 260 | -14.340 | 29.861 | 86.098 | 1.00 | 44.01 |
| 1099 | OE1 | GLU | A | 260 | -14.462 | 29.148 | 87.133 | 1.00 | 49.68 |
| 1100 | OE2 | GLU | A | 260 | -14.908 | 30.985 | 86.003 | 1.00 | 33.54 |
| 1101 | C | GLU | A | 260 | -12.027 | 30.755 | 82.420 | 1.00 | 28.10 |
| 1102 | O | GLU | A | 260 | -10.957 | 30.265 | 82.068 | 1.00 | 29.64 |
| 1103 | N | ASN | A | 261 | -13.012 | 30.991 | 81.567 | 1.00 | 26.88 |
| 1104 | CA | ASN | A | 261 | -12.871 | 30.603 | 80.189 | 1.00 | 26.98 |
| 1105 | CB | ASN | A | 261 | -14.077 | 29.731 | 79.753 | 1.00 | 26.91 |
| 1106 | CG | ASN | A | 261 | -14.099 | 28.389 | 80.436 | 1.00 | 26.82 |
| 1107 | OD1 | ASN | A | 261 | -13.048 | 27.832 | 80.771 | 1.00 | 28.36 |
| 1108 | ND2 | ASN | A | 261 | -15.322 | 27.808 | 80.578 | 1.00 | 25.54 |
| 1109 | C | ASN | A | 261 | -12.786 | 31.829 | 79.266 | 1.00 | 28.17 |
| 1110 | O | ASN | A | 261 | -12.988 | 31.685 | 78.040 | 1.00 | 28.42 |
| 1111 | N | LEU | A | 262 | -12.540 | 33.021 | 79.848 | 1.00 | 27.97 |
| 1112 | CA | LEU | A | 262 | -12.454 | 34.254 | 79.091 | 1.00 | 28.33 |
| 1113 | CB | LEU | A | 262 | -13.351 | 35.341 | 79.662 | 1.00 | 29.50 |

FIGURE 3V

| A | B | C | D | E | F | G | H | I | J |
|---|---|---|---|---|---|---|---|---|---|
| 1114 | CG | LEU | A | 262 | -14.856 | 35.024 | 79.655 | 1.00 | 28.47 |
| 1115 | CD1 | LEU | A | 262 | -15.646 | 36.167 | 80.215 | 1.00 | 30.27 |
| 1116 | CD2 | LEU | A | 262 | -15.308 | 34.782 | 78.142 | 1.00 | 27.13 |
| 1117 | C | LEU | A | 262 | -11.011 | 34.681 | 79.268 | 1.00 | 29.16 |
| 1118 | O | LEU | A | 262 | -10.554 | 34.891 | 80.405 | 1.00 | 28.97 |
| 1119 | N | LEU | A | 263 | -10.299 | 34.765 | 78.163 | 1.00 | 26.56 |
| 1120 | CA | LEU | A | 263 | -8.869 | 34.988 | 78.194 | 1.00 | 28.18 |
| 1121 | CB | LEU | A | 263 | -8.103 | 33.942 | 77.360 | 1.00 | 26.68 |
| 1122 | CG | LEU | A | 263 | -8.452 | 32.452 | 77.583 | 1.00 | 29.56 |
| 1123 | CD1 | LEU | A | 263 | -7.487 | 31.481 | 76.825 | 1.00 | 30.33 |
| 1124 | CD2 | LEU | A | 263 | -8.272 | 32.171 | 79.060 | 1.00 | 34.69 |
| 1125 | C | LEU | A | 263 | -8.574 | 36.382 | 77.619 | 1.00 | 29.97 |
| 1126 | O | LEU | A | 263 | -9.416 | 37.002 | 76.966 | 1.00 | 29.84 |
| 1127 | N | LEU | A | 264 | -7.378 | 36.850 | 77.904 | 1.00 | 30.85 |
| 1128 | CA | LEU | A | 264 | -6.951 | 38.182 | 77.486 | 1.00 | 30.74 |
| 1129 | CB | LEU | A | 264 | -6.721 | 39.079 | 78.732 | 1.00 | 30.19 |
| 1130 | CG | LEU | A | 264 | -7.965 | 39.287 | 79.626 | 1.00 | 30.14 |
| 1131 | CD1 | LEU | A | 264 | -7.590 | 39.909 | 81.031 | 1.00 | 32.30 |
| 1132 | CD2 | LEU | A | 264 | -9.105 | 40.109 | 78.954 | 1.00 | 31.52 |
| 1133 | C | LEU | A | 264 | -5.737 | 38.121 | 76.554 | 1.00 | 30.62 |
| 1134 | O | LEU | A | 264 | -4.722 | 37.498 | 76.853 | 1.00 | 29.43 |
| 1135 | N | GLY | A | 265 | -5.901 | 38.736 | 75.390 | 1.00 | 31.75 |
| 1136 | CA | GLY | A | 265 | -4.858 | 38.816 | 74.396 | 1.00 | 33.01 |
| 1137 | C | GLY | A | 265 | -3.830 | 39.883 | 74.737 | 1.00 | 34.94 |
| 1138 | O | GLY | A | 265 | -3.969 | 40.574 | 75.751 | 1.00 | 34.96 |
| 1139 | N | SER | A | 266 | -2.807 | 40.035 | 73.891 | 1.00 | 36.48 |
| 1140 | CA | SER | A | 266 | -1.722 | 40.978 | 74.178 | 1.00 | 39.30 |
| 1141 | CB | SER | A | 266 | -0.547 | 40.820 | 73.179 | 1.00 | 39.61 |
| 1142 | OG | SER | A | 266 | -1.009 | 40.865 | 71.841 | 1.00 | 45.24 |
| 1143 | C | SER | A | 266 | -2.195 | 42.443 | 74.287 | 1.00 | 39.68 |
| 1144 | O | SER | A | 266 | -1.591 | 43.221 | 74.989 | 1.00 | 41.74 |
| 1145 | N | ALA | A | 267 | -3.286 | 42.827 | 73.641 | 1.00 | 39.84 |
| 1146 | CA | ALA | A | 267 | -3.757 | 44.193 | 73.821 | 1.00 | 40.82 |
| 1147 | CB | ALA | A | 267 | -4.312 | 44.745 | 72.510 | 1.00 | 41.57 |
| 1148 | C | ALA | A | 267 | -4.826 | 44.245 | 74.881 | 1.00 | 40.28 |
| 1149 | O | ALA | A | 267 | -5.507 | 45.246 | 75.017 | 1.00 | 41.69 |
| 1150 | N | GLY | A | 268 | -4.999 | 43.160 | 75.616 | 1.00 | 38.92 |
| 1151 | CA | GLY | A | 268 | -6.066 | 43.099 | 76.605 | 1.00 | 39.91 |
| 1152 | C | GLY | A | 268 | -7.440 | 42.772 | 76.035 | 1.00 | 39.16 |
| 1153 | O | GLY | A | 268 | -8.421 | 42.894 | 76.749 | 1.00 | 39.70 |
| 1154 | N | GLU | A | 269 | -7.525 | 42.328 | 74.781 | 1.00 | 37.55 |
| 1155 | CA | GLU | A | 269 | -8.846 | 42.066 | 74.210 | 1.00 | 37.18 |
| 1156 | CB | GLU | A | 269 | -8.844 | 42.024 | 72.686 | 1.00 | 36.91 |
| 1157 | CG | GLU | A | 269 | -7.914 | 40.966 | 72.111 | 1.00 | 42.45 |
| 1158 | CD | GLU | A | 269 | -6.497 | 41.495 | 71.931 | 1.00 | 48.18 |
| 1159 | OE1 | GLU | A | 269 | -5.789 | 41.696 | 72.951 | 1.00 | 49.56 |
| 1160 | OE2 | GLU | A | 269 | -6.122 | 41.758 | 70.767 | 1.00 | 54.50 |
| 1161 | C | GLU | A | 269 | -9.323 | 40.711 | 74.736 | 1.00 | 34.23 |
| 1162 | O | GLU | A | 269 | -8.556 | 39.821 | 74.981 | 1.00 | 32.16 |
| 1163 | N | LEU | A | 270 | -10.611 | 40.599 | 74.889 | 1.00 | 33.25 |
| 1164 | CA | LEU | A | 270 | -11.188 | 39.438 | 75.496 | 1.00 | 33.59 |

FIGURE 3W

| A | B | C | D | E | F | G | H | I | J |
|---|---|---|---|---|---|---|---|---|---|
| 1165 | CB | LEU | A | 270 | -12.532 | 39.836 | 76.065 | 1.00 | 33.76 |
| 1166 | CG | LEU | A | 270 | -13.339 | 38.735 | 76.759 | 1.00 | 35.55 |
| 1167 | CD1 | LEU | A | 270 | -14.388 | 39.362 | 77.722 | 1.00 | 38.75 |
| 1168 | CD2 | LEU | A | 270 | -14.078 | 37.912 | 75.720 | 1.00 | 35.40 |
| 1169 | C | LEU | A | 270 | -11.330 | 38.372 | 74.432 | 1.00 | 33.86 |
| 1170 | O | LEU | A | 270 | -11.671 | 38.675 | 73.243 | 1.00 | 34.74 |
| 1171 | N | LYS | A | 271 | -11.099 | 37.133 | 74.834 | 1.00 | 31.42 |
| 1172 | CA | LYS | A | 271 | -11.191 | 35.979 | 73.930 | 1.00 | 31.29 |
| 1173 | CB | LYS | A | 271 | -9.795 | 35.492 | 73.555 | 1.00 | 31.80 |
| 1174 | CG | LYS | A | 271 | -9.128 | 36.524 | 72.537 | 1.00 | 35.49 |
| 1175 | CD | LYS | A | 271 | -7.766 | 36.110 | 72.033 | 1.00 | 38.66 |
| 1176 | CE | LYS | A | 271 | -7.165 | 37.192 | 71.120 | 1.00 | 39.08 |
| 1177 | NZ | LYS | A | 271 | -7.494 | 36.998 | 69.682 | 1.00 | 42.36 |
| 1178 | C | LYS | A | 271 | -11.994 | 34.844 | 74.605 | 1.00 | 29.90 |
| 1179 | O | LYS | A | 271 | -11.668 | 34.417 | 75.687 | 1.00 | 30.82 |
| 1180 | N | ILE | A | 272 | -13.062 | 34.408 | 73.997 | 1.00 | 29.63 |
| 1181 | CA | ILE | A | 272 | -13.770 | 33.287 | 74.572 | 1.00 | 31.28 |
| 1182 | CB | ILE | A | 272 | -15.251 | 33.238 | 74.154 | 1.00 | 32.97 |
| 1183 | CG1 | ILE | A | 272 | -15.867 | 31.943 | 74.660 | 1.00 | 34.14 |
| 1184 | CD1 | ILE | A | 272 | -17.133 | 32.166 | 75.428 | 1.00 | 41.15 |
| 1185 | CG2 | ILE | A | 272 | -15.415 | 33.105 | 72.693 | 1.00 | 36.72 |
| 1186 | C | ILE | A | 272 | -12.981 | 32.023 | 74.227 | 1.00 | 29.77 |
| 1187 | O | ILE | A | 272 | -12.487 | 31.888 | 73.131 | 1.00 | 29.32 |
| 1188 | N | ALA | A | 273 | -12.833 | 31.121 | 75.199 | 1.00 | 29.03 |
| 1189 | CA | ALA | A | 273 | -12.072 | 29.905 | 75.040 | 1.00 | 28.02 |
| 1190 | CB | ALA | A | 273 | -10.720 | 30.027 | 75.796 | 1.00 | 25.93 |
| 1191 | C | ALA | A | 273 | -12.890 | 28.757 | 75.639 | 1.00 | 28.47 |
| 1192 | O | ALA | A | 273 | -14.008 | 28.975 | 76.165 | 1.00 | 29.27 |
| 1193 | N | ASP | A | 274 | -12.329 | 27.558 | 75.567 | 1.00 | 28.32 |
| 1194 | CA | ASP | A | 274 | -12.900 | 26.361 | 76.217 | 1.00 | 30.13 |
| 1195 | CB | ASP | A | 274 | -12.994 | 26.548 | 77.752 | 1.00 | 28.19 |
| 1196 | CG | ASP | A | 274 | -13.273 | 25.239 | 78.444 | 1.00 | 30.91 |
| 1197 | OD1 | ASP | A | 274 | -13.354 | 25.219 | 79.681 | 1.00 | 27.79 |
| 1198 | OD2 | ASP | A | 274 | -13.407 | 24.145 | 77.794 | 1.00 | 33.55 |
| 1199 | C | ASP | A | 274 | -14.278 | 25.977 | 75.649 | 1.00 | 29.52 |
| 1200 | O | ASP | A | 274 | -15.326 | 26.170 | 76.275 | 1.00 | 28.76 |
| 1201 | N | PHE | A | 275 | -14.288 | 25.489 | 74.427 | 1.00 | 29.79 |
| 1202 | CA | PHE | A | 275 | -15.564 | 25.206 | 73.796 | 1.00 | 31.48 |
| 1203 | CB | PHE | A | 275 | -15.508 | 25.464 | 72.250 | 1.00 | 30.13 |
| 1204 | CG | PHE | A | 275 | -15.621 | 26.887 | 71.890 | 1.00 | 30.02 |
| 1205 | CD1 | PHE | A | 275 | -14.605 | 27.761 | 72.243 | 1.00 | 30.82 |
| 1206 | CE1 | PHE | A | 275 | -14.705 | 29.121 | 71.908 | 1.00 | 31.65 |
| 1207 | CZ | PHE | A | 275 | -15.847 | 29.599 | 71.217 | 1.00 | 30.66 |
| 1208 | CE2 | PHE | A | 275 | -16.846 | 28.718 | 70.853 | 1.00 | 28.29 |
| 1209 | CD2 | PHE | A | 275 | -16.707 | 27.356 | 71.175 | 1.00 | 28.74 |
| 1210 | C | PHE | A | 275 | -16.042 | 23.793 | 74.019 | 1.00 | 31.32 |
| 1211 | O | PHE | A | 275 | -16.874 | 23.333 | 73.263 | 1.00 | 33.58 |
| 1212 | N | GLY | A | 276 | -15.542 | 23.128 | 75.050 | 1.00 | 32.57 |
| 1213 | CA | GLY | A | 276 | -15.980 | 21.764 | 75.409 | 1.00 | 33.27 |
| 1214 | C | GLY | A | 276 | -17.470 | 21.591 | 75.718 | 1.00 | 33.63 |
| 1215 | O | GLY | A | 276 | -18.005 | 20.503 | 75.585 | 1.00 | 35.45 |

FIGURE 3X

| A | B | C | D | E | F | G | H | I | J |
|---|---|---|---|---|---|---|---|---|---|
| 1216 | N | TRP | A | 277 | -18.168 | 22.649 | 76.085 | 1.00 | 32.48 |
| 1217 | CA | TRP | A | 277 | -19.590 | 22.515 | 76.352 | 1.00 | 32.61 |
| 1218 | CB | TRP | A | 277 | -19.996 | 23.356 | 77.571 | 1.00 | 31.90 |
| 1219 | CG | TRP | A | 277 | -19.872 | 22.560 | 78.827 | 1.00 | 33.69 |
| 1220 | CD1 | TRP | A | 277 | -18.906 | 22.655 | 79.755 | 1.00 | 35.79 |
| 1221 | NE1 | TRP | A | 277 | -19.139 | 21.779 | 80.781 | 1.00 | 39.83 |
| 1222 | CE2 | TRP | A | 277 | -20.287 | 21.083 | 80.520 | 1.00 | 39.15 |
| 1223 | CD2 | TRP | A | 277 | -20.784 | 21.563 | 79.295 | 1.00 | 36.18 |
| 1224 | CE3 | TRP | A | 277 | -21.976 | 21.021 | 78.795 | 1.00 | 37.42 |
| 1225 | CZ3 | TRP | A | 277 | -22.625 | 19.991 | 79.531 | 1.00 | 40.23 |
| 1226 | CH2 | TRP | A | 277 | -22.103 | 19.550 | 80.772 | 1.00 | 36.38 |
| 1227 | CZ2 | TRP | A | 277 | -20.945 | 20.080 | 81.281 | 1.00 | 39.03 |
| 1228 | C | TRP | A | 277 | -20.375 | 22.965 | 75.141 | 1.00 | 31.77 |
| 1229 | O | TRP | A | 277 | -21.575 | 22.921 | 75.138 | 1.00 | 31.92 |
| 1230 | N | SER | A | 278 | -19.701 | 23.425 | 74.102 | 1.00 | 30.59 |
| 1231 | CA | SER | A | 278 | -20.489 | 23.978 | 73.041 | 1.00 | 32.01 |
| 1232 | CB | SER | A | 278 | -19.643 | 24.889 | 72.181 | 1.00 | 32.28 |
| 1233 | OG | SER | A | 278 | -18.600 | 24.165 | 71.545 | 1.00 | 37.30 |
| 1234 | C | SER | A | 278 | -21.253 | 22.892 | 72.194 | 1.00 | 33.25 |
| 1235 | O | SER | A | 278 | -20.861 | 21.734 | 72.149 | 1.00 | 34.86 |
| 1236 | N | VAL | A | 279 | -22.353 | 23.307 | 71.560 | 1.00 | 34.55 |
| 1237 | CA | VAL | A | 279 | -23.201 | 22.424 | 70.775 | 1.00 | 36.63 |
| 1238 | CB | VAL | A | 279 | -24.238 | 21.763 | 71.710 | 1.00 | 36.03 |
| 1239 | CG1 | VAL | A | 279 | -25.173 | 22.788 | 72.273 | 1.00 | 35.73 |
| 1240 | CG2 | VAL | A | 279 | -24.920 | 20.585 | 71.018 | 1.00 | 38.77 |
| 1241 | C | VAL | A | 279 | -23.873 | 23.260 | 69.702 | 1.00 | 36.61 |
| 1242 | O | VAL | A | 279 | -23.927 | 24.488 | 69.850 | 1.00 | 35.60 |
| 1243 | N | HIS | A | 280 | -24.438 | 22.679 | 68.636 | 1.00 | 37.41 |
| 1244 | CA | HIS | A | 280 | -25.231 | 23.526 | 67.764 | 1.00 | 37.57 |
| 1245 | CB | HIS | A | 280 | -25.245 | 22.996 | 66.333 | 1.00 | 39.08 |
| 1246 | CG | HIS | A | 280 | -23.897 | 23.025 | 65.714 | 1.00 | 39.44 |
| 1247 | ND1 | HIS | A | 280 | -23.001 | 21.988 | 65.841 | 1.00 | 45.81 |
| 1248 | CE1 | HIS | A | 280 | -21.883 | 22.296 | 65.203 | 1.00 | 45.95 |
| 1249 | NE2 | HIS | A | 280 | -22.028 | 23.493 | 64.660 | 1.00 | 46.60 |
| 1250 | CD2 | HIS | A | 280 | -23.283 | 23.969 | 64.964 | 1.00 | 45.31 |
| 1251 | C | HIS | A | 280 | -26.590 | 23.569 | 68.343 | 1.00 | 37.33 |
| 1252 | O | HIS | A | 280 | -27.040 | 22.566 | 68.911 | 1.00 | 37.60 |
| 1253 | N | ALA | A | 281 | -27.212 | 24.737 | 68.237 | 1.00 | 36.55 |
| 1254 | CA | ALA | A | 281 | -28.494 | 25.000 | 68.825 | 1.00 | 38.46 |
| 1255 | CB | ALA | A | 281 | -28.828 | 26.461 | 68.875 | 1.00 | 37.40 |
| 1256 | C | ALA | A | 281 | -29.597 | 24.175 | 68.213 | 1.00 | 41.55 |
| 1257 | O | ALA | A | 281 | -29.485 | 23.958 | 67.009 | 1.00 | 41.26 |
| 1258 | N | PRO | A | 282 | -30.764 | 24.290 | 68.822 | 1.00 | 41.87 |
| 1259 | CA | PRO | A | 282 | -31.606 | 23.344 | 69.535 | 1.00 | 41.68 |
| 1260 | CB | PRO | A | 282 | -32.618 | 22.859 | 68.482 | 1.00 | 42.55 |
| 1261 | CG | PRO | A | 282 | -32.233 | 23.675 | 67.281 | 1.00 | 41.31 |
| 1262 | CD | PRO | A | 282 | -31.631 | 25.026 | 67.910 | 1.00 | 44.02 |
| 1263 | C | PRO | A | 282 | -30.712 | 22.264 | 70.155 | 1.00 | 40.86 |
| 1264 | O | PRO | A | 282 | -30.004 | 21.537 | 69.457 | 1.00 | 40.78 |
| 1265 | N | SER | A | 283 | -30.704 | 22.233 | 71.483 | 1.00 | 38.89 |
| 1266 | CA | SER | A | 283 | -30.011 | 21.158 | 72.148 | 1.00 | 39.04 |

FIGURE 3Y

| A | B | C | D | E | F | G | H | I | J |
|---|---|---|---|---|---|---|---|---|---|
| 1267 | CB | SER | A | 283 | -28.515 | 21.411 | 72.222 | 1.00 | 38.52 |
| 1268 | OG | SER | A | 283 | -27.832 | 20.358 | 72.915 | 1.00 | 40.61 |
| 1269 | C | SER | A | 283 | -30.549 | 20.857 | 73.526 | 1.00 | 39.37 |
| 1270 | O | SER | A | 283 | -31.163 | 21.706 | 74.190 | 1.00 | 39.84 |
| 1271 | N | SER | A | 284 | -30.310 | 19.641 | 73.955 | 1.00 | 39.43 |
| 1272 | CA | SER | A | 284 | -30.584 | 19.299 | 75.314 | 1.00 | 41.76 |
| 1273 | CB | SER | A | 284 | -31.245 | 17.940 | 75.356 | 1.00 | 43.22 |
| 1274 | OG | SER | A | 284 | -32.242 | 17.954 | 76.372 | 1.00 | 47.58 |
| 1275 | C | SER | A | 284 | -29.239 | 19.218 | 75.979 | 1.00 | 42.43 |
| 1276 | O | SER | A | 284 | -28.205 | 19.677 | 75.432 | 1.00 | 43.18 |
| 1277 | N | ARG | A | 285 | -29.226 | 18.626 | 77.161 | 1.00 | 42.91 |
| 1278 | CA | ARG | A | 285 | -27.980 | 18.390 | 77.875 | 1.00 | 43.85 |
| 1279 | CB | ARG | A | 285 | -27.914 | 19.247 | 79.145 | 1.00 | 43.75 |
| 1280 | CG | ARG | A | 285 | -26.582 | 19.105 | 79.889 | 1.00 | 43.99 |
| 1281 | CD | ARG | A | 285 | -26.415 | 20.119 | 81.009 | 1.00 | 45.74 |
| 1282 | NE | ARG | A | 285 | -27.612 | 20.161 | 81.838 | 1.00 | 49.71 |
| 1283 | CZ | ARG | A | 285 | -27.710 | 19.525 | 82.988 | 1.00 | 52.93 |
| 1284 | NH1 | ARG | A | 285 | -28.822 | 19.597 | 83.713 | 1.00 | 53.76 |
| 1285 | NH2 | ARG | A | 285 | -26.675 | 18.805 | 83.415 | 1.00 | 55.88 |
| 1286 | C | ARG | A | 285 | -27.906 | 16.906 | 78.267 | 1.00 | 43.69 |
| 1287 | O | ARG | A | 285 | -28.836 | 16.435 | 78.958 | 1.00 | 44.26 |
| 1288 | N | THR | A | 288 | -25.116 | 15.611 | 79.501 | 1.00 | 47.82 |
| 1289 | CA | THR | A | 288 | -23.866 | 15.594 | 80.345 | 1.00 | 48.76 |
| 1290 | CB | THR | A | 288 | -22.675 | 16.360 | 79.646 | 1.00 | 48.89 |
| 1291 | OG1 | THR | A | 288 | -22.479 | 15.933 | 78.293 | 1.00 | 51.35 |
| 1292 | CG2 | THR | A | 288 | -21.345 | 16.015 | 80.297 | 1.00 | 47.79 |
| 1293 | C | THR | A | 288 | -24.101 | 16.243 | 81.732 | 1.00 | 49.14 |
| 1294 | O | THR | A | 288 | -24.852 | 17.214 | 81.851 | 1.00 | 47.49 |
| 1295 | N | LEU | A | 289 | -23.443 | 15.702 | 82.757 | 1.00 | 50.43 |
| 1296 | CA | LEU | A | 289 | -23.441 | 16.283 | 84.118 | 1.00 | 53.20 |
| 1297 | CB | LEU | A | 289 | -22.802 | 15.267 | 85.056 | 1.00 | 53.63 |
| 1298 | CG | LEU | A | 289 | -23.766 | 14.793 | 86.121 | 1.00 | 57.03 |
| 1299 | CD1 | LEU | A | 289 | -24.112 | 15.959 | 87.046 | 1.00 | 59.33 |
| 1300 | CD2 | LEU | A | 289 | -25.011 | 14.189 | 85.463 | 1.00 | 60.93 |
| 1301 | C | LEU | A | 289 | -22.694 | 17.651 | 84.276 | 1.00 | 53.31 |
| 1302 | O | LEU | A | 289 | -21.619 | 17.817 | 83.725 | 1.00 | 53.60 |
| 1303 | N | CYS | A | 290 | -23.229 | 18.557 | 85.113 | 1.00 | 55.50 |
| 1304 | CA | CYS | A | 290 | -22.752 | 19.970 | 85.335 | 1.00 | 57.08 |
| 1305 | CB | CYS | A | 290 | -23.926 | 20.833 | 85.843 | 1.00 | 57.49 |
| 1306 | SG | CYS | A | 290 | -25.205 | 21.169 | 84.585 | 1.00 | 64.10 |
| 1307 | C | CYS | A | 290 | -21.426 | 20.313 | 86.110 | 1.00 | 56.52 |
| 1308 | O | CYS | A | 290 | -20.448 | 19.597 | 85.933 | 1.00 | 57.86 |
| 1309 | N | GLY | A | 291 | -21.379 | 21.417 | 86.898 | 1.00 | 55.52 |
| 1310 | CA | GLY | A | 291 | -20.169 | 21.921 | 87.613 | 1.00 | 52.28 |
| 1311 | C | GLY | A | 291 | -20.635 | 23.035 | 88.583 | 1.00 | 50.12 |
| 1312 | O | GLY | A | 291 | -21.578 | 22.837 | 89.335 | 1.00 | 49.36 |
| 1313 | N | THR | A | 292 | -20.005 | 24.208 | 88.624 | 1.00 | 47.90 |
| 1314 | CA | THR | A | 292 | -20.610 | 25.273 | 89.444 | 1.00 | 44.87 |
| 1315 | CB | THR | A | 292 | -19.672 | 26.461 | 89.703 | 1.00 | 47.07 |
| 1316 | OG1 | THR | A | 292 | -20.442 | 27.619 | 90.103 | 1.00 | 47.16 |
| 1317 | CG2 | THR | A | 292 | -19.180 | 26.950 | 88.383 | 1.00 | 48.62 |

FIGURE 3Z

| A | B | C | D | E | F | G | H | I | J |
|---|---|---|---|---|---|---|---|---|---|
| 1318 | C | THR | A | 292 | -21.798 | 25.781 | 88.602 | 1.00 | 41.88 |
| 1319 | O | THR | A | 292 | -21.634 | 25.980 | 87.395 | 1.00 | 41.81 |
| 1320 | N | LEU | A | 293 | -22.964 | 26.018 | 89.200 | 1.00 | 36.57 |
| 1321 | CA | LEU | A | 293 | -24.101 | 26.475 | 88.391 | 1.00 | 35.69 |
| 1322 | CB | LEU | A | 293 | -25.398 | 26.116 | 89.074 | 1.00 | 35.41 |
| 1323 | CG | LEU | A | 293 | -26.168 | 24.807 | 88.850 | 1.00 | 42.89 |
| 1324 | CD1 | LEU | A | 293 | -25.377 | 23.623 | 88.364 | 1.00 | 43.78 |
| 1325 | CD2 | LEU | A | 293 | -27.014 | 24.434 | 90.111 | 1.00 | 43.98 |
| 1326 | C | LEU | A | 293 | -24.158 | 27.975 | 88.146 | 1.00 | 33.14 |
| 1327 | O | LEU | A | 293 | -25.017 | 28.435 | 87.395 | 1.00 | 32.15 |
| 1328 | N | ASP | A | 294 | -23.246 | 28.729 | 88.755 | 1.00 | 31.34 |
| 1329 | CA | ASP | A | 294 | -23.362 | 30.191 | 88.780 | 1.00 | 30.17 |
| 1330 | CB | ASP | A | 294 | -22.072 | 30.788 | 89.362 | 1.00 | 31.41 |
| 1331 | CG | ASP | A | 294 | -22.096 | 30.775 | 90.875 | 1.00 | 36.52 |
| 1332 | OD1 | ASP | A | 294 | -21.149 | 30.228 | 91.449 | 1.00 | 42.47 |
| 1333 | OD2 | ASP | A | 294 | -23.074 | 31.224 | 91.535 | 1.00 | 39.71 |
| 1334 | C | ASP | A | 294 | -23.740 | 30.941 | 87.510 | 1.00 | 29.90 |
| 1335 | O | ASP | A | 294 | -24.404 | 31.966 | 87.568 | 1.00 | 28.82 |
| 1336 | N | TYR | A | 295 | -23.192 | 30.486 | 86.390 | 1.00 | 28.35 |
| 1337 | CA | TYR | A | 295 | -23.409 | 31.144 | 85.110 | 1.00 | 29.18 |
| 1338 | CB | TYR | A | 295 | -22.081 | 31.134 | 84.392 | 1.00 | 29.58 |
| 1339 | CG | TYR | A | 295 | -21.064 | 31.857 | 85.196 | 1.00 | 28.98 |
| 1340 | CD1 | TYR | A | 295 | -20.229 | 31.183 | 86.080 | 1.00 | 33.43 |
| 1341 | CE1 | TYR | A | 295 | -19.281 | 31.854 | 86.858 | 1.00 | 35.92 |
| 1342 | CZ | TYR | A | 295 | -19.257 | 33.216 | 86.782 | 1.00 | 33.99 |
| 1343 | OH | TYR | A | 295 | -18.331 | 33.880 | 87.548 | 1.00 | 39.27 |
| 1344 | CE2 | TYR | A | 295 | -20.078 | 33.903 | 85.910 | 1.00 | 33.69 |
| 1345 | CD2 | TYR | A | 295 | -20.983 | 33.215 | 85.124 | 1.00 | 32.42 |
| 1346 | C | TYR | A | 295 | -24.468 | 30.562 | 84.180 | 1.00 | 30.12 |
| 1347 | O | TYR | A | 295 | -24.606 | 31.005 | 83.032 | 1.00 | 29.57 |
| 1348 | N | LEU | A | 296 | -25.192 | 29.556 | 84.637 | 1.00 | 29.88 |
| 1349 | CA | LEU | A | 296 | -26.160 | 28.872 | 83.753 | 1.00 | 30.57 |
| 1350 | CB | LEU | A | 296 | -26.090 | 27.394 | 83.996 | 1.00 | 31.08 |
| 1351 | CG | LEU | A | 296 | -24.686 | 26.827 | 83.787 | 1.00 | 36.71 |
| 1352 | CD1 | LEU | A | 296 | -24.675 | 25.310 | 84.148 | 1.00 | 38.55 |
| 1353 | CD2 | LEU | A | 296 | -24.209 | 27.111 | 82.373 | 1.00 | 35.88 |
| 1354 | C | LEU | A | 296 | -27.547 | 29.301 | 84.042 | 1.00 | 30.06 |
| 1355 | O | LEU | A | 296 | -27.902 | 29.441 | 85.223 | 1.00 | 28.76 |
| 1356 | N | PRO | A | 297 | -28.346 | 29.432 | 82.969 | 1.00 | 29.59 |
| 1357 | CA | PRO | A | 297 | -29.752 | 29.814 | 83.035 | 1.00 | 29.63 |
| 1358 | CB | PRO | A | 297 | -30.105 | 30.142 | 81.563 | 1.00 | 30.10 |
| 1359 | CG | PRO | A | 297 | -29.256 | 29.232 | 80.816 | 1.00 | 30.36 |
| 1360 | CD | PRO | A | 297 | -27.902 | 29.176 | 81.578 | 1.00 | 30.37 |
| 1361 | C | PRO | A | 297 | -30.593 | 28.606 | 83.518 | 1.00 | 30.53 |
| 1362 | O | PRO | A | 297 | -30.133 | 27.475 | 83.493 | 1.00 | 29.72 |
| 1363 | N | PRO | A | 298 | -31.785 | 28.907 | 83.980 | 1.00 | 32.38 |
| 1364 | CA | PRO | A | 298 | -32.748 | 27.911 | 84.486 | 1.00 | 35.25 |
| 1365 | CB | PRO | A | 298 | -34.030 | 28.716 | 84.623 | 1.00 | 34.69 |
| 1366 | CG | PRO | A | 298 | -33.555 | 30.121 | 84.897 | 1.00 | 35.48 |
| 1367 | CD | PRO | A | 298 | -32.269 | 30.280 | 84.096 | 1.00 | 32.59 |
| 1368 | C | PRO | A | 298 | -32.951 | 26.766 | 83.492 | 1.00 | 37.27 |

FIGURE 3AA

| A | B | C | D | E | F | G | H | I | J |
|---|---|---|---|---|---|---|---|---|---|
| 1369 | O | PRO | A | 298 | -32.829 | 25.611 | 83.920 | 1.00 | 38.20 |
| 1370 | N | GLU | A | 299 | -33.089 | 27.056 | 82.197 | 1.00 | 38.20 |
| 1371 | CA | GLU | A | 299 | -33.396 | 25.984 | 81.252 | 1.00 | 40.09 |
| 1372 | CB | GLU | A | 299 | -33.745 | 26.499 | 79.833 | 1.00 | 39.94 |
| 1373 | CG | GLU | A | 299 | -32.614 | 27.242 | 79.139 | 1.00 | 39.16 |
| 1374 | CD | GLU | A | 299 | -32.578 | 28.754 | 79.410 | 1.00 | 39.82 |
| 1375 | OE1 | GLU | A | 299 | -33.124 | 29.242 | 80.436 | 1.00 | 37.57 |
| 1376 | OE2 | GLU | A | 299 | -31.980 | 29.467 | 78.564 | 1.00 | 37.07 |
| 1377 | C | GLU | A | 299 | -32.299 | 24.969 | 81.174 | 1.00 | 41.23 |
| 1378 | O | GLU | A | 299 | -32.543 | 23.747 | 81.097 | 1.00 | 41.06 |
| 1379 | N | MET | A | 300 | -31.075 | 25.468 | 81.248 | 1.00 | 41.85 |
| 1380 | CA | MET | A | 300 | -29.951 | 24.596 | 81.206 | 1.00 | 43.22 |
| 1381 | CB | MET | A | 300 | -28.679 | 25.376 | 81.027 | 1.00 | 43.88 |
| 1382 | CG | MET | A | 300 | -27.499 | 24.515 | 81.020 | 1.00 | 49.44 |
| 1383 | SD | MET | A | 300 | -26.839 | 24.501 | 79.396 | 1.00 | 60.26 |
| 1384 | CE | MET | A | 300 | -25.544 | 23.343 | 79.572 | 1.00 | 54.71 |
| 1385 | C | MET | A | 300 | -29.837 | 23.750 | 82.461 | 1.00 | 44.15 |
| 1386 | O | MET | A | 300 | -29.682 | 22.512 | 82.356 | 1.00 | 44.33 |
| 1387 | N | ILE | A | 301 | -29.864 | 24.362 | 83.638 | 1.00 | 44.85 |
| 1388 | CA | ILE | A | 301 | -29.735 | 23.521 | 84.831 | 1.00 | 46.79 |
| 1389 | CB | ILE | A | 301 | -29.657 | 24.332 | 86.111 | 1.00 | 47.71 |
| 1390 | CG1 | ILE | A | 301 | -30.818 | 25.308 | 86.276 | 1.00 | 50.37 |
| 1391 | CD1 | ILE | A | 301 | -30.163 | 26.709 | 86.641 | 1.00 | 56.06 |
| 1392 | CG2 | ILE | A | 301 | -28.369 | 25.222 | 86.119 | 1.00 | 46.42 |
| 1393 | C | ILE | A | 301 | -30.836 | 22.441 | 84.891 | 1.00 | 48.14 |
| 1394 | O | ILE | A | 301 | -30.538 | 21.258 | 85.093 | 1.00 | 48.00 |
| 1395 | N | GLU | A | 302 | -32.085 | 22.854 | 84.677 | 1.00 | 49.20 |
| 1396 | CA | GLU | A | 302 | -33.236 | 21.952 | 84.671 | 1.00 | 51.02 |
| 1397 | CB | GLU | A | 302 | -34.520 | 22.754 | 84.559 | 1.00 | 51.41 |
| 1398 | CG | GLU | A | 302 | -34.831 | 23.576 | 85.792 | 1.00 | 55.27 |
| 1399 | CD | GLU | A | 302 | -35.798 | 24.695 | 85.474 | 1.00 | 59.81 |
| 1400 | OE1 | GLU | A | 302 | -36.087 | 25.555 | 86.349 | 1.00 | 63.64 |
| 1401 | OE2 | GLU | A | 302 | -36.294 | 24.693 | 84.335 | 1.00 | 60.77 |
| 1402 | C | GLU | A | 302 | -33.242 | 20.937 | 83.540 | 1.00 | 51.10 |
| 1403 | O | GLU | A | 302 | -34.179 | 20.143 | 83.434 | 1.00 | 51.91 |
| 1404 | N | GLY | A | 303 | -32.240 | 20.988 | 82.669 | 1.00 | 50.72 |
| 1405 | CA | GLY | A | 303 | -32.155 | 20.071 | 81.553 | 1.00 | 49.63 |
| 1406 | C | GLY | A | 303 | -33.262 | 20.211 | 80.509 | 1.00 | 49.30 |
| 1407 | O | GLY | A | 303 | -33.624 | 19.227 | 79.864 | 1.00 | 50.60 |
| 1408 | N | ARG | A | 304 | -33.809 | 21.402 | 80.323 | 1.00 | 47.24 |
| 1409 | CA | ARG | A | 304 | -34.799 | 21.609 | 79.256 | 1.00 | 46.04 |
| 1410 | CB | ARG | A | 304 | -35.716 | 22.800 | 79.591 | 1.00 | 46.73 |
| 1411 | CG | ARG | A | 304 | -36.712 | 22.504 | 80.773 | 1.00 | 49.63 |
| 1412 | CD | ARG | A | 304 | -37.419 | 23.759 | 81.406 | 1.00 | 55.75 |
| 1413 | NE | ARG | A | 304 | -37.497 | 24.898 | 80.477 | 1.00 | 58.41 |
| 1414 | CZ | ARG | A | 304 | -37.277 | 26.172 | 80.822 | 1.00 | 60.70 |
| 1415 | NH1 | ARG | A | 304 | -37.360 | 27.151 | 79.903 | 1.00 | 61.20 |
| 1416 | NH2 | ARG | A | 304 | -36.965 | 26.473 | 82.083 | 1.00 | 58.65 |
| 1417 | C | ARG | A | 304 | -34.097 | 21.838 | 77.907 | 1.00 | 44.67 |
| 1418 | O | ARG | A | 304 | -32.861 | 21.996 | 77.852 | 1.00 | 43.50 |
| 1419 | N | MET | A | 305 | -34.858 | 21.822 | 76.819 | 1.00 | 41.82 |

FIGURE 3AB

| A | B | C | D | E | F | G | H | I | J |
|---|---|---|---|---|---|---|---|---|---|
| 1420 | CA | MET | A | 305 | -34.254 | 22.089 | 75.503 | 1.00 | 42.19 |
| 1421 | CB | MET | A | 305 | -35.229 | 21.851 | 74.333 | 1.00 | 41.21 |
| 1422 | CG | MET | A | 305 | -35.426 | 20.357 | 73.940 | 1.00 | 49.17 |
| 1423 | SD | MET | A | 305 | -33.904 | 19.263 | 73.897 | 1.00 | 58.33 |
| 1424 | CE | MET | A | 305 | -33.530 | 19.109 | 72.178 | 1.00 | 55.74 |
| 1425 | C | MET | A | 305 | -33.865 | 23.563 | 75.506 | 1.00 | 38.86 |
| 1426 | O | MET | A | 305 | -34.562 | 24.353 | 76.091 | 1.00 | 38.98 |
| 1427 | N | HIS | A | 306 | -32.786 | 23.933 | 74.838 | 1.00 | 37.11 |
| 1428 | CA | HIS | A | 306 | -32.358 | 25.332 | 74.903 | 1.00 | 36.23 |
| 1429 | CB | HIS | A | 306 | -31.486 | 25.515 | 76.164 | 1.00 | 34.70 |
| 1430 | CG | HIS | A | 306 | -30.350 | 24.541 | 76.239 | 1.00 | 31.57 |
| 1431 | ND1 | HIS | A | 306 | -30.436 | 23.353 | 76.920 | 1.00 | 30.19 |
| 1432 | CE1 | HIS | A | 306 | -29.306 | 22.688 | 76.809 | 1.00 | 31.98 |
| 1433 | NE2 | HIS | A | 306 | -28.485 | 23.405 | 76.061 | 1.00 | 33.02 |
| 1434 | CD2 | HIS | A | 306 | -29.117 | 24.569 | 75.698 | 1.00 | 31.19 |
| 1435 | C | HIS | A | 306 | -31.570 | 25.711 | 73.662 | 1.00 | 36.80 |
| 1436 | O | HIS | A | 306 | -31.106 | 24.834 | 72.897 | 1.00 | 36.60 |
| 1437 | N | ASP | A | 307 | -31.378 | 27.017 | 73.498 | 1.00 | 37.06 |
| 1438 | CA | ASP | A | 307 | -30.728 | 27.538 | 72.310 | 1.00 | 37.90 |
| 1439 | CB | ASP | A | 307 | -31.778 | 27.990 | 71.294 | 1.00 | 38.38 |
| 1440 | CG | ASP | A | 307 | -32.671 | 29.159 | 71.810 | 1.00 | 43.93 |
| 1441 | OD1 | ASP | A | 307 | -33.590 | 29.626 | 71.077 | 1.00 | 51.28 |
| 1442 | OD2 | ASP | A | 307 | -32.554 | 29.695 | 72.926 | 1.00 | 43.92 |
| 1443 | C | ASP | A | 307 | -29.824 | 28.702 | 72.622 | 1.00 | 37.59 |
| 1444 | O | ASP | A | 307 | -29.361 | 28.848 | 73.739 | 1.00 | 37.38 |
| 1445 | N | GLU | A | 308 | -29.676 | 29.585 | 71.642 | 1.00 | 36.80 |
| 1446 | CA | GLU | A | 308 | -28.726 | 30.683 | 71.742 | 1.00 | 37.37 |
| 1447 | CB | GLU | A | 308 | -28.825 | 31.551 | 70.492 | 1.00 | 37.85 |
| 1448 | CG | GLU | A | 308 | -28.228 | 30.905 | 69.266 | 1.00 | 40.29 |
| 1449 | CD | GLU | A | 308 | -29.197 | 29.990 | 68.528 | 1.00 | 45.91 |
| 1450 | OE1 | GLU | A | 308 | -30.253 | 29.629 | 69.089 | 1.00 | 43.52 |
| 1451 | OE2 | GLU | A | 308 | -28.879 | 29.616 | 67.361 | 1.00 | 48.59 |
| 1452 | C | GLU | A | 308 | -29.008 | 31.574 | 72.946 | 1.00 | 35.64 |
| 1453 | O | GLU | A | 308 | -28.099 | 32.237 | 73.434 | 1.00 | 34.56 |
| 1454 | N | LYS | A | 309 | -30.247 | 31.603 | 73.410 | 1.00 | 33.77 |
| 1455 | CA | LYS | A | 309 | -30.557 | 32.491 | 74.535 | 1.00 | 33.68 |
| 1456 | CB | LYS | A | 309 | -32.071 | 32.589 | 74.813 | 1.00 | 34.13 |
| 1457 | CG | LYS | A | 309 | -32.853 | 33.190 | 73.626 | 1.00 | 35.58 |
| 1458 | CD | LYS | A | 309 | -32.289 | 34.571 | 73.302 | 1.00 | 39.16 |
| 1459 | CE | LYS | A | 309 | -33.289 | 35.387 | 72.485 | 1.00 | 46.27 |
| 1460 | NZ | LYS | A | 309 | -34.624 | 35.259 | 73.121 | 1.00 | 46.60 |
| 1461 | C | LYS | A | 309 | -29.793 | 32.123 | 75.816 | 1.00 | 32.90 |
| 1462 | O | LYS | A | 309 | -29.673 | 32.945 | 76.708 | 1.00 | 32.40 |
| 1463 | N | VAL | A | 310 | -29.242 | 30.932 | 75.870 | 1.00 | 31.17 |
| 1464 | CA | VAL | A | 310 | -28.473 | 30.508 | 77.022 | 1.00 | 32.76 |
| 1465 | CB | VAL | A | 310 | -27.993 | 29.086 | 76.822 | 1.00 | 33.19 |
| 1466 | CG1 | VAL | A | 310 | -26.762 | 28.825 | 77.639 | 1.00 | 36.49 |
| 1467 | CG2 | VAL | A | 310 | -29.154 | 28.095 | 77.249 | 1.00 | 32.68 |
| 1468 | C | VAL | A | 310 | -27.292 | 31.457 | 77.250 | 1.00 | 33.09 |
| 1469 | O | VAL | A | 310 | -27.083 | 31.951 | 78.365 | 1.00 | 31.77 |
| 1470 | N | ASP | A | 311 | -26.568 | 31.770 | 76.175 | 1.00 | 31.32 |

FIGURE 3AC

| A | B | C | D | E | F | G | H | I | J |
|---|---|---|---|---|---|---|---|---|---|
| 1471 | CA  | ASP | A | 311 | -25.422 | 32.682 | 76.275 | 1.00 | 32.19 |
| 1472 | CB  | ASP | A | 311 | -24.578 | 32.656 | 74.950 | 1.00 | 32.21 |
| 1473 | CG  | ASP | A | 311 | -23.893 | 31.256 | 74.696 | 1.00 | 33.63 |
| 1474 | OD1 | ASP | A | 311 | -23.601 | 30.482 | 75.635 | 1.00 | 34.07 |
| 1475 | OD2 | ASP | A | 311 | -23.615 | 30.806 | 73.584 | 1.00 | 34.64 |
| 1476 | C   | ASP | A | 311 | -25.848 | 34.089 | 76.674 | 1.00 | 31.34 |
| 1477 | O   | ASP | A | 311 | -25.054 | 34.819 | 77.265 | 1.00 | 31.50 |
| 1478 | N   | LEU | A | 312 | -27.074 | 34.500 | 76.349 | 1.00 | 30.65 |
| 1479 | CA  | LEU | A | 312 | -27.540 | 35.829 | 76.741 | 1.00 | 30.65 |
| 1480 | CB  | LEU | A | 312 | -28.880 | 36.194 | 76.114 | 1.00 | 32.89 |
| 1481 | CG  | LEU | A | 312 | -28.740 | 36.747 | 74.676 | 1.00 | 33.15 |
| 1482 | CD1 | LEU | A | 312 | -27.998 | 38.080 | 74.782 | 1.00 | 37.24 |
| 1483 | CD2 | LEU | A | 312 | -27.978 | 35.740 | 73.770 | 1.00 | 37.98 |
| 1484 | C   | LEU | A | 312 | -27.659 | 35.915 | 78.252 | 1.00 | 30.10 |
| 1485 | O   | LEU | A | 312 | -27.212 | 36.882 | 78.870 | 1.00 | 29.74 |
| 1486 | N   | TRP | A | 313 | -28.221 | 34.878 | 78.847 | 1.00 | 28.70 |
| 1487 | CA  | TRP | A | 313 | -28.290 | 34.885 | 80.311 | 1.00 | 29.18 |
| 1488 | CB  | TRP | A | 313 | -28.980 | 33.655 | 80.774 | 1.00 | 29.28 |
| 1489 | CG  | TRP | A | 313 | -28.856 | 33.398 | 82.197 | 1.00 | 29.13 |
| 1490 | CD1 | TRP | A | 313 | -27.798 | 32.871 | 82.848 | 1.00 | 26.72 |
| 1491 | NE1 | TRP | A | 313 | -28.104 | 32.728 | 84.184 | 1.00 | 28.25 |
| 1492 | CE2 | TRP | A | 313 | -29.402 | 33.129 | 84.370 | 1.00 | 28.86 |
| 1493 | CD2 | TRP | A | 313 | -29.877 | 33.584 | 83.145 | 1.00 | 26.93 |
| 1494 | CE3 | TRP | A | 313 | -31.192 | 34.028 | 83.062 | 1.00 | 26.93 |
| 1495 | CZ3 | TRP | A | 313 | -31.969 | 34.038 | 84.199 | 1.00 | 31.77 |
| 1496 | CH2 | TRP | A | 313 | -31.450 | 33.635 | 85.422 | 1.00 | 28.09 |
| 1497 | CZ2 | TRP | A | 313 | -30.175 | 33.170 | 85.538 | 1.00 | 26.06 |
| 1498 | C   | TRP | A | 313 | -26.880 | 34.959 | 80.918 | 1.00 | 29.84 |
| 1499 | O   | TRP | A | 313 | -26.633 | 35.738 | 81.823 | 1.00 | 27.08 |
| 1500 | N   | SER | A | 314 | -25.958 | 34.152 | 80.409 | 1.00 | 29.72 |
| 1501 | CA  | SER | A | 314 | -24.593 | 34.162 | 80.901 | 1.00 | 30.37 |
| 1502 | CB  | SER | A | 314 | -23.777 | 33.087 | 80.139 | 1.00 | 30.46 |
| 1503 | OG  | SER | A | 314 | -24.244 | 31.776 | 80.494 | 1.00 | 35.30 |
| 1504 | C   | SER | A | 314 | -23.937 | 35.568 | 80.801 | 1.00 | 31.13 |
| 1505 | O   | SER | A | 314 | -23.199 | 35.980 | 81.679 | 1.00 | 27.77 |
| 1506 | N   | LEU | A | 315 | -24.183 | 36.276 | 79.708 | 1.00 | 30.52 |
| 1507 | CA  | LEU | A | 315 | -23.699 | 37.630 | 79.537 | 1.00 | 31.47 |
| 1508 | CB  | LEU | A | 315 | -24.303 | 38.182 | 78.258 | 1.00 | 31.92 |
| 1509 | CG  | LEU | A | 315 | -23.556 | 39.322 | 77.630 | 1.00 | 34.89 |
| 1510 | CD1 | LEU | A | 315 | -22.077 | 38.966 | 77.617 | 1.00 | 32.65 |
| 1511 | CD2 | LEU | A | 315 | -24.094 | 39.490 | 76.207 | 1.00 | 34.24 |
| 1512 | C   | LEU | A | 315 | -24.189 | 38.521 | 80.657 | 1.00 | 30.26 |
| 1513 | O   | LEU | A | 315 | -23.467 | 39.375 | 81.154 | 1.00 | 29.93 |
| 1514 | N   | GLY | A | 316 | -25.416 | 38.270 | 81.084 | 1.00 | 31.24 |
| 1515 | CA  | GLY | A | 316 | -26.030 | 39.018 | 82.160 | 1.00 | 28.40 |
| 1516 | C   | GLY | A | 316 | -25.336 | 38.709 | 83.470 | 1.00 | 29.31 |
| 1517 | O   | GLY | A | 316 | -24.989 | 39.635 | 84.232 | 1.00 | 28.62 |
| 1518 | N   | VAL | A | 317 | -25.123 | 37.426 | 83.751 | 1.00 | 29.39 |
| 1519 | CA  | VAL | A | 317 | -24.392 | 37.045 | 84.964 | 1.00 | 29.86 |
| 1520 | CB  | VAL | A | 317 | -24.272 | 35.498 | 85.118 | 1.00 | 29.69 |
| 1521 | CG1 | VAL | A | 317 | -23.433 | 35.135 | 86.302 | 1.00 | 31.40 |

FIGURE 3AD

| A | B | C | D | E | F | G | H | I | J |
|---|---|---|---|---|---|---|---|---|---|
| 1522 | CG2 | VAL | A | 317 | -25.625 | 34.885 | 85.201 | 1.00 | 30.52 |
| 1523 | C | VAL | A | 317 | -22.971 | 37.715 | 84.961 | 1.00 | 30.09 |
| 1524 | O | VAL | A | 317 | -22.525 | 38.275 | 85.976 | 1.00 | 28.93 |
| 1525 | N | LEU | A | 318 | -22.283 | 37.665 | 83.832 | 1.00 | 29.07 |
| 1526 | CA | LEU | A | 318 | -20.973 | 38.219 | 83.759 | 1.00 | 29.74 |
| 1527 | CB | LEU | A | 318 | -20.327 | 37.940 | 82.391 | 1.00 | 29.62 |
| 1528 | CG | LEU | A | 318 | -19.795 | 36.566 | 82.116 | 1.00 | 33.45 |
| 1529 | CD1 | LEU | A | 318 | -19.343 | 36.587 | 80.606 | 1.00 | 31.59 |
| 1530 | CD2 | LEU | A | 318 | -18.570 | 36.186 | 83.001 | 1.00 | 26.99 |
| 1531 | C | LEU | A | 318 | -21.015 | 39.716 | 83.938 | 1.00 | 29.78 |
| 1532 | O | LEU | A | 318 | -20.140 | 40.243 | 84.572 | 1.00 | 29.27 |
| 1533 | N | CYS | A | 319 | -22.036 | 40.401 | 83.423 | 1.00 | 29.91 |
| 1534 | CA | CYS | A | 319 | -22.072 | 41.831 | 83.606 | 1.00 | 31.51 |
| 1535 | CB | CYS | A | 319 | -23.214 | 42.431 | 82.818 | 1.00 | 31.68 |
| 1536 | SG | CYS | A | 319 | -23.007 | 44.241 | 82.719 | 1.00 | 40.49 |
| 1537 | C | CYS | A | 319 | -22.152 | 42.216 | 85.116 | 1.00 | 31.22 |
| 1538 | O | CYS | A | 319 | -21.439 | 43.092 | 85.632 | 1.00 | 29.46 |
| 1539 | N | TYR | A | 320 | -22.985 | 41.482 | 85.819 | 1.00 | 29.74 |
| 1540 | CA | TYR | A | 320 | -23.149 | 41.689 | 87.243 | 1.00 | 28.88 |
| 1541 | CB | TYR | A | 320 | -24.320 | 40.843 | 87.746 | 1.00 | 28.54 |
| 1542 | CG | TYR | A | 320 | -24.606 | 40.973 | 89.212 | 1.00 | 28.67 |
| 1543 | CD1 | TYR | A | 320 | -23.746 | 40.436 | 90.152 | 1.00 | 28.63 |
| 1544 | CE1 | TYR | A | 320 | -24.037 | 40.574 | 91.521 | 1.00 | 31.25 |
| 1545 | CZ | TYR | A | 320 | -25.218 | 41.261 | 91.901 | 1.00 | 27.73 |
| 1546 | OH | TYR | A | 320 | -25.601 | 41.384 | 93.204 | 1.00 | 34.97 |
| 1547 | CE2 | TYR | A | 320 | -26.070 | 41.711 | 91.016 | 1.00 | 28.41 |
| 1548 | CD2 | TYR | A | 320 | -25.745 | 41.625 | 89.636 | 1.00 | 27.53 |
| 1549 | C | TYR | A | 320 | -21.810 | 41.373 | 87.977 | 1.00 | 29.65 |
| 1550 | O | TYR | A | 320 | -21.286 | 42.208 | 88.741 | 1.00 | 28.99 |
| 1551 | N | GLU | A | 321 | -21.252 | 40.185 | 87.727 | 1.00 | 28.26 |
| 1552 | CA | GLU | A | 321 | -19.996 | 39.790 | 88.381 | 1.00 | 29.29 |
| 1553 | CB | GLU | A | 321 | -19.511 | 38.398 | 87.976 | 1.00 | 27.46 |
| 1554 | CG | GLU | A | 321 | -18.367 | 37.989 | 88.874 | 1.00 | 31.39 |
| 1555 | CD | GLU | A | 321 | -17.939 | 36.565 | 88.757 | 1.00 | 39.04 |
| 1556 | OE1 | GLU | A | 321 | -16.893 | 36.204 | 89.386 | 1.00 | 40.16 |
| 1557 | OE2 | GLU | A | 321 | -18.629 | 35.792 | 88.062 | 1.00 | 41.43 |
| 1558 | C | GLU | A | 321 | -18.858 | 40.810 | 88.173 | 1.00 | 29.09 |
| 1559 | O | GLU | A | 321 | -18.148 | 41.162 | 89.112 | 1.00 | 28.70 |
| 1560 | N | PHE | A | 322 | -18.712 | 41.290 | 86.942 | 1.00 | 28.18 |
| 1561 | CA | PHE | A | 322 | -17.690 | 42.282 | 86.620 | 1.00 | 29.59 |
| 1562 | CB | PHE | A | 322 | -17.742 | 42.671 | 85.130 | 1.00 | 30.02 |
| 1563 | CG | PHE | A | 322 | -17.277 | 41.578 | 84.189 | 1.00 | 29.13 |
| 1564 | CD1 | PHE | A | 322 | -16.706 | 40.416 | 84.659 | 1.00 | 29.70 |
| 1565 | CE1 | PHE | A | 322 | -16.287 | 39.422 | 83.772 | 1.00 | 32.17 |
| 1566 | CZ | PHE | A | 322 | -16.416 | 39.619 | 82.418 | 1.00 | 33.54 |
| 1567 | CE2 | PHE | A | 322 | -16.981 | 40.753 | 81.954 | 1.00 | 33.04 |
| 1568 | CD2 | PHE | A | 322 | -17.412 | 41.738 | 82.844 | 1.00 | 30.45 |
| 1569 | C | PHE | A | 322 | -17.874 | 43.526 | 87.468 | 1.00 | 30.51 |
| 1570 | O | PHE | A | 322 | -16.924 | 44.017 | 88.092 | 1.00 | 32.18 |
| 1571 | N | LEU | A | 323 | -19.079 | 44.047 | 87.443 | 1.00 | 30.76 |
| 1572 | CA | LEU | A | 323 | -19.461 | 45.235 | 88.188 | 1.00 | 31.93 |

FIGURE 3AE

| A | B | C | D | E | F | G | H | I | J |
|---|---|---|---|---|---|---|---|---|---|
| 1573 | CB | LEU | A | 323 | -20.850 | 45.703 | 87.765 | 1.00 | 31.23 |
| 1574 | CG | LEU | A | 323 | -21.005 | 46.300 | 86.372 | 1.00 | 29.55 |
| 1575 | CD1 | LEU | A | 323 | -22.381 | 46.696 | 86.162 | 1.00 | 28.14 |
| 1576 | CD2 | LEU | A | 323 | -20.049 | 47.538 | 86.199 | 1.00 | 33.58 |
| 1577 | C | LEU | A | 323 | -19.455 | 45.015 | 89.689 | 1.00 | 33.43 |
| 1578 | O | LEU | A | 323 | -19.064 | 45.912 | 90.469 | 1.00 | 33.54 |
| 1579 | N | VAL | A | 324 | -19.868 | 43.827 | 90.139 | 1.00 | 33.63 |
| 1580 | CA | VAL | A | 324 | -20.061 | 43.630 | 91.587 | 1.00 | 33.28 |
| 1581 | CB | VAL | A | 324 | -21.449 | 42.976 | 91.860 | 1.00 | 33.80 |
| 1582 | CG1 | VAL | A | 324 | -21.709 | 42.622 | 93.380 | 1.00 | 32.67 |
| 1583 | CG2 | VAL | A | 324 | -22.586 | 43.857 | 91.300 | 1.00 | 34.21 |
| 1584 | C | VAL | A | 324 | -18.928 | 42.911 | 92.263 | 1.00 | 35.51 |
| 1585 | O | VAL | A | 324 | -18.642 | 43.145 | 93.424 | 1.00 | 35.39 |
| 1586 | N | GLY | A | 325 | -18.226 | 42.038 | 91.560 | 1.00 | 35.56 |
| 1587 | CA | GLY | A | 325 | -17.194 | 41.273 | 92.225 | 1.00 | 35.35 |
| 1588 | C | GLY | A | 325 | -17.594 | 39.835 | 92.535 | 1.00 | 36.00 |
| 1589 | O | GLY | A | 325 | -16.746 | 39.003 | 92.813 | 1.00 | 37.09 |
| 1590 | N | LYS | A | 326 | -18.880 | 39.528 | 92.442 | 1.00 | 35.21 |
| 1591 | CA | LYS | A | 326 | -19.304 | 38.161 | 92.638 | 1.00 | 35.82 |
| 1592 | CB | LYS | A | 326 | -19.650 | 37.922 | 94.122 | 1.00 | 35.98 |
| 1593 | CG | LYS | A | 326 | -20.941 | 38.598 | 94.489 | 1.00 | 40.08 |
| 1594 | CD | LYS | A | 326 | -21.233 | 38.587 | 96.024 | 1.00 | 47.40 |
| 1595 | CE | LYS | A | 326 | -22.214 | 39.748 | 96.321 | 1.00 | 51.86 |
| 1596 | NZ | LYS | A | 326 | -21.819 | 40.553 | 97.484 | 1.00 | 48.80 |
| 1597 | C | LYS | A | 326 | -20.512 | 37.929 | 91.754 | 1.00 | 33.85 |
| 1598 | O | LYS | A | 326 | -21.227 | 38.853 | 91.451 | 1.00 | 31.55 |
| 1599 | N | PRO | A | 327 | -20.755 | 36.691 | 91.332 | 1.00 | 33.50 |
| 1600 | CA | PRO | A | 327 | -21.927 | 36.437 | 90.463 | 1.00 | 32.79 |
| 1601 | CB | PRO | A | 327 | -21.678 | 34.994 | 89.969 | 1.00 | 33.94 |
| 1602 | CG | PRO | A | 327 | -21.026 | 34.347 | 91.241 | 1.00 | 35.31 |
| 1603 | CD | PRO | A | 327 | -19.983 | 35.449 | 91.621 | 1.00 | 33.33 |
| 1604 | C | PRO | A | 327 | -23.245 | 36.595 | 91.255 | 1.00 | 30.81 |
| 1605 | O | PRO | A | 327 | -23.300 | 36.380 | 92.463 | 1.00 | 32.11 |
| 1606 | N | PRO | A | 328 | -24.309 | 36.989 | 90.598 | 1.00 | 29.67 |
| 1607 | CA | PRO | A | 328 | -25.541 | 37.336 | 91.315 | 1.00 | 29.91 |
| 1608 | CB | PRO | A | 328 | -26.396 | 37.936 | 90.249 | 1.00 | 28.24 |
| 1609 | CG | PRO | A | 328 | -25.879 | 37.253 | 88.972 | 1.00 | 30.64 |
| 1610 | CD | PRO | A | 328 | -24.406 | 37.239 | 89.158 | 1.00 | 29.03 |
| 1611 | C | PRO | A | 328 | -26.291 | 36.189 | 92.066 | 1.00 | 32.07 |
| 1612 | O | PRO | A | 328 | -27.110 | 36.498 | 92.935 | 1.00 | 31.51 |
| 1613 | N | PHE | A | 329 | -26.007 | 34.919 | 91.745 | 1.00 | 30.77 |
| 1614 | CA | PHE | A | 329 | -26.723 | 33.835 | 92.391 | 1.00 | 32.15 |
| 1615 | CB | PHE | A | 329 | -27.367 | 32.923 | 91.329 | 1.00 | 30.34 |
| 1616 | CG | PHE | A | 329 | -28.198 | 33.663 | 90.371 | 1.00 | 29.16 |
| 1617 | CD1 | PHE | A | 329 | -29.349 | 34.294 | 90.783 | 1.00 | 26.86 |
| 1618 | CE1 | PHE | A | 329 | -30.109 | 35.003 | 89.921 | 1.00 | 26.79 |
| 1619 | CZ | PHE | A | 329 | -29.692 | 35.115 | 88.583 | 1.00 | 29.19 |
| 1620 | CE2 | PHE | A | 329 | -28.507 | 34.503 | 88.156 | 1.00 | 28.24 |
| 1621 | CD2 | PHE | A | 329 | -27.779 | 33.782 | 89.042 | 1.00 | 29.12 |
| 1622 | C | PHE | A | 329 | -25.833 | 33.027 | 93.287 | 1.00 | 33.34 |
| 1623 | O | PHE | A | 329 | -26.260 | 31.988 | 93.763 | 1.00 | 35.58 |

FIGURE 3AF

| A | B | C | D | E | F | G | H | I | J |
|---|---|---|---|---|---|---|---|---|---|
| 1624 | N | GLU | A | 330 | -24.623 | 33.505 | 93.513 | 1.00 | 35.42 |
| 1625 | CA | GLU | A | 330 | -23.656 | 32.877 | 94.397 | 1.00 | 38.76 |
| 1626 | CB | GLU | A | 330 | -22.588 | 33.906 | 94.768 | 1.00 | 39.72 |
| 1627 | CG | GLU | A | 330 | -21.251 | 33.325 | 95.177 | 1.00 | 44.21 |
| 1628 | CD | GLU | A | 330 | -20.378 | 34.364 | 95.894 | 1.00 | 53.19 |
| 1629 | OE1 | GLU | A | 330 | -20.779 | 34.883 | 96.993 | 1.00 | 53.55 |
| 1630 | OE2 | GLU | A | 330 | -19.295 | 34.665 | 95.337 | 1.00 | 58.16 |
| 1631 | C | GLU | A | 330 | -24.373 | 32.498 | 95.704 | 1.00 | 39.04 |
| 1632 | O | GLU | A | 330 | -25.175 | 33.269 | 96.217 | 1.00 | 37.84 |
| 1633 | N | ALA | A | 331 | -24.084 | 31.303 | 96.200 | 1.00 | 40.28 |
| 1634 | CA | ALA | A | 331 | -24.680 | 30.771 | 97.425 | 1.00 | 40.27 |
| 1635 | CB | ALA | A | 331 | -26.002 | 30.149 | 97.126 | 1.00 | 41.00 |
| 1636 | C | ALA | A | 331 | -23.658 | 29.753 | 97.888 | 1.00 | 41.45 |
| 1637 | O | ALA | A | 331 | -22.757 | 29.404 | 97.127 | 1.00 | 41.16 |
| 1638 | N | ASN | A | 332 | -23.776 | 29.280 | 99.121 | 1.00 | 41.89 |
| 1639 | CA | ASN | A | 332 | -22.737 | 28.404 | 99.662 | 1.00 | 40.88 |
| 1640 | CB | ASN | A | 332 | -22.602 | 28.566 | 101.220 | 1.00 | 43.11 |
| 1641 | CG | ASN | A | 332 | -21.784 | 29.826 | 101.626 | 1.00 | 48.66 |
| 1642 | OD1 | ASN | A | 332 | -20.570 | 29.937 | 101.359 | 1.00 | 55.22 |
| 1643 | ND2 | ASN | A | 332 | -22.462 | 30.786 | 102.245 | 1.00 | 55.15 |
| 1644 | C | ASN | A | 332 | -23.050 | 26.959 | 99.235 | 1.00 | 37.57 |
| 1645 | O | ASN | A | 332 | -22.225 | 26.050 | 99.332 | 1.00 | 39.59 |
| 1646 | N | THR | A | 333 | -24.231 | 26.755 | 98.724 | 1.00 | 36.44 |
| 1647 | CA | THR | A | 333 | -24.536 | 25.410 | 98.298 | 1.00 | 36.73 |
| 1648 | CB | THR | A | 333 | -25.645 | 24.665 | 99.264 | 1.00 | 37.09 |
| 1649 | OG1 | THR | A | 333 | -25.097 | 24.779 | 100.596 | 1.00 | 40.58 |
| 1650 | CG2 | THR | A | 333 | -25.650 | 23.188 | 99.046 | 1.00 | 42.78 |
| 1651 | C | THR | A | 333 | -24.981 | 25.425 | 96.865 | 1.00 | 34.33 |
| 1652 | O | THR | A | 333 | -25.642 | 26.372 | 96.398 | 1.00 | 33.08 |
| 1653 | N | TYR | A | 334 | -24.713 | 24.319 | 96.190 | 1.00 | 34.09 |
| 1654 | CA | TYR | A | 334 | -25.181 | 24.137 | 94.830 | 1.00 | 33.28 |
| 1655 | CB | TYR | A | 334 | -24.748 | 22.746 | 94.425 | 1.00 | 34.15 |
| 1656 | CG | TYR | A | 334 | -25.241 | 22.198 | 93.148 | 1.00 | 35.67 |
| 1657 | CD1 | TYR | A | 334 | -24.367 | 22.102 | 92.069 | 1.00 | 39.34 |
| 1658 | CE1 | TYR | A | 334 | -24.765 | 21.536 | 90.885 | 1.00 | 41.47 |
| 1659 | CZ | TYR | A | 334 | -26.025 | 21.028 | 90.764 | 1.00 | 45.44 |
| 1660 | OH | TYR | A | 334 | -26.316 | 20.439 | 89.536 | 1.00 | 53.44 |
| 1661 | CE2 | TYR | A | 334 | -26.931 | 21.076 | 91.822 | 1.00 | 41.49 |
| 1662 | CD2 | TYR | A | 334 | -26.535 | 21.644 | 93.021 | 1.00 | 39.26 |
| 1663 | C | TYR | A | 334 | -26.682 | 24.162 | 94.837 | 1.00 | 34.00 |
| 1664 | O | TYR | A | 334 | -27.330 | 24.686 | 93.921 | 1.00 | 32.29 |
| 1665 | N | GLN | A | 335 | -27.263 | 23.490 | 95.830 | 1.00 | 33.92 |
| 1666 | CA | GLN | A | 335 | -28.698 | 23.382 | 95.856 | 1.00 | 34.59 |
| 1667 | CB | GLN | A | 335 | -29.136 | 22.355 | 96.934 | 1.00 | 36.44 |
| 1668 | CG | GLN | A | 335 | -28.819 | 20.855 | 96.503 | 1.00 | 37.94 |
| 1669 | CD | GLN | A | 335 | -27.495 | 20.276 | 97.085 | 1.00 | 40.55 |
| 1670 | OE1 | GLN | A | 335 | -27.461 | 19.102 | 97.552 | 1.00 | 37.86 |
| 1671 | NE2 | GLN | A | 335 | -26.437 | 21.088 | 97.108 | 1.00 | 36.60 |
| 1672 | C | GLN | A | 335 | -29.324 | 24.794 | 96.037 | 1.00 | 34.20 |
| 1673 | O | GLN | A | 335 | -30.282 | 25.140 | 95.379 | 1.00 | 35.30 |
| 1674 | N | GLU | A | 336 | -28.791 | 25.559 | 96.942 | 1.00 | 32.77 |

FIGURE 3AG

| A | B | C | D | E | F | G | H | I | J |
|---|---|---|---|---|---|---|---|---|---|
| 1675 | CA | GLU | A | 336 | -29.205 | 26.915 | 97.201 | 1.00 | 34.44 |
| 1676 | CB | GLU | A | 336 | -28.385 | 27.265 | 98.440 | 1.00 | 36.83 |
| 1677 | CG | GLU | A | 336 | -28.352 | 28.650 | 99.013 | 1.00 | 40.38 |
| 1678 | CD | GLU | A | 336 | -27.092 | 28.866 | 99.875 | 1.00 | 50.58 |
| 1679 | OE1 | GLU | A | 336 | -25.978 | 28.319 | 99.620 | 1.00 | 58.53 |
| 1680 | OE2 | GLU | A | 336 | -27.126 | 29.678 | 100.790 | 1.00 | 40.31 |
| 1681 | C | GLU | A | 336 | -28.995 | 27.811 | 95.873 | 1.00 | 33.80 |
| 1682 | O | GLU | A | 336 | -29.877 | 28.563 | 95.449 | 1.00 | 31.17 |
| 1683 | N | THR | A | 337 | -27.868 | 27.635 | 95.191 | 1.00 | 32.08 |
| 1684 | CA | THR | A | 337 | -27.662 | 28.368 | 93.945 | 1.00 | 31.48 |
| 1685 | CB | THR | A | 337 | -26.235 | 28.047 | 93.405 | 1.00 | 30.08 |
| 1686 | OG1 | THR | A | 337 | -25.313 | 28.487 | 94.390 | 1.00 | 33.00 |
| 1687 | CG2 | THR | A | 337 | -25.906 | 28.929 | 92.159 | 1.00 | 28.28 |
| 1688 | C | THR | A | 337 | -28.724 | 28.055 | 92.919 | 1.00 | 29.52 |
| 1689 | O | THR | A | 337 | -29.235 | 28.932 | 92.247 | 1.00 | 28.46 |
| 1690 | N | TYR | A | 338 | -29.027 | 26.756 | 92.754 | 1.00 | 30.17 |
| 1691 | CA | TYR | A | 338 | -30.049 | 26.309 | 91.844 | 1.00 | 31.26 |
| 1692 | CB | TYR | A | 338 | -30.212 | 24.805 | 92.063 | 1.00 | 33.22 |
| 1693 | CG | TYR | A | 338 | -31.212 | 24.185 | 91.144 | 1.00 | 39.22 |
| 1694 | CD1 | TYR | A | 338 | -30.800 | 23.567 | 89.964 | 1.00 | 43.19 |
| 1695 | CE1 | TYR | A | 338 | -31.709 | 22.969 | 89.124 | 1.00 | 48.41 |
| 1696 | CZ | TYR | A | 338 | -33.058 | 23.003 | 89.460 | 1.00 | 51.06 |
| 1697 | OH | TYR | A | 338 | -33.992 | 22.431 | 88.628 | 1.00 | 55.33 |
| 1698 | CE2 | TYR | A | 338 | -33.479 | 23.615 | 90.622 | 1.00 | 46.29 |
| 1699 | CD2 | TYR | A | 338 | -32.560 | 24.179 | 91.462 | 1.00 | 40.97 |
| 1700 | C | TYR | A | 338 | -31.396 | 27.002 | 92.147 | 1.00 | 30.29 |
| 1701 | O | TYR | A | 338 | -32.102 | 27.472 | 91.277 | 1.00 | 29.01 |
| 1702 | N | ALA | A | 339 | -31.739 | 27.026 | 93.411 | 1.00 | 29.94 |
| 1703 | CA | ALA | A | 339 | -32.984 | 27.737 | 93.804 | 1.00 | 30.96 |
| 1704 | CB | ALA | A | 339 | -33.149 | 27.684 | 95.338 | 1.00 | 30.49 |
| 1705 | C | ALA | A | 339 | -32.960 | 29.196 | 93.377 | 1.00 | 29.24 |
| 1706 | O | ALA | A | 339 | -33.915 | 29.676 | 92.798 | 1.00 | 30.50 |
| 1707 | N | ARG | A | 340 | -31.867 | 29.875 | 93.686 | 1.00 | 28.80 |
| 1708 | CA | ARG | A | 340 | -31.708 | 31.285 | 93.348 | 1.00 | 29.69 |
| 1709 | CB | ARG | A | 340 | -30.375 | 31.804 | 93.896 | 1.00 | 29.56 |
| 1710 | CG | ARG | A | 340 | -30.447 | 31.776 | 95.494 | 1.00 | 34.62 |
| 1711 | CD | ARG | A | 340 | -31.154 | 32.954 | 96.011 | 1.00 | 39.53 |
| 1712 | NE | ARG | A | 340 | -30.493 | 34.042 | 95.311 | 1.00 | 45.06 |
| 1713 | CZ | ARG | A | 340 | -29.323 | 34.499 | 95.716 | 1.00 | 45.59 |
| 1714 | NH1 | ARG | A | 340 | -28.683 | 35.456 | 95.038 | 1.00 | 44.01 |
| 1715 | NH2 | ARG | A | 340 | -28.835 | 33.995 | 96.846 | 1.00 | 44.77 |
| 1716 | C | ARG | A | 340 | -31.871 | 31.547 | 91.858 | 1.00 | 29.56 |
| 1717 | O | ARG | A | 340 | -32.649 | 32.431 | 91.413 | 1.00 | 29.84 |
| 1718 | N | ILE | A | 341 | -31.248 | 30.679 | 91.087 | 1.00 | 29.70 |
| 1719 | CA | ILE | A | 341 | -31.279 | 30.831 | 89.641 | 1.00 | 27.75 |
| 1720 | CB | ILE | A | 341 | -30.265 | 29.851 | 89.077 | 1.00 | 27.48 |
| 1721 | CG1 | ILE | A | 341 | -28.835 | 30.335 | 89.281 | 1.00 | 24.64 |
| 1722 | CD1 | ILE | A | 341 | -27.801 | 29.268 | 88.849 | 1.00 | 27.34 |
| 1723 | CG2 | ILE | A | 341 | -30.531 | 29.617 | 87.612 | 1.00 | 28.09 |
| 1724 | C | ILE | A | 341 | -32.653 | 30.582 | 89.129 | 1.00 | 28.03 |
| 1725 | O | ILE | A | 341 | -33.236 | 31.391 | 88.388 | 1.00 | 29.33 |

FIGURE 3AH

| A | B | C | D | E | F | G | H | I | J |
|---|---|---|---|---|---|---|---|---|---|
| 1726 | N | SER | A | 342 | -33.258 | 29.478 | 89.585 | 1.00 | 30.95 |
| 1727 | CA | SER | A | 342 | -34.581 | 29.093 | 89.125 | 1.00 | 31.90 |
| 1728 | CB | SER | A | 342 | -34.973 | 27.779 | 89.822 | 1.00 | 33.11 |
| 1729 | OG | SER | A | 342 | -36.337 | 27.538 | 89.665 | 1.00 | 42.55 |
| 1730 | C | SER | A | 342 | -35.593 | 30.214 | 89.400 | 1.00 | 32.49 |
| 1731 | O | SER | A | 342 | -36.445 | 30.492 | 88.565 | 1.00 | 35.12 |
| 1732 | N | ARG | A | 343 | -35.471 | 30.872 | 90.559 | 1.00 | 31.84 |
| 1733 | CA | ARG | A | 343 | -36.386 | 31.949 | 90.917 | 1.00 | 32.56 |
| 1734 | CB | ARG | A | 343 | -36.532 | 32.017 | 92.470 | 1.00 | 33.12 |
| 1735 | CG | ARG | A | 343 | -37.178 | 30.751 | 93.099 | 1.00 | 36.80 |
| 1736 | CD | ARG | A | 343 | -36.953 | 30.623 | 94.628 | 1.00 | 43.39 |
| 1737 | NE | ARG | A | 343 | -37.670 | 29.540 | 95.344 | 1.00 | 52.05 |
| 1738 | CZ | ARG | A | 343 | -38.085 | 28.360 | 94.847 | 1.00 | 55.23 |
| 1739 | NH1 | ARG | A | 343 | -37.862 | 28.015 | 93.587 | 1.00 | 58.10 |
| 1740 | NH2 | ARG | A | 343 | -38.717 | 27.495 | 95.654 | 1.00 | 55.82 |
| 1741 | C | ARG | A | 343 | -35.914 | 33.324 | 90.386 | 1.00 | 32.02 |
| 1742 | O | ARG | A | 343 | -36.648 | 34.286 | 90.481 | 1.00 | 31.13 |
| 1743 | N | VAL | A | 344 | -34.717 | 33.360 | 89.766 | 1.00 | 32.93 |
| 1744 | CA | VAL | A | 344 | -34.045 | 34.613 | 89.312 | 1.00 | 33.02 |
| 1745 | CB | VAL | A | 344 | -34.600 | 35.259 | 88.032 | 1.00 | 33.79 |
| 1746 | CG1 | VAL | A | 344 | -33.546 | 36.165 | 87.403 | 1.00 | 33.57 |
| 1747 | CG2 | VAL | A | 344 | -35.020 | 34.205 | 87.041 | 1.00 | 34.92 |
| 1748 | C | VAL | A | 344 | -33.993 | 35.587 | 90.479 | 1.00 | 31.91 |
| 1749 | O | VAL | A | 344 | -34.392 | 36.741 | 90.393 | 1.00 | 32.52 |
| 1750 | N | GLU | A | 345 | -33.500 | 35.117 | 91.597 | 1.00 | 33.06 |
| 1751 | CA | GLU | A | 345 | -33.507 | 35.977 | 92.743 | 1.00 | 35.54 |
| 1752 | CB | GLU | A | 345 | -34.047 | 35.248 | 93.988 | 1.00 | 37.02 |
| 1753 | CG | GLU | A | 345 | -33.651 | 33.818 | 94.122 | 1.00 | 44.67 |
| 1754 | CD | GLU | A | 345 | -34.183 | 33.209 | 95.428 | 1.00 | 54.61 |
| 1755 | OE1 | GLU | A | 345 | -34.610 | 33.982 | 96.347 | 1.00 | 58.06 |
| 1756 | OE2 | GLU | A | 345 | -34.139 | 31.965 | 95.554 | 1.00 | 58.84 |
| 1757 | C | GLU | A | 345 | -32.132 | 36.606 | 92.961 | 1.00 | 33.87 |
| 1758 | O | GLU | A | 345 | -31.186 | 35.950 | 93.332 | 1.00 | 33.72 |
| 1759 | N | PHE | A | 346 | -32.045 | 37.894 | 92.694 | 1.00 | 32.77 |
| 1760 | CA | PHE | A | 346 | -30.811 | 38.628 | 92.902 | 1.00 | 32.91 |
| 1761 | CB | PHE | A | 346 | -29.903 | 38.502 | 91.657 | 1.00 | 33.13 |
| 1762 | CG | PHE | A | 346 | -30.431 | 39.197 | 90.469 | 1.00 | 34.17 |
| 1763 | CD1 | PHE | A | 346 | -31.338 | 38.570 | 89.647 | 1.00 | 36.56 |
| 1764 | CE1 | PHE | A | 346 | -31.838 | 39.183 | 88.527 | 1.00 | 35.71 |
| 1765 | CZ | PHE | A | 346 | -31.465 | 40.474 | 88.220 | 1.00 | 38.88 |
| 1766 | CE2 | PHE | A | 346 | -30.569 | 41.142 | 89.037 | 1.00 | 38.32 |
| 1767 | CD2 | PHE | A | 346 | -30.018 | 40.488 | 90.146 | 1.00 | 39.09 |
| 1768 | C | PHE | A | 346 | -31.134 | 40.106 | 93.174 | 1.00 | 33.06 |
| 1769 | O | PHE | A | 346 | -32.209 | 40.598 | 92.785 | 1.00 | 32.92 |
| 1770 | N | THR | A | 347 | -30.225 | 40.796 | 93.853 | 1.00 | 32.73 |
| 1771 | CA | THR | A | 347 | -30.385 | 42.225 | 94.108 | 1.00 | 33.76 |
| 1772 | CB | THR | A | 347 | -30.753 | 42.502 | 95.597 | 1.00 | 33.91 |
| 1773 | OG1 | THR | A | 347 | -29.776 | 41.870 | 96.415 | 1.00 | 35.21 |
| 1774 | CG2 | THR | A | 347 | -32.067 | 41.798 | 96.015 | 1.00 | 33.87 |
| 1775 | C | THR | A | 347 | -29.025 | 42.839 | 93.850 | 1.00 | 33.74 |
| 1776 | O | THR | A | 347 | -27.998 | 42.142 | 93.915 | 1.00 | 34.60 |

FIGURE 3AI

| A | B | C | D | E | F | G | H | I | J |
|---|---|---|---|---|---|---|---|---|---|
| 1777 | N | PHE | A | 348 | -29.028 | 44.146 | 93.635 | 1.00 | 33.51 |
| 1778 | CA | PHE | A | 348 | -27.835 | 44.911 | 93.268 | 1.00 | 33.28 |
| 1779 | CB | PHE | A | 348 | -28.204 | 45.979 | 92.254 | 1.00 | 32.67 |
| 1780 | CG | PHE | A | 348 | -28.626 | 45.454 | 90.940 | 1.00 | 31.24 |
| 1781 | CD1 | PHE | A | 348 | -29.962 | 45.538 | 90.551 | 1.00 | 32.35 |
| 1782 | CE1 | PHE | A | 348 | -30.374 | 45.068 | 89.325 | 1.00 | 31.74 |
| 1783 | CZ | PHE | A | 348 | -29.433 | 44.491 | 88.447 | 1.00 | 30.42 |
| 1784 | CE2 | PHE | A | 348 | -28.090 | 44.411 | 88.822 | 1.00 | 32.15 |
| 1785 | CD2 | PHE | A | 348 | -27.695 | 44.892 | 90.070 | 1.00 | 30.97 |
| 1786 | C | PHE | A | 348 | -27.337 | 45.701 | 94.453 | 1.00 | 35.77 |
| 1787 | O | PHE | A | 348 | -28.126 | 46.255 | 95.209 | 1.00 | 35.76 |
| 1788 | N | PRO | A | 349 | -26.025 | 45.772 | 94.628 | 1.00 | 36.99 |
| 1789 | CA | PRO | A | 349 | -25.493 | 46.699 | 95.626 | 1.00 | 37.46 |
| 1790 | CB | PRO | A | 349 | -23.963 | 46.485 | 95.567 | 1.00 | 38.56 |
| 1791 | CG | PRO | A | 349 | -23.670 | 45.526 | 94.471 | 1.00 | 37.30 |
| 1792 | CD | PRO | A | 349 | -24.990 | 45.029 | 93.906 | 1.00 | 37.24 |
| 1793 | C | PRO | A | 349 | -25.883 | 48.098 | 95.159 | 1.00 | 37.57 |
| 1794 | O | PRO | A | 349 | -26.153 | 48.337 | 93.990 | 1.00 | 36.04 |
| 1795 | N | ASP | A | 350 | -25.921 | 49.055 | 96.076 | 1.00 | 39.36 |
| 1796 | CA | ASP | A | 350 | -26.257 | 50.422 | 95.693 | 1.00 | 40.98 |
| 1797 | CB | ASP | A | 350 | -26.206 | 51.348 | 96.903 | 1.00 | 42.59 |
| 1798 | CG | ASP | A | 350 | -27.260 | 51.031 | 97.914 | 1.00 | 47.11 |
| 1799 | OD1 | ASP | A | 350 | -27.128 | 51.620 | 99.016 | 1.00 | 53.92 |
| 1800 | OD2 | ASP | A | 350 | -28.222 | 50.225 | 97.689 | 1.00 | 50.42 |
| 1801 | C | ASP | A | 350 | -25.351 | 51.058 | 94.663 | 1.00 | 40.13 |
| 1802 | O | ASP | A | 350 | -25.814 | 51.905 | 93.909 | 1.00 | 40.28 |
| 1803 | N | PHE | A | 351 | -24.063 | 50.736 | 94.649 | 1.00 | 39.85 |
| 1804 | CA | PHE | A | 351 | -23.202 | 51.402 | 93.673 | 1.00 | 39.47 |
| 1805 | CB | PHE | A | 351 | -21.718 | 51.213 | 93.957 | 1.00 | 40.21 |
| 1806 | CG | PHE | A | 351 | -21.278 | 49.784 | 93.967 | 1.00 | 41.11 |
| 1807 | CD1 | PHE | A | 351 | -21.221 | 49.082 | 95.162 | 1.00 | 39.89 |
| 1808 | CE1 | PHE | A | 351 | -20.833 | 47.761 | 95.192 | 1.00 | 40.56 |
| 1809 | CZ | PHE | A | 351 | -20.521 | 47.111 | 93.978 | 1.00 | 42.46 |
| 1810 | CE2 | PHE | A | 351 | -20.589 | 47.826 | 92.772 | 1.00 | 39.35 |
| 1811 | CD2 | PHE | A | 351 | -20.977 | 49.124 | 92.767 | 1.00 | 41.22 |
| 1812 | C | PHE | A | 351 | -23.543 | 51.116 | 92.213 | 1.00 | 40.90 |
| 1813 | O | PHE | A | 351 | -23.177 | 51.889 | 91.325 | 1.00 | 41.02 |
| 1814 | N | VAL | A | 352 | -24.278 | 50.042 | 91.927 | 1.00 | 39.58 |
| 1815 | CA | VAL | A | 352 | -24.604 | 49.759 | 90.531 | 1.00 | 38.85 |
| 1816 | CB | VAL | A | 352 | -25.223 | 48.351 | 90.345 | 1.00 | 37.90 |
| 1817 | CG1 | VAL | A | 352 | -25.491 | 48.084 | 88.893 | 1.00 | 36.19 |
| 1818 | CG2 | VAL | A | 352 | -24.271 | 47.308 | 90.902 | 1.00 | 38.04 |
| 1819 | C | VAL | A | 352 | -25.531 | 50.764 | 89.905 | 1.00 | 39.39 |
| 1820 | O | VAL | A | 352 | -26.631 | 50.985 | 90.420 | 1.00 | 38.87 |
| 1821 | N | THR | A | 353 | -25.136 | 51.309 | 88.742 | 1.00 | 40.16 |
| 1822 | CA | THR | A | 353 | -25.943 | 52.332 | 88.057 | 1.00 | 40.56 |
| 1823 | CB | THR | A | 353 | -25.127 | 53.080 | 86.987 | 1.00 | 41.20 |
| 1824 | OG1 | THR | A | 353 | -24.703 | 52.160 | 85.970 | 1.00 | 39.47 |
| 1825 | CG2 | THR | A | 353 | -23.893 | 53.625 | 87.588 | 1.00 | 39.13 |
| 1826 | C | THR | A | 353 | -27.216 | 51.852 | 87.400 | 1.00 | 41.64 |
| 1827 | O | THR | A | 353 | -27.424 | 50.664 | 87.152 | 1.00 | 41.19 |

FIGURE 3AJ

| A | B | C | D | E | F | G | H | I | J |
|---|---|---|---|---|---|---|---|---|---|
| 1828 | N | GLU | A | 354 | -28.071 | 52.816 | 87.102 | 1.00 | 41.67 |
| 1829 | CA | GLU | A | 354 | -29.321 | 52.514 | 86.485 | 1.00 | 43.44 |
| 1830 | CB | GLU | A | 354 | -30.191 | 53.770 | 86.372 | 1.00 | 46.05 |
| 1831 | CG | GLU | A | 354 | -30.592 | 54.252 | 87.751 | 1.00 | 54.41 |
| 1832 | CD | GLU | A | 354 | -30.894 | 53.090 | 88.684 | 1.00 | 64.52 |
| 1833 | OE1 | GLU | A | 354 | -32.014 | 52.505 | 88.550 | 1.00 | 68.68 |
| 1834 | OE2 | GLU | A | 354 | -30.038 | 52.775 | 89.551 | 1.00 | 67.34 |
| 1835 | C | GLU | A | 354 | -29.168 | 51.828 | 85.156 | 1.00 | 41.54 |
| 1836 | O | GLU | A | 354 | -29.908 | 50.900 | 84.858 | 1.00 | 40.38 |
| 1837 | N | GLY | A | 355 | -28.226 | 52.291 | 84.353 | 1.00 | 40.21 |
| 1838 | CA | GLY | A | 355 | -28.041 | 51.714 | 83.044 | 1.00 | 37.79 |
| 1839 | C | GLY | A | 355 | -27.598 | 50.271 | 83.170 | 1.00 | 36.84 |
| 1840 | O | GLY | A | 355 | -28.060 | 49.403 | 82.423 | 1.00 | 37.14 |
| 1841 | N | ALA | A | 356 | -26.684 | 50.016 | 84.092 | 1.00 | 36.29 |
| 1842 | CA | ALA | A | 356 | -26.178 | 48.669 | 84.268 | 1.00 | 36.41 |
| 1843 | CB | ALA | A | 356 | -24.998 | 48.660 | 85.206 | 1.00 | 35.64 |
| 1844 | C | ALA | A | 356 | -27.295 | 47.794 | 84.782 | 1.00 | 35.70 |
| 1845 | O | ALA | A | 356 | -27.490 | 46.695 | 84.309 | 1.00 | 34.90 |
| 1846 | N | ARG | A | 357 | -28.072 | 48.293 | 85.745 | 1.00 | 36.25 |
| 1847 | CA | ARG | A | 357 | -29.186 | 47.504 | 86.264 | 1.00 | 36.61 |
| 1848 | CB | ARG | A | 357 | -29.960 | 48.250 | 87.339 | 1.00 | 36.86 |
| 1849 | CG | ARG | A | 357 | -29.169 | 48.482 | 88.582 | 1.00 | 34.77 |
| 1850 | CD | ARG | A | 357 | -29.988 | 49.289 | 89.609 | 1.00 | 37.61 |
| 1851 | NE | ARG | A | 357 | -29.112 | 49.640 | 90.708 | 1.00 | 36.40 |
| 1852 | CZ | ARG | A | 357 | -29.400 | 49.468 | 91.975 | 1.00 | 35.35 |
| 1853 | NH1 | ARG | A | 357 | -30.572 | 48.952 | 92.320 | 1.00 | 39.15 |
| 1854 | NH2 | ARG | A | 357 | -28.498 | 49.787 | 92.890 | 1.00 | 33.56 |
| 1855 | C | ARG | A | 357 | -30.165 | 47.167 | 85.172 | 1.00 | 37.12 |
| 1856 | O | ARG | A | 357 | -30.718 | 46.074 | 85.153 | 1.00 | 37.21 |
| 1857 | N | ASP | A | 358 | -30.420 | 48.132 | 84.297 | 1.00 | 37.24 |
| 1858 | CA | ASP | A | 358 | -31.353 | 47.925 | 83.226 | 1.00 | 37.93 |
| 1859 | CB | ASP | A | 358 | -31.614 | 49.202 | 82.454 | 1.00 | 38.87 |
| 1860 | CG | ASP | A | 358 | -32.621 | 48.984 | 81.324 | 1.00 | 42.76 |
| 1861 | OD1 | ASP | A | 358 | -33.846 | 49.000 | 81.602 | 1.00 | 46.16 |
| 1862 | OD2 | ASP | A | 358 | -32.290 | 48.788 | 80.126 | 1.00 | 45.46 |
| 1863 | C | ASP | A | 358 | -30.868 | 46.836 | 82.281 | 1.00 | 36.98 |
| 1864 | O | ASP | A | 358 | -31.656 | 45.967 | 81.884 | 1.00 | 36.97 |
| 1865 | N | LEU | A | 359 | -29.578 | 46.860 | 81.942 | 1.00 | 35.72 |
| 1866 | CA | LEU | A | 359 | -29.042 | 45.867 | 81.031 | 1.00 | 35.51 |
| 1867 | CB | LEU | A | 359 | -27.595 | 46.168 | 80.713 | 1.00 | 35.38 |
| 1868 | CG | LEU | A | 359 | -27.063 | 45.779 | 79.327 | 1.00 | 39.30 |
| 1869 | CD1 | LEU | A | 359 | -25.507 | 45.577 | 79.301 | 1.00 | 37.82 |
| 1870 | CD2 | LEU | A | 359 | -27.787 | 44.681 | 78.634 | 1.00 | 35.07 |
| 1871 | C | LEU | A | 359 | -29.127 | 44.477 | 81.657 | 1.00 | 33.71 |
| 1872 | O | LEU | A | 359 | -29.575 | 43.515 | 81.028 | 1.00 | 32.97 |
| 1873 | N | ILE | A | 360 | -28.679 | 44.388 | 82.900 | 1.00 | 32.44 |
| 1874 | CA | ILE | A | 360 | -28.646 | 43.105 | 83.610 | 1.00 | 31.57 |
| 1875 | CB | ILE | A | 360 | -27.847 | 43.253 | 84.926 | 1.00 | 31.85 |
| 1876 | CG1 | ILE | A | 360 | -26.367 | 43.490 | 84.572 | 1.00 | 32.47 |
| 1877 | CD1 | ILE | A | 360 | -25.639 | 44.299 | 85.549 | 1.00 | 29.24 |
| 1878 | CG2 | ILE | A | 360 | -27.934 | 41.956 | 85.801 | 1.00 | 30.72 |

FIGURE 3AK

| A | B | C | D | E | F | G | H | I | J |
|---|---|---|---|---|---|---|---|---|---|
| 1879 | C | ILE | A | 360 | -30.053 | 42.521 | 83.830 | 1.00 | 32.40 |
| 1880 | O | ILE | A | 360 | -30.265 | 41.308 | 83.611 | 1.00 | 31.17 |
| 1881 | N | SER | A | 361 | -30.996 | 43.386 | 84.214 | 1.00 | 32.23 |
| 1882 | CA | SER | A | 361 | -32.363 | 42.958 | 84.445 | 1.00 | 34.85 |
| 1883 | CB | SER | A | 361 | -33.223 | 44.060 | 85.087 | 1.00 | 35.23 |
| 1884 | OG | SER | A | 361 | -32.814 | 44.245 | 86.443 | 1.00 | 40.29 |
| 1885 | C | SER | A | 361 | -32.969 | 42.457 | 83.143 | 1.00 | 34.58 |
| 1886 | O | SER | A | 361 | -33.734 | 41.528 | 83.147 | 1.00 | 34.46 |
| 1887 | N | ARG | A | 362 | -32.571 | 43.020 | 82.017 | 1.00 | 35.27 |
| 1888 | CA | ARG | A | 362 | -33.116 | 42.553 | 80.736 | 1.00 | 35.84 |
| 1889 | CB | ARG | A | 362 | -32.908 | 43.595 | 79.653 | 1.00 | 36.24 |
| 1890 | CG | ARG | A | 362 | -33.797 | 44.805 | 79.768 | 1.00 | 42.24 |
| 1891 | CD | ARG | A | 362 | -33.312 | 46.000 | 78.930 | 1.00 | 48.93 |
| 1892 | NE | ARG | A | 362 | -34.160 | 47.177 | 79.139 | 1.00 | 57.80 |
| 1893 | CZ | ARG | A | 362 | -34.932 | 47.717 | 78.208 | 1.00 | 63.64 |
| 1894 | NH1 | ARG | A | 362 | -34.931 | 47.208 | 76.972 | 1.00 | 67.52 |
| 1895 | NH2 | ARG | A | 362 | -35.696 | 48.771 | 78.502 | 1.00 | 65.50 |
| 1896 | C | ARG | A | 362 | -32.525 | 41.220 | 80.283 | 1.00 | 35.03 |
| 1897 | O | ARG | A | 362 | -33.216 | 40.429 | 79.634 | 1.00 | 36.42 |
| 1898 | N | LEU | A | 363 | -31.279 | 40.939 | 80.664 | 1.00 | 32.41 |
| 1899 | CA | LEU | A | 363 | -30.645 | 39.705 | 80.279 | 1.00 | 32.03 |
| 1900 | CB | LEU | A | 363 | -29.133 | 39.896 | 80.329 | 1.00 | 31.58 |
| 1901 | CG | LEU | A | 363 | -28.234 | 40.365 | 79.163 | 1.00 | 34.89 |
| 1902 | CD1 | LEU | A | 363 | -28.757 | 40.467 | 77.803 | 1.00 | 36.09 |
| 1903 | CD2 | LEU | A | 363 | -27.243 | 41.450 | 79.528 | 1.00 | 34.69 |
| 1904 | C | LEU | A | 363 | -31.027 | 38.572 | 81.203 | 1.00 | 32.15 |
| 1905 | O | LEU | A | 363 | -31.111 | 37.430 | 80.776 | 1.00 | 33.41 |
| 1906 | N | LEU | A | 364 | -31.268 | 38.857 | 82.472 | 1.00 | 31.16 |
| 1907 | CA | LEU | A | 364 | -31.571 | 37.770 | 83.428 | 1.00 | 32.01 |
| 1908 | CB | LEU | A | 364 | -30.963 | 38.067 | 84.804 | 1.00 | 31.60 |
| 1909 | CG | LEU | A | 364 | -29.420 | 38.146 | 84.738 | 1.00 | 31.16 |
| 1910 | CD1 | LEU | A | 364 | -28.840 | 38.468 | 86.102 | 1.00 | 34.77 |
| 1911 | CD2 | LEU | A | 364 | -28.841 | 36.783 | 84.213 | 1.00 | 31.53 |
| 1912 | C | LEU | A | 364 | -33.088 | 37.535 | 83.500 | 1.00 | 33.63 |
| 1913 | O | LEU | A | 364 | -33.734 | 37.811 | 84.487 | 1.00 | 33.26 |
| 1914 | N | LYS | A | 365 | -33.662 | 37.065 | 82.410 | 1.00 | 33.41 |
| 1915 | CA | LYS | A | 365 | -35.082 | 36.796 | 82.393 | 1.00 | 35.64 |
| 1916 | CB | LYS | A | 365 | -35.718 | 37.369 | 81.135 | 1.00 | 35.84 |
| 1917 | CG | LYS | A | 365 | -35.929 | 38.880 | 81.125 | 1.00 | 39.34 |
| 1918 | CD | LYS | A | 365 | -36.633 | 39.297 | 82.400 | 1.00 | 46.53 |
| 1919 | CE | LYS | A | 365 | -37.698 | 40.335 | 82.107 | 1.00 | 49.18 |
| 1920 | NZ | LYS | A | 365 | -37.064 | 41.556 | 81.577 | 1.00 | 54.14 |
| 1921 | C | LYS | A | 365 | -35.216 | 35.299 | 82.375 | 1.00 | 35.57 |
| 1922 | O | LYS | A | 365 | -34.516 | 34.626 | 81.599 | 1.00 | 34.77 |
| 1923 | N | HIS | A | 366 | -36.084 | 34.780 | 83.241 | 1.00 | 34.63 |
| 1924 | CA | HIS | A | 366 | -36.339 | 33.372 | 83.302 | 1.00 | 36.28 |
| 1925 | CB | HIS | A | 366 | -37.437 | 33.047 | 84.346 | 1.00 | 35.81 |
| 1926 | CG | HIS | A | 366 | -37.567 | 31.581 | 84.590 | 1.00 | 39.29 |
| 1927 | ND1 | HIS | A | 366 | -38.186 | 30.728 | 83.693 | 1.00 | 41.29 |
| 1928 | CE1 | HIS | A | 366 | -38.111 | 29.487 | 84.145 | 1.00 | 40.54 |
| 1929 | NE2 | HIS | A | 366 | -37.446 | 29.500 | 85.291 | 1.00 | 42.19 |

FIGURE 3AL

| A | B | C | D | E | F | G | H | I | J |
|---|---|---|---|---|---|---|---|---|---|
| 1930 | CD2 | HIS | A | 366 | -37.088 | 30.796 | 85.587 | 1.00 | 39.35 |
| 1931 | C | HIS | A | 366 | -36.789 | 32.856 | 81.911 | 1.00 | 37.30 |
| 1932 | O | HIS | A | 366 | -36.356 | 31.798 | 81.435 | 1.00 | 36.00 |
| 1933 | N | ASN | A | 367 | -37.684 | 33.573 | 81.261 | 1.00 | 38.00 |
| 1934 | CA | ASN | A | 367 | -38.095 | 33.069 | 79.937 | 1.00 | 40.10 |
| 1935 | CB | ASN | A | 367 | -39.487 | 33.598 | 79.658 | 1.00 | 40.85 |
| 1936 | CG | ASN | A | 367 | -40.080 | 33.074 | 78.380 | 1.00 | 44.28 |
| 1937 | OD1 | ASN | A | 367 | -41.276 | 33.219 | 78.172 | 1.00 | 51.80 |
| 1938 | ND2 | ASN | A | 367 | -39.271 | 32.476 | 77.525 | 1.00 | 46.36 |
| 1939 | C | ASN | A | 367 | -37.086 | 33.524 | 78.875 | 1.00 | 39.35 |
| 1940 | O | ASN | A | 367 | -36.961 | 34.709 | 78.683 | 1.00 | 38.80 |
| 1941 | N | PRO | A | 368 | -36.397 | 32.591 | 78.210 | 1.00 | 39.49 |
| 1942 | CA | PRO | A | 368 | -35.336 | 32.903 | 77.238 | 1.00 | 40.08 |
| 1943 | CB | PRO | A | 368 | -34.976 | 31.536 | 76.624 | 1.00 | 39.29 |
| 1944 | CG | PRO | A | 368 | -35.451 | 30.502 | 77.567 | 1.00 | 40.15 |
| 1945 | CD | PRO | A | 368 | -36.633 | 31.136 | 78.295 | 1.00 | 40.09 |
| 1946 | C | PRO | A | 368 | -35.824 | 33.807 | 76.112 | 1.00 | 40.68 |
| 1947 | O | PRO | A | 368 | -35.082 | 34.684 | 75.656 | 1.00 | 38.95 |
| 1948 | N | SER | A | 369 | -37.064 | 33.592 | 75.664 | 1.00 | 42.38 |
| 1949 | CA | SER | A | 369 | -37.639 | 34.437 | 74.597 | 1.00 | 43.99 |
| 1950 | CB | SER | A | 369 | -39.033 | 33.951 | 74.203 | 1.00 | 44.88 |
| 1951 | OG | SER | A | 369 | -38.956 | 32.601 | 73.740 | 1.00 | 48.55 |
| 1952 | C | SER | A | 369 | -37.742 | 35.894 | 74.995 | 1.00 | 44.04 |
| 1953 | O | SER | A | 369 | -37.889 | 36.754 | 74.140 | 1.00 | 44.29 |
| 1954 | N | GLN | A | 370 | -37.692 | 36.186 | 76.295 | 1.00 | 44.21 |
| 1955 | CA | GLN | A | 370 | -37.719 | 37.591 | 76.721 | 1.00 | 45.13 |
| 1956 | CB | GLN | A | 370 | -38.437 | 37.739 | 78.053 | 1.00 | 45.55 |
| 1957 | CG | GLN | A | 370 | -39.839 | 37.121 | 77.994 | 1.00 | 50.14 |
| 1958 | CD | GLN | A | 370 | -40.602 | 37.264 | 79.300 | 1.00 | 56.48 |
| 1959 | OE1 | GLN | A | 370 | -41.679 | 36.646 | 79.474 | 1.00 | 60.38 |
| 1960 | NE2 | GLN | A | 370 | -40.060 | 38.056 | 80.230 | 1.00 | 55.95 |
| 1961 | C | GLN | A | 370 | -36.332 | 38.231 | 76.806 | 1.00 | 44.45 |
| 1962 | O | GLN | A | 370 | -36.210 | 39.423 | 77.063 | 1.00 | 44.24 |
| 1963 | N | ARG | A | 371 | -35.285 | 37.430 | 76.631 | 1.00 | 43.95 |
| 1964 | CA | ARG | A | 371 | -33.915 | 37.962 | 76.693 | 1.00 | 43.01 |
| 1965 | CB | ARG | A | 371 | -32.911 | 36.827 | 76.882 | 1.00 | 42.30 |
| 1966 | CG | ARG | A | 371 | -32.994 | 36.206 | 78.279 | 1.00 | 36.93 |
| 1967 | CD | ARG | A | 371 | -32.118 | 35.032 | 78.477 | 1.00 | 33.96 |
| 1968 | NE | ARG | A | 371 | -32.732 | 34.134 | 79.452 | 1.00 | 33.75 |
| 1969 | CZ | ARG | A | 371 | -32.561 | 32.828 | 79.521 | 1.00 | 32.13 |
| 1970 | NH1 | ARG | A | 371 | -33.243 | 32.141 | 80.440 | 1.00 | 33.40 |
| 1971 | NH2 | ARG | A | 371 | -31.717 | 32.197 | 78.702 | 1.00 | 30.58 |
| 1972 | C | ARG | A | 371 | -33.641 | 38.717 | 75.406 | 1.00 | 42.92 |
| 1973 | O | ARG | A | 371 | -34.115 | 38.306 | 74.374 | 1.00 | 43.48 |
| 1974 | N | PRO | A | 372 | -32.927 | 39.831 | 75.459 | 1.00 | 43.09 |
| 1975 | CA | PRO | A | 372 | -32.678 | 40.611 | 74.234 | 1.00 | 42.76 |
| 1976 | CB | PRO | A | 372 | -31.890 | 41.837 | 74.717 | 1.00 | 43.00 |
| 1977 | CG | PRO | A | 372 | -31.590 | 41.648 | 76.178 | 1.00 | 42.62 |
| 1978 | CD | PRO | A | 372 | -32.371 | 40.456 | 76.678 | 1.00 | 43.28 |
| 1979 | C | PRO | A | 372 | -31.829 | 39.874 | 73.226 | 1.00 | 43.31 |
| 1980 | O | PRO | A | 372 | -31.191 | 38.862 | 73.545 | 1.00 | 43.24 |

FIGURE 3AM

| A | B | C | D | E | F | G | H | I | J |
|---|---|---|---|---|---|---|---|---|---|
| 1981 | N | MET | A | 373 | -31.820 | 40.378 | 71.995 | 1.00 | 43.19 |
| 1982 | CA | MET | A | 373 | -30.928 | 39.857 | 70.976 | 1.00 | 43.50 |
| 1983 | CB | MET | A | 373 | -31.448 | 40.174 | 69.585 | 1.00 | 44.61 |
| 1984 | CG | MET | A | 373 | -32.688 | 39.421 | 69.205 | 1.00 | 50.78 |
| 1985 | SD | MET | A | 373 | -33.173 | 39.941 | 67.576 | 1.00 | 64.15 |
| 1986 | CE | MET | A | 373 | -32.985 | 41.823 | 67.726 | 1.00 | 59.77 |
| 1987 | C | MET | A | 373 | -29.564 | 40.516 | 71.172 | 1.00 | 42.00 |
| 1988 | O | MET | A | 373 | -29.452 | 41.539 | 71.841 | 1.00 | 39.32 |
| 1989 | N | LEU | A | 374 | -28.526 | 39.926 | 70.597 | 1.00 | 41.82 |
| 1990 | CA | LEU | A | 374 | -27.188 | 40.488 | 70.727 | 1.00 | 43.13 |
| 1991 | CB | LEU | A | 374 | -26.194 | 39.605 | 70.025 | 1.00 | 43.22 |
| 1992 | CG | LEU | A | 374 | -25.814 | 38.411 | 70.923 | 1.00 | 45.40 |
| 1993 | CD1 | LEU | A | 374 | -24.780 | 37.453 | 70.278 | 1.00 | 44.95 |
| 1994 | CD2 | LEU | A | 374 | -25.284 | 38.861 | 72.288 | 1.00 | 41.96 |
| 1995 | C | LEU | A | 374 | -27.192 | 41.923 | 70.171 | 1.00 | 43.85 |
| 1996 | O | LEU | A | 374 | -26.478 | 42.788 | 70.667 | 1.00 | 43.31 |
| 1997 | N | ALA | A | 375 | -27.951 | 42.152 | 69.118 | 1.00 | 43.58 |
| 1998 | CA | ALA | A | 375 | -27.979 | 43.472 | 68.494 | 1.00 | 44.11 |
| 1999 | CB | ALA | A | 375 | -29.028 | 43.491 | 67.388 | 1.00 | 43.88 |
| 2000 | C | ALA | A | 375 | -28.336 | 44.516 | 69.517 | 1.00 | 43.69 |
| 2001 | O | ALA | A | 375 | -27.783 | 45.616 | 69.548 | 1.00 | 45.16 |
| 2002 | N | GLU | A | 376 | -29.265 | 44.123 | 70.370 | 1.00 | 43.44 |
| 2003 | CA | GLU | A | 376 | -29.855 | 44.996 | 71.354 | 1.00 | 43.12 |
| 2004 | CB | GLU | A | 376 | -31.147 | 44.357 | 71.836 | 1.00 | 43.67 |
| 2005 | CG | GLU | A | 376 | -32.103 | 44.068 | 70.705 | 1.00 | 49.90 |
| 2006 | CD | GLU | A | 376 | -33.520 | 43.811 | 71.206 | 1.00 | 57.55 |
| 2007 | OE1 | GLU | A | 376 | -33.691 | 42.679 | 71.699 | 1.00 | 56.12 |
| 2008 | OE2 | GLU | A | 376 | -34.454 | 44.705 | 71.124 | 1.00 | 60.58 |
| 2009 | C | GLU | A | 376 | -28.969 | 45.306 | 72.529 | 1.00 | 41.38 |
| 2010 | O | GLU | A | 376 | -29.116 | 46.343 | 73.152 | 1.00 | 42.50 |
| 2011 | N | VAL | A | 377 | -28.059 | 44.394 | 72.850 | 1.00 | 39.33 |
| 2012 | CA | VAL | A | 377 | -27.116 | 44.602 | 73.948 | 1.00 | 37.51 |
| 2013 | CB | VAL | A | 377 | -26.405 | 43.276 | 74.328 | 1.00 | 36.63 |
| 2014 | CG1 | VAL | A | 377 | -25.281 | 43.536 | 75.284 | 1.00 | 35.55 |
| 2015 | CG2 | VAL | A | 377 | -27.416 | 42.254 | 74.883 | 1.00 | 37.26 |
| 2016 | C | VAL | A | 377 | -26.043 | 45.547 | 73.449 | 1.00 | 37.40 |
| 2017 | O | VAL | A | 377 | -25.604 | 46.436 | 74.147 | 1.00 | 37.91 |
| 2018 | N | LEU | A | 378 | -25.621 | 45.323 | 72.219 | 1.00 | 37.51 |
| 2019 | CA | LEU | A | 378 | -24.580 | 46.115 | 71.589 | 1.00 | 39.81 |
| 2020 | CB | LEU | A | 378 | -24.266 | 45.532 | 70.217 | 1.00 | 40.42 |
| 2021 | CG | LEU | A | 378 | -23.393 | 44.286 | 70.335 | 1.00 | 41.70 |
| 2022 | CD1 | LEU | A | 378 | -23.067 | 43.658 | 68.983 | 1.00 | 46.77 |
| 2023 | CD2 | LEU | A | 378 | -22.130 | 44.678 | 71.057 | 1.00 | 37.23 |
| 2024 | C | LEU | A | 378 | -24.946 | 47.580 | 71.442 | 1.00 | 41.32 |
| 2025 | O | LEU | A | 378 | -24.075 | 48.445 | 71.358 | 1.00 | 42.45 |
| 2026 | N | GLU | A | 379 | -26.244 | 47.845 | 71.421 | 1.00 | 41.71 |
| 2027 | CA | GLU | A | 379 | -26.719 | 49.178 | 71.213 | 1.00 | 42.63 |
| 2028 | CB | GLU | A | 379 | -27.670 | 49.206 | 70.018 | 1.00 | 44.54 |
| 2029 | CG | GLU | A | 379 | -26.995 | 48.791 | 68.724 | 1.00 | 47.20 |
| 2030 | CD | GLU | A | 379 | -27.923 | 48.707 | 67.527 | 1.00 | 56.88 |
| 2031 | OE1 | GLU | A | 379 | -29.177 | 48.664 | 67.706 | 1.00 | 59.40 |

FIGURE 3AN

| A | B | C | D | E | F | G | H | I | J |
|---|---|---|---|---|---|---|---|---|---|
| 2032 | OE2 | GLU | A | 379 | -27.372 | 48.665 | 66.389 | 1.00 | 61.82 |
| 2033 | C | GLU | A | 379 | -27.401 | 49.692 | 72.460 | 1.00 | 43.14 |
| 2034 | O | GLU | A | 379 | -28.071 | 50.749 | 72.435 | 1.00 | 43.40 |
| 2035 | N | HIS | A | 380 | -27.244 | 48.966 | 73.575 | 1.00 | 41.24 |
| 2036 | CA | HIS | A | 380 | -27.851 | 49.440 | 74.793 | 1.00 | 40.10 |
| 2037 | CB | HIS | A | 380 | -27.681 | 48.393 | 75.915 | 1.00 | 39.60 |
| 2038 | CG | HIS | A | 380 | -28.332 | 48.789 | 77.191 | 1.00 | 38.52 |
| 2039 | ND1 | HIS | A | 380 | -29.551 | 48.279 | 77.590 | 1.00 | 40.40 |
| 2040 | CE1 | HIS | A | 380 | -29.890 | 48.824 | 78.747 | 1.00 | 37.68 |
| 2041 | NE2 | HIS | A | 380 | -28.923 | 49.643 | 79.122 | 1.00 | 39.48 |
| 2042 | CD2 | HIS | A | 380 | -27.942 | 49.644 | 78.160 | 1.00 | 34.37 |
| 2043 | C | HIS | A | 380 | -27.163 | 50.747 | 75.172 | 1.00 | 39.36 |
| 2044 | O | HIS | A | 380 | -25.985 | 50.841 | 75.006 | 1.00 | 39.34 |
| 2045 | N | PRO | A | 381 | -27.882 | 51.732 | 75.713 | 1.00 | 40.21 |
| 2046 | CA | PRO | A | 381 | -27.277 | 53.041 | 75.975 | 1.00 | 40.19 |
| 2047 | CB | PRO | A | 381 | -28.439 | 53.885 | 76.518 | 1.00 | 40.84 |
| 2048 | CG | PRO | A | 381 | -29.677 | 53.167 | 76.093 | 1.00 | 42.96 |
| 2049 | CD | PRO | A | 381 | -29.307 | 51.702 | 76.106 | 1.00 | 40.74 |
| 2050 | C | PRO | A | 381 | -26.165 | 52.971 | 77.002 | 1.00 | 39.71 |
| 2051 | O | PRO | A | 381 | -25.239 | 53.739 | 76.860 | 1.00 | 38.49 |
| 2052 | N | TRP | A | 382 | -26.267 | 52.094 | 78.015 | 1.00 | 37.20 |
| 2053 | CA | TRP | A | 382 | -25.213 | 51.967 | 79.007 | 1.00 | 36.17 |
| 2054 | CB | TRP | A | 382 | -25.638 | 51.046 | 80.145 | 1.00 | 34.80 |
| 2055 | CG | TRP | A | 382 | -24.604 | 50.947 | 81.203 | 1.00 | 35.01 |
| 2056 | CD1 | TRP | A | 382 | -24.349 | 51.852 | 82.170 | 1.00 | 36.17 |
| 2057 | NE1 | TRP | A | 382 | -23.326 | 51.402 | 82.975 | 1.00 | 39.89 |
| 2058 | CE2 | TRP | A | 382 | -22.895 | 50.191 | 82.505 | 1.00 | 36.83 |
| 2059 | CD2 | TRP | A | 382 | -23.684 | 49.879 | 81.391 | 1.00 | 34.51 |
| 2060 | CE3 | TRP | A | 382 | -23.437 | 48.680 | 80.716 | 1.00 | 37.27 |
| 2061 | CZ3 | TRP | A | 382 | -22.450 | 47.843 | 81.185 | 1.00 | 35.85 |
| 2062 | CH2 | TRP | A | 382 | -21.675 | 48.196 | 82.283 | 1.00 | 34.82 |
| 2063 | CZ2 | TRP | A | 382 | -21.887 | 49.357 | 82.966 | 1.00 | 32.53 |
| 2064 | C | TRP | A | 382 | -23.940 | 51.436 | 78.346 | 1.00 | 36.25 |
| 2065 | O | TRP | A | 382 | -22.833 | 51.887 | 78.657 | 1.00 | 36.89 |
| 2066 | N | ILE | A | 383 | -24.090 | 50.456 | 77.472 | 1.00 | 36.03 |
| 2067 | CA | ILE | A | 383 | -22.943 | 49.924 | 76.734 | 1.00 | 36.79 |
| 2068 | CB | ILE | A | 383 | -23.373 | 48.683 | 75.892 | 1.00 | 36.16 |
| 2069 | CG1 | ILE | A | 383 | -23.751 | 47.476 | 76.802 | 1.00 | 34.61 |
| 2070 | CD1 | ILE | A | 383 | -22.522 | 46.916 | 77.531 | 1.00 | 34.04 |
| 2071 | CG2 | ILE | A | 383 | -22.221 | 48.209 | 75.038 | 1.00 | 35.05 |
| 2072 | C | ILE | A | 383 | -22.377 | 51.014 | 75.804 | 1.00 | 39.31 |
| 2073 | O | ILE | A | 383 | -21.172 | 51.250 | 75.708 | 1.00 | 40.13 |
| 2074 | N | THR | A | 384 | -23.268 | 51.707 | 75.130 | 1.00 | 41.29 |
| 2075 | CA | THR | A | 384 | -22.849 | 52.781 | 74.221 | 1.00 | 44.28 |
| 2076 | CB | THR | A | 384 | -24.120 | 53.418 | 73.673 | 1.00 | 44.01 |
| 2077 | OG1 | THR | A | 384 | -24.539 | 52.622 | 72.568 | 1.00 | 48.12 |
| 2078 | CG2 | THR | A | 384 | -23.822 | 54.750 | 73.090 | 1.00 | 49.09 |
| 2079 | C | THR | A | 384 | -22.006 | 53.846 | 74.885 | 1.00 | 43.49 |
| 2080 | O | THR | A | 384 | -20.980 | 54.271 | 74.359 | 1.00 | 46.02 |
| 2081 | N | ALA | A | 385 | -22.449 | 54.281 | 76.044 | 1.00 | 42.28 |
| 2082 | CA | ALA | A | 385 | -21.779 | 55.332 | 76.763 | 1.00 | 42.24 |

FIGURE 3AO

| A | B | C | D | E | F | G | H | I | J |
|---|---|---|---|---|---|---|---|---|---|
| 2083 | CB | ALA | A | 385 | -22.705 | 55.884 | 77.823 | 1.00 | 41.95 |
| 2084 | C | ALA | A | 385 | -20.509 | 54.897 | 77.424 | 1.00 | 42.41 |
| 2085 | O | ALA | A | 385 | -19.606 | 55.728 | 77.660 | 1.00 | 43.21 |
| 2086 | N | ASN | A | 386 | -20.404 | 53.612 | 77.749 | 1.00 | 40.11 |
| 2087 | CA | ASN | A | 386 | -19.254 | 53.178 | 78.478 | 1.00 | 38.95 |
| 2088 | CB | ASN | A | 386 | -19.696 | 52.453 | 79.740 | 1.00 | 39.05 |
| 2089 | CG | ASN | A | 386 | -20.371 | 53.392 | 80.739 | 1.00 | 39.22 |
| 2090 | OD1 | ASN | A | 386 | -19.698 | 54.080 | 81.495 | 1.00 | 40.98 |
| 2091 | ND2 | ASN | A | 386 | -21.695 | 53.396 | 80.754 | 1.00 | 40.56 |
| 2092 | C | ASN | A | 386 | -18.195 | 52.366 | 77.760 | 1.00 | 38.55 |
| 2093 | O | ASN | A | 386 | -17.077 | 52.329 | 78.212 | 1.00 | 37.05 |
| 2094 | N | SER | A | 387 | -18.545 | 51.701 | 76.682 | 1.00 | 39.28 |
| 2095 | CA | SER | A | 387 | -17.604 | 50.833 | 75.997 | 1.00 | 41.73 |
| 2096 | CB | SER | A | 387 | -18.322 | 49.922 | 75.010 | 1.00 | 40.55 |
| 2097 | OG | SER | A | 387 | -17.359 | 49.075 | 74.356 | 1.00 | 42.67 |
| 2098 | C | SER | A | 387 | -16.573 | 51.578 | 75.172 | 1.00 | 43.18 |
| 2099 | O | SER | A | 387 | -16.930 | 52.538 | 74.482 | 1.00 | 43.25 |
| 2100 | N | SER | A | 388 | -15.344 | 51.059 | 75.181 | 1.00 | 44.22 |
| 2101 | CA | SER | A | 388 | -14.244 | 51.555 | 74.351 | 1.00 | 46.24 |
| 2102 | CB | SER | A | 388 | -12.908 | 51.070 | 74.888 | 1.00 | 46.39 |
| 2103 | OG | SER | A | 388 | -12.725 | 51.591 | 76.195 | 1.00 | 49.91 |
| 2104 | C | SER | A | 388 | -14.358 | 51.150 | 72.894 | 1.00 | 46.36 |
| 2105 | O | SER | A | 388 | -15.115 | 50.231 | 72.549 | 1.00 | 48.50 |
| 2106 | O1A | ADP | X | 2001 | -9.414 | 25.400 | 78.378 | 1.00 | 28.64 |
| 2107 | PA | ADP | X | 2001 | -9.486 | 25.363 | 79.862 | 1.00 | 30.26 |
| 2108 | O2A | ADP | X | 2001 | -10.590 | 26.255 | 80.350 | 1.00 | 28.31 |
| 2109 | O3A | ADP | X | 2001 | -9.587 | 23.880 | 80.555 | 1.00 | 30.98 |
| 2110 | PB | ADP | X | 2001 | -10.917 | 23.134 | 80.991 | 1.00 | 31.28 |
| 2111 | O3B | ADP | X | 2001 | -11.692 | 24.139 | 81.826 | 1.00 | 28.29 |
| 2112 | O2B | ADP | X | 2001 | -10.390 | 21.986 | 81.811 | 1.00 | 35.80 |
| 2113 | O1B | ADP | X | 2001 | -11.688 | 22.740 | 79.755 | 1.00 | 28.57 |
| 2114 | O5* | ADP | X | 2001 | -8.144 | 25.872 | 80.503 | 1.00 | 30.75 |
| 2115 | C5* | ADP | X | 2001 | -8.004 | 25.866 | 81.924 | 1.00 | 30.70 |
| 2116 | C4* | ADP | X | 2001 | -7.217 | 27.124 | 82.368 | 1.00 | 29.95 |
| 2117 | O4* | ADP | X | 2001 | -5.951 | 27.178 | 81.679 | 1.00 | 28.79 |
| 2118 | C1* | ADP | X | 2001 | -5.642 | 28.545 | 81.342 | 1.00 | 29.10 |
| 2119 | C2* | ADP | X | 2001 | -6.747 | 29.415 | 81.899 | 1.00 | 26.58 |
| 2120 | O2* | ADP | X | 2001 | -6.392 | 29.725 | 83.238 | 1.00 | 34.16 |
| 2121 | C3* | ADP | X | 2001 | -7.895 | 28.436 | 81.993 | 1.00 | 29.24 |
| 2122 | O3* | ADP | X | 2001 | -8.952 | 28.763 | 82.864 | 1.00 | 32.70 |
| 2123 | N9 | ADP | X | 2001 | -5.577 | 28.628 | 79.892 | 1.00 | 29.80 |
| 2124 | C8 | ADP | X | 2001 | -6.337 | 27.843 | 79.041 | 1.00 | 30.16 |
| 2125 | N7 | ADP | X | 2001 | -6.028 | 28.206 | 77.750 | 1.00 | 29.74 |
| 2126 | C5 | ADP | X | 2001 | -5.143 | 29.196 | 77.814 | 1.00 | 26.13 |
| 2127 | C6 | ADP | X | 2001 | -4.519 | 29.877 | 76.813 | 1.00 | 29.08 |
| 2128 | N6 | ADP | X | 2001 | -4.713 | 29.555 | 75.506 | 1.00 | 25.43 |
| 2129 | C4 | ADP | X | 2001 | -4.835 | 29.464 | 79.141 | 1.00 | 28.26 |
| 2130 | N3 | ADP | X | 2001 | -3.975 | 30.435 | 79.478 | 1.00 | 30.28 |
| 2131 | C2 | ADP | X | 2001 | -3.350 | 31.144 | 78.490 | 1.00 | 31.73 |
| 2132 | N1 | ADP | X | 2001 | -3.633 | 30.829 | 77.180 | 1.00 | 29.64 |
| 2133 | O | HOH | X | 3001 | -9.988 | 28.798 | 79.067 | 1.00 | 31.10 |

FIGURE 3AP

| A | B | C | D | E | F | G | H | I | J |
|---|---|---|---|---|---|---|---|---|---|
| 2134 | O | HOH | X3003 | | -14.393 | 22.868 | 80.872 | 1.00 | 27.85 |
| 2135 | O | HOH | X3004 | | -13.728 | 20.345 | 80.020 | 1.00 | 45.36 |
| 2136 | O | HOH | X3005 | | -26.951 | 31.694 | 86.552 | 1.00 | 30.10 |
| 2137 | O | HOH | X3006 | | -22.935 | 30.435 | 78.351 | 1.00 | 36.29 |
| 2138 | O | HOH | X3007 | | -30.168 | 16.939 | 71.846 | 1.00 | 45.13 |
| 2139 | O | HOH | X3008 | | -18.066 | 25.328 | 75.601 | 1.00 | 31.20 |
| 2140 | O | HOH | X3009 | | -11.548 | 26.843 | 82.941 | 1.00 | 36.99 |
| 2141 | O | HOH | X3010 | | -8.649 | 27.311 | 76.774 | 1.00 | 31.45 |
| 2142 | O | HOH | X3011 | | -37.854 | 36.557 | 85.013 | 1.00 | 38.02 |
| 2143 | O | HOH | X3012 | | -27.723 | 38.845 | 94.275 | 1.00 | 37.13 |
| 2144 | O | HOH | X3013 | | -16.636 | 24.694 | 78.361 | 1.00 | 32. |
| 2145 | O | HOH | X3014 | | -8.241 | 35.027 | 68.248 | 1.00 | 33.00 |
| 2146 | O | HOH | X3015 | | -0.912 | 17.916 | 82.933 | 1.00 | 36.14 |
| 2147 | O | HOH | X3017 | | -15.066 | 34.944 | 89.120 | 1.00 | 42.99 |
| 2148 | O | HOH | X3018 | | -22.824 | 25.783 | 92.176 | 1.00 | 46.76 |
| 2149 | O | HOH | X3021 | | -11.944 | 23.669 | 84.418 | 1.00 | 39.47 |
| 2150 | O | HOH | X3022 | | -12.703 | 21.499 | 77.561 | 1.00 | 40.61 |
| 2151 | O | HOH | X3023 | | -37.367 | 42.995 | 79.960 | 1.00 | 59.45 |
| 2152 | O | HOH | X3024 | | -5.576 | 15.379 | 86.195 | 1.00 | 66.48 |
| 2153 | O | HOH | X3026 | | -8.353 | 43.652 | 79.479 | 1.00 | 44.84 |
| 2154 | O | HOH | X3027 | | -23.236 | 19.714 | 67.938 | 1.00 | 47.17 |
| 2155 | O | HOH | X3028 | | -10.809 | 32.568 | 66.377 | 1.00 | 35.26 |
| 2156 | O | HOH | X3029 | | -15.673 | 31.938 | 88.442 | 1.00 | 44.34 |
| 2157 | O | HOH | X3030 | | -0.223 | 35.059 | 71.257 | 1.00 | 55.88 |
| 2158 | O | HOH | X3031 | | -20.254 | 50.297 | 89.242 | 1.00 | 49.49 |
| 2159 | O | HOH | X3032 | | -4.408 | 26.185 | 61.520 | 1.00 | 57.94 |
| 2160 | O | HOH | X3033 | | -6.464 | 20.470 | 80.244 | 1.00 | 42.32 |
| 2161 | O | HOH | X3034 | | -26.908 | 54.727 | 81.094 | 1.00 | 46.09 |
| 2162 | O | HOH | X3036 | | -3.500 | 31.862 | 81.803 | 1.00 | 43.64 |
| 2163 | O | HOH | X3037 | | -28.118 | 35.557 | 69.369 | 1.00 | 53.58 |
| 2164 | O | HOH | X3038 | | -26.182 | 36.321 | 65.264 | 1.00 | 49.67 |
| 2165 | O | HOH | X3039 | | 14.155 | 34.581 | 65.299 | 1.00 | 48.35 |
| 2166 | O | HOH | X3040 | | -34.861 | 43.555 | 76.702 | 1.00 | 53.19 |
| 2167 | O | HOH | X3041 | | -39.173 | 35.975 | 82.307 | 1.00 | 45.97 |
| 2168 | O | HOH | X3043 | | -14.153 | 39.758 | 92.741 | 1.00 | 38.14 |
| 2169 | O | HOH | X3044 | | -17.759 | 51.104 | 95.196 | 1.00 | 63.77 |
| 2170 | O | HOH | X3045 | | -17.674 | 46.814 | 68.492 | 1.00 | 55.41 |
| 2171 | O | HOH | X3046 | | -21.016 | 27.883 | 83.182 | 1.00 | 40.34 |
| 2172 | O | HOH | X3047 | | -32.376 | 28.743 | 75.835 | 1.00 | 35.07 |
| 2173 | O | HOH | X3048 | | -26.582 | 54.610 | 84.614 | 1.00 | 51.10 |
| 2174 | O | HOH | X3049 | | -28.989 | 37.779 | 69.028 | 1.00 | 45.59 |
| 2175 | O | HOH | X3050 | | 1.044 | 35.132 | 80.541 | 1.00 | 40.83 |
| 2176 | O | HOH | X3051 | | -18.143 | 48.279 | 89.631 | 1.00 | 35.13 |
| 2177 | O | HOH | X3052 | | -22.772 | 50.169 | 87.633 | 1.00 | 35.90 |
| 2178 | O | HOH | X3054 | | -28.242 | 40.105 | 67.233 | 1.00 | 39.46 |
| 2179 | O | HOH | X3055 | | -5.648 | 27.887 | 86.644 | 1.00 | 45.28 |
| 2180 | O | HOH | X3056 | | -22.278 | 29.579 | 81.107 | 1.00 | 46.99 |
| 2181 | O | HOH | X3057 | | -21.804 | 27.943 | 85.859 | 1.00 | 31.17 |
| 2182 | O | HOH | X3058 | | -19.327 | 55.542 | 84.158 | 1.00 | 69.06 |
| 2183 | O | HOH | X3059 | | -16.658 | 53.812 | 86.138 | 1.00 | 76.39 |
| 2184 | O | HOH | X3060 | | -11.616 | 48.407 | 86.048 | 1.00 | 44.96 |

FIGURE 3AQ

| A | B | C D E | F | G | H | I | J |
|---|---|---|---|---|---|---|---|
| 2185 | O | HOH X3061 | -35.280 | 41.364 | 78.456 | 1.00 | 43.63 |
| 2186 | O | HOH X3062 | -35.848 | 29.209 | 81.326 | 1.00 | 50.09 |
| 2187 | O | HOH X3063 | -20.386 | 19.911 | 74.001 | 1.00 | 46.93 |
| 2188 | O | HOH X3064 | -5.444 | 37.823 | 84.054 | 1.00 | 35.84 |
| 2189 | O | HOH X3066 | -2.738 | 38.173 | 71.721 | 1.00 | 47.11 |
| 2190 | O | HOH X3067 | -3.973 | 35.760 | 72.248 | 1.00 | 33.90 |
| 2191 | O | HOH X3068 | -29.746 | 39.136 | 96.635 | 1.00 | 62.80 |
| 2192 | O | HOH X3070 | -14.064 | 25.472 | 82.227 | 1.00 | 31.69 |
| 2193 | O | HOH X2089 | -4.484 | 33.261 | 84.056 | 1.00 | 47.20 |
| 2194 | O | HOH X2090 | -9.895 | 27.055 | 74.329 | 1.00 | 27.24 |
| 2195 | O | HOH X2091 | -0.170 | 31.678 | 70.061 | 1.00 | 29.25 |
| 2196 | O | HOH X2092 | -1.106 | 31.853 | 83.735 | 1.00 | 53.32 |
| 2197 | O | HOH X2093 | -25.264 | 41.053 | 66.798 | 1.00 | 59.10 |
| 2198 | O | HOH X2094 | -25.466 | 43.888 | 65.479 | 1.00 | 69.73 |
| 2199 | O | HOH X2095 | -32.272 | 31.292 | 69.214 | 1.00 | 67.50 |
| 2200 | O | HOH X2096 | -24.385 | 33.367 | 89.916 | 1.00 | 31.89 |
| 2201 | O | HOH X2097 | -14.677 | 21.587 | 82.263 | 1.00 | 41.33 |
| 2202 | O | HOH X2098 | -15.335 | 22.257 | 78.530 | 1.00 | 36.43 |
| 2203 | O | HOH X2099 | -11.146 | 29.804 | 67.165 | 1.00 | 47.94 |
| 2204 | O | HOH X2100 | -9.610 | 28.214 | 65.560 | 1.00 | 46.43 |
| 2205 | MG | MG  X2086 | -13.528 | 22.597 | 79.198 | 1.00 | 12.09 |
| 2206 | MG | MG  X2088 | -12.337 | 25.921 | 81.074 | 1.00 | 12.20 |
| 2207 | P | PO4 X2002 | -24.838 | 17.852 | 76.312 | 1.00 | 54.63 |
| 2208 | O1 | PO4 X2002 | -24.694 | 18.499 | 74.963 | 1.00 | 59.50 |
| 2209 | O2 | PO4 X2002 | -26.204 | 17.207 | 76.361 | 1.00 | 64.72 |
| 2210 | O3 | PO4 X2002 | -23.779 | 16.793 | 76.532 | 1.00 | 57.00 |
| 2211 | O4 | PO4 X2002 | -24.798 | 18.859 | 77.420 | 1.00 | 60.01 |

SEQUENCE LISTING

<160> NUMBER OF SEQ ID NOS: 3

<210> SEQ ID NO 1
<211> LENGTH: 403
<212> TYPE: PRT
<213> ORGANISM: Homo sapiens
<220> FEATURE:
<221> NAME/KEY: Amino acid sequence for full-length human wild type AIK
<222> LOCATION: (1)..(403)
<223> OTHER INFORMATION:
<220> FEATURE:
<221> NAME/KEY: Amino acid sequence for full-length human wild type AIK
<222> LOCATION: (1)..(403)
<223> OTHER INFORMATION: Seq. ID. No. 1 encodes for residues 124-391
<300> PUBLICATION INFORMATION:
<308> DATABASE ACCESSION NUMBER: Genbank Accession No. NP_003591
<309> DATABASE ENTRY DATE: 1998-05-08
<313> RELEVANT RESIDUES: (1)..(403)

<400> SEQUENCE: 1

```
Met Asp Arg Ser Lys Glu Asn Cys Ile Ser Gly Pro Val Lys Ala Thr
 1               5                  10                  15

Ala Pro Val Gly Gly Pro Lys Arg Val Leu Val Thr Gln Gln Ile Pro
            20                  25                  30

Cys Gln Asn Pro Leu Pro Val Asn Ser Gly Gln Ala Gln Arg Val Leu
        35                  40                  45

Cys Pro Ser Asn Ser Ser Gln Arg Val Pro Leu Gln Ala Gln Lys Leu
    50                  55                  60

Val Ser Ser His Lys Pro Val Gln Asn Gln Lys Gln Lys Gln Leu Gln
65                  70                  75                  80

Ala Thr Ser Val Pro His Pro Val Ser Arg Pro Leu Asn Asn Thr Gln
                85                  90                  95

Lys Ser Lys Gln Pro Leu Pro Ser Ala Pro Glu Asn Asn Pro Glu Glu
            100                 105                 110

Glu Leu Ala Ser Lys Gln Lys Asn Glu Glu Ser Lys Lys Arg Gln Trp
        115                 120                 125

Ala Leu Glu Asp Phe Glu Ile Gly Arg Pro Leu Gly Lys Gly Lys Phe
    130                 135                 140

Gly Asn Val Tyr Leu Ala Arg Glu Lys Gln Ser Lys Phe Ile Leu Ala
145                 150                 155                 160

Leu Lys Val Leu Phe Lys Ala Gln Leu Glu Lys Ala Gly Val Glu His
                165                 170                 175

Gln Leu Arg Arg Glu Val Glu Ile Gln Ser His Leu Arg His Pro Asn
            180                 185                 190

Ile Leu Arg Leu Tyr Gly Tyr Phe His Asp Ala Thr Arg Val Tyr Leu
        195                 200                 205

Ile Leu Glu Tyr Ala Pro Leu Gly Thr Val Tyr Arg Glu Leu Gln Lys
    210                 215                 220

Leu Ser Lys Phe Asp Glu Gln Arg Thr Ala Thr Tyr Ile Thr Glu Leu
225                 230                 235                 240

Ala Asn Ala Leu Ser Tyr Cys His Ser Lys Arg Val Ile His Arg Asp
                245                 250                 255

Ile Lys Pro Glu Asn Leu Leu Leu Gly Ser Ala Gly Glu Leu Lys Ile
            260                 265                 270

Ala Asp Phe Gly Trp Ser Val His Ala Pro Ser Ser Arg Arg Thr Thr
        275                 280                 285

Leu Cys Gly Thr Leu Asp Tyr Leu Pro Pro Glu Met Ile Glu Gly Arg
```

|  |  |  |  |  |  |  |  |  |  |  |
|---|---|---|---|---|---|---|---|---|---|---|
|  |  |  |  | 290 |  |  | 295 |  | 300 |  |
| Met | His | Asp | Glu | Lys | Val | Asp | Leu | Trp | Ser | Leu | Gly | Val | Leu | Cys | Tyr |
| 305 |  |  |  | 310 |  |  |  | 315 |  |  |  |  |  |  | 320 |

Met His Asp Glu Lys Val Asp Leu Trp Ser Leu Gly Val Leu Cys Tyr
305                 310                 315                 320

Glu Phe Leu Val Gly Lys Pro Pro Phe Glu Ala Asn Thr Tyr Gln Glu
                325                 330                 335

Thr Tyr Lys Arg Ile Ser Arg Val Glu Phe Thr Phe Pro Asp Phe Val
            340                 345                 350

Thr Glu Gly Ala Arg Asp Leu Ile Ser Arg Leu Leu Lys His Asn Pro
                355                 360                 365

Ser Gln Arg Pro Met Leu Arg Glu Val Leu Glu His Pro Trp Ile Thr
        370                 375                 380

Ala Asn Ser Ser Lys Pro Ser Asn Cys Gln Asn Lys Glu Ser Ala Ser
385                 390                 395                 400

Lys Gln Ser

<210> SEQ ID NO 2
<211> LENGTH: 804
<212> TYPE: DNA
<213> ORGANISM: Homo sapiens
<220> FEATURE:
<221> NAME/KEY: Human cDNA sequence encoding residues 125-391 of AIK
<222> LOCATION: (1)..(804)
<223> OTHER INFORMATION:

<400> SEQUENCE: 2

```
aagaggcagt gggctttgga agactttgaa attggtcgcc ctctgggtaa aggaaagttt      60
ggtaatgttt atttggcaag agaaaagcaa agcaagttta ttctggctct taaagtgtta     120
tttaaagctc agctggagaa agccggagtg gagcatcagc tcagaagaga agtagaaata     180
cagtcccacc ttcggcatcc taatattctt agactgtatg gttatttcca tgatgctacc     240
agagtctacc taattctgga atatgcacca cttggaacag tttatagaga acttcagaaa     300
cttttcaaagt tgatgagca gagaactgct acttatataa cagaattggc aaatgccctg     360
tcttactgtc attcgaagag agttattcat agagacatta gccagagaa cttacttctt     420
ggatcagctg gagagcttaa aattgcagat tttgggtggt cagtacatgc tccatcttcc     480
aggaggacca ctctctgtgg caccctggac tacctgcccc ctgaaatgat tgaaggtcgg     540
atgcatgatg agaaggtgga tctctggagc cttggagttc tttgctatga attttagtt     600
gggaagcctc cttttgaggc aaacacatac caagagacct acaaaagaat atcacgggtt     660
gaattcacat tccctgactt tgtaacagag ggagccaggg acctcatttc aagactgttg     720
aagcataatc ccagccagag gccaatgctc agagaagtac ttgaacaccc ctggatcaca     780
gcaaattcat caaaaccatc atag                                            804
```

<210> SEQ ID NO 3
<211> LENGTH: 295
<212> TYPE: PRT
<213> ORGANISM: Homo sapiens
<220> FEATURE:
<221> NAME/KEY: Amino acid sequence for residues 125-391 of AIK with a
        cleavable (rTev) N-terminal 6x-histidine tag
<222> LOCATION: (1)..(295)
<223> OTHER INFORMATION:
<220> FEATURE:
<221> NAME/KEY: Cleavable (rTev) N-terminal 6x-histidine tag
<222> LOCATION: (1)..(28)
<223> OTHER INFORMATION:

<400> SEQUENCE: 3

-continued

```
Met Ser Tyr Tyr His His His His His Asp Tyr Asp Ile Pro Thr
1            5                   10                15

Thr Glu Asn Leu Tyr Phe Gln Gly Ala Met Gly Ser Lys Arg Gln Trp
            20                  25                  30

Ala Leu Glu Asp Phe Glu Ile Gly Arg Pro Leu Gly Lys Gly Lys Phe
            35                  40                  45

Gly Asn Val Tyr Leu Ala Arg Glu Lys Gln Ser Lys Phe Ile Leu Ala
        50                  55                  60

Leu Lys Val Leu Phe Lys Ala Gln Leu Glu Lys Ala Gly Val Glu His
65                  70                  75                  80

Gln Leu Arg Arg Glu Val Glu Ile Gln Ser His Leu Arg His Pro Asn
                85                  90                  95

Ile Leu Arg Leu Tyr Gly Tyr Phe His Asp Ala Thr Arg Val Tyr Leu
                100                 105                 110

Ile Leu Glu Tyr Ala Pro Leu Gly Thr Val Tyr Arg Glu Leu Gln Lys
            115                 120                 125

Leu Ser Lys Phe Asp Glu Gln Arg Thr Ala Thr Tyr Ile Thr Glu Leu
    130                 135                 140

Ala Asn Ala Leu Ser Tyr Cys His Ser Lys Arg Val Ile His Arg Asp
145                 150                 155                 160

Ile Lys Pro Glu Asn Leu Leu Leu Gly Ser Ala Gly Glu Leu Lys Ile
                165                 170                 175

Ala Asp Phe Gly Trp Ser Val His Ala Pro Ser Ser Arg Arg Thr Thr
            180                 185                 190

Leu Cys Gly Thr Leu Asp Tyr Leu Pro Pro Glu Met Ile Glu Gly Arg
        195                 200                 205

Met His Asp Glu Lys Val Asp Leu Trp Ser Leu Gly Val Leu Cys Tyr
    210                 215                 220

Glu Phe Leu Val Gly Lys Pro Pro Phe Glu Ala Asn Thr Tyr Gln Glu
225                 230                 235                 240

Thr Tyr Lys Arg Ile Ser Arg Val Glu Phe Thr Phe Pro Asp Phe Val
            245                 250                 255

Thr Glu Gly Ala Arg Asp Leu Ile Ser Arg Leu Leu Lys His Asn Pro
                260                 265                 270

Ser Gln Arg Pro Met Leu Arg Glu Val Leu Glu His Pro Trp Ile Thr
        275                 280                 285

Ala Asn Ser Ser Lys Pro Ser
        290             295
```

CRYSTALLIZATION OF AURORA/LPL1P-RELATED KINASE

RELATED APPLICATION

This application claims the benefit of U.S. Provisional Application No. 60/390,355, filed Jun. 21, 2002, which is incorporated herein by reference.

FIELD OF THE INVENTION

The present invention relates to Aurora/LPL1P-related kinase ("AIK") and more specifically to AIK in crystalline form, methods of forming crystals comprising AIK, methods of using crystals comprising AIK, a crystal structure of AIK, and methods of using the crystal structure.

BACKGROUND OF THE INVENTION

The most dangerous forms of cancer comprise malignant cells that metastasize to distant sites in a body. Metastatic cells have the property of being able to break away from a primary tumor, translocate to distant sites, and colonize distant and foreign microenvironments. Cancer cell metastasis requires cellular capacity to 1) detach from a primary tumor, 2) migrate and invade through local tissues, 3) translocate to distant sites in the body (via lymph or blood), 4) colonize a foreign site, and 5) grow and survive in this foreign environment. All of these behaviors are linked to cell adhesions.

Cell adhesions control the physical interactions of cells with their microenvironment. Cell adhesions also initiate signals that dictate tumor cell growth, death, and differentiation. At the cellular level, metastatic cells have overcome restraints upon cell growth and migration that result from physical linkages and signals conveyed by cell-cell contacts. Malignant cells often have increased interactions with surrounding extracellular matrix (ECM) proteins that provide linkages and signals that promote several aspects of metastasis.

A general approach to designing inhibitors that are selective for a given protein is to determine how a putative inhibitor interacts with a three dimensional structure of that protein. For this reason it is useful to obtain the protein in crystalline form and perform X-ray diffraction techniques to determine the protein's three dimensional structure coordinates. Various methods for preparing crystalline proteins are known in the art.

Once protein crystals are produced, crystallographic data can be generated using the crystals to provide useful structural information that assists the design of small molecules that bind to the active site of the protein and inhibit the protein's activity in vivo. If the protein is crystallized as a complex with a ligand, one can determine both the shape of the protein's binding pocket when bound to the ligand, as well as the amino acid residues that are capable of close contact with the ligand. By knowing the shape and amino acid residues in the binding pocket, one may design new ligands that will interact favorably with the protein. With such structural information, available computational methods may be used to predict how strong the ligand binding interaction will be. Such methods help in the design of inhibitors that bind strongly, as well as selectively to the protein.

SUMMARY OF THE INVENTION

The present invention is directed to crystals comprising AIK and particularly crystals comprising AIK that have sufficient size and quality to obtain useful information about the structural properties of AIK and molecules or complexes that may associate with AIK.

In one embodiment, a composition is provided that comprises a protein in crystalline form wherein at least a portion of the protein has 55%, 65%, 75%, 85%, 90%, 95%, 97%, 99% or greater identity with residues 125-391 or 126-388 of SEQ. ID No. 1.

In one variation, the protein has activity characteristic of AIK. For example, the protein may optionally be inhibited by inhibitors of wild type AIK. The protein crystal may also diffract X-rays for a determination of structure coordinates to a resolution of 4 Å, 3.5 Å, 3.0 Å or less.

In one variation, the protein crystal has a crystal lattice in a $P6_122$ space group. The protein crystal may also have a crystal lattice having unit cell dimensions, +/−5%, of a=80.45 Å, b=80.45 Å and c=172.18 Å. The protein crystal may also have a crystal lattice having unit cell dimensions, +/−2%, of a=80.45 Å, b=80.45 Å and c=172.18 Å.

The present invention is also directed to crystallizing AIK. The present invention is also directed to the conditions useful for crystallizing AIK. It should be recognized that a wide variety of crystallization methods can be used in combination with the crystallization conditions to form crystals comprising AIK including, but not limited to, vapor diffusion, batch, dialysis, and other methods of contacting the protein solution for the purpose of crystallization.

The present invention is also directed to crystallizing AIK. The present invention is also directed to the conditions useful for crystallizing AIK. It should be recognized that a wide variety of crystallization methods can be used in combination with the crystallization conditions to form crystals comprising AIK including, but not limited to, vapor diffusion, batch, dialysis, and other methods of contacting the protein solution for the purpose of crystallization.

In one embodiment, a method is provided for forming crystals of a protein comprising: forming a crystallization volume comprising: a protein wherein at least a portion of the protein has 55%, 65%, 75%, 85%, 90%, 95%, 97%, 99% or greater identity with residues 125-391 or 126-388 of SEQ. ID No. 1; and storing the crystallization volume under conditions suitable for crystal formation.

In one variation, the crystallization volume comprises the protein in a concentration between 1 mg/ml and 50 mg/ml, and 1-50% w/v of precipitant wherein the precipitant comprises one or more members of the group consisting of MPD, PEG 100-6000, PEG MME 550-5000, ammonium salt, glycerol and ethylene glycol, and wherein the crystallization volume has a pH between pH 6.5 and pH 10.

The method may optionally further comprise forming a protein crystal that has a crystal lattice in a $P6_122$ space group. The method also optionally further comprises forming a protein crystal that has a crystal lattice having unit cell dimensions, +/−5%, of a=80.45 Å, b=80.45 Å and c=172.18 Å. The invention also relates to protein crystals formed by these methods.

The present invention is also directed to a composition comprising an isolated protein that comprises or consists of one or more of the protein sequence(s) of AIK taught herein for crystallizing AIK. The present invention is also directed to a composition comprising an isolated nucleic acid molecule that comprises or consists of the nucleotides for expressing the protein sequence of AIK taught herein for crystallizing AIK.

The present invention is also directed to an expression vector that may be used to express the isolated proteins taught herein for crystallizing AIK.

The present invention is also directed to an expression vector that may be used to express the isolated proteins taught herein for crystallizing AIK. In one variation, the expression vector comprises a promoter that promotes expression of the isolated protein.

The present invention is also directed to a cell line transformed or transfected by an isolated nucleic acid molecule or expression vector of the present invention.

The present invention is also directed to structure coordinates for AIK as well as structure coordinates that are comparatively similar to these structure coordinates. It is noted that these comparatively similar structure coordinates may encompass proteins with similar sequences and/or structures, such as other kinase. For example, machine-readable data storage media is provided having data storage material encoded with machine-readable data that comprises structure coordinates that are comparatively similar to the structure coordinates of AIK. The present invention is also directed to a machine readable data storage medium having data storage material encoded with machine readable data, which, when read by an appropriate machine, can display a three dimensional representation of all or a portion of a structure of AIK or a model that is comparatively similar to the structure of all or a portion of AIK.

Various embodiments of machine readable data storage medium are provided that comprise data storage material encoded with machine readable data. The machine readable data comprises: structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1. The amino acids being overlayed and compared need not to be identical when the RMSD calculation is performed on alpha carbons and main chain atoms but the amino acids being overlayed and compared must have identical side chains when the RMSD calculation is performed on all non-hydrogen atoms.

For example, in one embodiment where the comparison is based on the 4 Angstrom set of amino acid residues (Column 1) and is based on superimposing alpha-carbon atoms (Column 2), the structure coordinates may have a root mean square deviation equal to or less than 0.44 when compared to the structure coordinates of FIG. 3.

TABLE 1

| AA RESIDUES TO USE TO PERFORM RMSD COMPARISON | PORTION OF EACH AA RESIDUE USED TO PERFORM RMSD COMPARISON | RMSD VALUE LESS THAN OR EQUAL TO | | |
|---|---|---|---|---|
| Table 2 | alpha-carbon atoms[1] | 0.44 | 0.30 | 0.22 |
| (4 Angstrom set) | main-chain atoms[1] | 0.43 | 0.28 | 0.21 |
|  | all non-hydrogen[2] | 0.61 | 0.41 | 0.31 |
| Table 3 | alpha-carbon atoms[1] | 0.48 | 0.31 | 0.24 |
| (7 Angstrom set) | main-chain atoms[1] | 0.47 | 0.31 | 0.23 |
|  | all non-hydrogen[2] | 0.65 | 0.44 | 0.33 |
| Table 4 | alpha-carbon atoms[1] | 0.82 | 0.55 | 0.41 |
| (10 Angstrom set) | main-chain atoms[1] | 0.79 | 0.53 | 0.40 |
|  | all non-hydrogen[2] | 0.93 | 0.62 | 0.47 |
| 125-391 or 126-388 of SEQ. ID No. 1 | alpha-carbon atoms[1] | 1.16 | 0.78 | 0.58 |
|  | main-chain atoms[1] | 1.15 | 0.78 | 0.58 |
|  | all non-hydrogen[2] | 1.20 | 0.79 | 0.60 |

TABLE 1-continued

| AA RESIDUES TO USE TO PERFORM RMSD COMPARISON | PORTION OF EACH AA RESIDUE USED TO PERFORM RMSD COMPARISON | RMSD VALUE LESS THAN OR EQUAL TO |
|---|---|---|

[1] the RMSD computed between the atoms of all amino acids that are common to both the target and the reference in the aligned and superposed structure. The amino acids need not to be identical.
[2] the RMSD computed only between identical amino acids, which are common to both the target and the reference in the aligned and superposed structure.

The present invention is also directed to a three-dimensional structure of all or a portion of AIK. This three-dimensional structure may be used to identify binding sites, to provide mutants having desirable binding properties, and ultimately, to design, characterize, or identify ligands capable of interacting with AIK. Ligands that interact with AIK may be any type of atom, compound, protein or chemical group that binds to or otherwise associates with the protein. Examples of types of ligands include natural substrates for AIK, inhibitors of AIK, and heavy atoms. The inhibitors of AIK may optionally be used as drugs to treat therapeutic indications by modifying the in vivo activity of AIK.

In various embodiments, methods are provided for displaying a three dimensional representation of a structure of a protein comprising:

taking machine readable data comprising structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1;

computing a three dimensional representation of a structure based on the structure coordinates; and displaying the three dimensional representation.

The present invention is also directed to a method for solving a three-dimensional crystal structure of a target protein using the structure of AIK.

In various embodiments, computational methods are provided comprising: taking machine readable data comprising structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1;

computing phases based on the structural coordinates;

computing an electron density map based on the computed phases; and determining a three-dimensional crystal structure based on the computed electron density map.

In various embodiments, computational methods are provided comprising: taking an X-ray diffraction pattern of a crystal of the target protein; and computing a three-dimensional electron density map from the X-ray diffraction pattern by molecular replacement, wherein structure coordinates used as a molecular replacement model comprise structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1.

These methods may optionally further comprise determining a three-dimensional crystal structure based upon the computed three-dimensional electron density map.

The present invention is also directed to using a crystal structure of AIK, in particular the structure coordinates of AIK and the surface contour defined by them, in methods for screening, designing, or optimizing molecules or other chemical entities that interact with and preferably inhibit AIK.

One skilled in the art will appreciate the numerous uses of the inventions described herein, particularly in the areas of drug design, screening and optimization of drug candidates, as well as in determining additional unknown crystal structures. For example, a further aspect of the present invention relates to using a three-dimensional crystal structure of all or a portion of AIK and/or its structure coordinates to evaluate the ability of entities to associate with AIK. The entities may be any entity that may function as a ligand and thus may be any type of atom, compound, protein (such as antibodies) or chemical group that can bind to or otherwise associate with a protein.

In various embodiments, methods are provided for evaluating a potential of an entity to associate with a protein comprising:

creating a computer model of a protein structure using structure coordinates that comprise structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1;

performing a fitting operation between the entity and the computer model; and analyzing results of the fitting operation to quantify an association between the entity and the model.

In other embodiments, methods are provided for identifying entities that can associate with a protein comprising:
generating a three-dimensional structure of a protein using structure coordinates that comprise structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1; and employing the three-dimensional structure to design or select an entity that can associate with the protein; and contacting the entity with a protein wherein at least a portion of the protein has 55%, 65%, 75%, 85%, 90%, 95%, 97%, 99% or greater identity with residues 125-391 or 126-388 of SEQ. ID No. 1.

In other embodiments, methods are provided for identifying entities that can associate with a protein comprising:
generating a three-dimensional structure of a protein using structure coordinates that comprise structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1; and employing the three-dimensional structure to design or select an entity that can associate with the protein.

In other embodiments, methods are provided for identifying entities that can associate with a protein comprising:
computing a computer model for a protein binding pocket, at least a portion of the computer model having a surface contour that has a root mean square deviation equal to or less than a given RMSD value specified in Columns 3, 4 or 5 of Table 1 when the coordinates used to compute the surface contour are compared to the structure coordinates of FIG. 3, wherein (a) the root mean square deviation is calculated by the calculation method set forth herein, (b) the portion of amino acid residues associated with the given RMSD value in Table 1 (specified in Column 2 of Table 1) are superimposed according to the RMSD calculation, and (c) the root mean square deviation is calculated based only on those amino acid residues present in both the protein being modeled and the portion of the protein associated with the given RMSD in Table 1 (specified in Column 1 of Table 1);

employing the computer model to design or select an entity that can associate with the protein; and contacting the entity with a protein wherein at least a portion of the protein has 55%, 65%, 75%, 85%, 90%, 95%, 97%, 99% or greater identity with residues 125-391 or 126-388 of SEQ. ID No. 1.

In other embodiments, methods are provided for identifying entities that can associate with a protein comprising:
computing a computer model for a protein binding pocket, at least a portion of the computer model having a surface contour that has a root mean square deviation equal to or less than a given RMSD value specified in Columns 3, 4 or 5 of Table 1 when the coordinates used to compute the surface contour are compared to the structure coordinates of FIG. 3, wherein (a) the root mean square deviation is calculated by the calculation method set forth herein, (b) the portion of amino acid residues associated with the given RMSD value in Table 1 (specified in Column 2 of Table 1) are superimposed according to the RMSD calculation, and (c) the root mean square deviation is calculated based only on those amino acid residues present in both the protein being modeled and the portion of the protein associated with the given RMSD in Table 1 (specified in Column 1 of Table 1); and employing the computer model to design or select an entity that can associate with the protein.

In other embodiments, methods are provided for evaluating the ability of an entity to associate with a protein, the method comprising:
constructing a computer model defined by structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1; and selecting an entity to be evaluated by a method selected from the group consisting of (i) assembling molecular fragments into the entity, (ii) selecting an entity from a small molecule database, (iii) de novo ligand design of the entity, and (iv) modifying a known ligand for AIK, or a portion thereof; performing a fitting program operation between computer models of the entity to be evaluated and the binding pocket in order to provide an energy-minimized configuration of the entity in the binding pocket; and evaluating the results of the fitting operation to quantify the association between the entity and the binding pocket model in order to evaluate the ability of the entity to associate with the binding pocket.

In other embodiments, methods are provided for evaluating the ability of an entity to associate with a protein, the method comprising:

computing a computer model for a protein binding pocket, at least a portion of the computer model having a surface contour that has a root mean square deviation equal to or less than a given RMSD value specified in Columns 3, 4 or 5 of Table 1 when the coordinates used to compute the surface contour are compared to the structure coordinates of FIG. 3, wherein (a) the root mean square deviation is calculated by the calculation method set forth herein, (b) the portion of amino acid residues associated with the given RMSD value in Table 1 (specified in Column 2 of Table 1) are superimposed according to the RMSD calculation, and (c) the root mean square deviation is calculated based only on those amino acid residues present in both the protein being modeled and the portion of the protein associated with the given RMSD in Table 1 (specified in Column 1 of Table 1); and selecting an entity to be evaluated by a method selected from the group consisting of (i) assembling molecular fragments into the entity, (ii) selecting an entity from a small molecule database, (iii) de novo ligand design of the entity, and (iv) modifying a known ligand for AIK, or a portion thereof; performing a fitting program operation between computer models of the entity to be evaluated and the binding pocket in order to provide an energy-minimized configuration of the entity in the binding pocket; and evaluating the results of the fitting operation to quantify the association between the entity and the binding pocket model in order to evaluate the ability of the entity to associate with the binding pocket.

In regard to each of these embodiments, the protein may optionally have activity characteristic of AIK. For example, the protein may optionally be inhibited by inhibitors of wild type AIK.

In another embodiment, a method is provided for identifying an entity that associates with a protein comprising: taking structure coordinates from diffraction data obtained from a crystal of a protein wherein at least a portion of the protein has 55%, 65%, 75%, 85%, 90%, 95%, 97%, 99% or greater identity with residues 125-391 or 126-388 of SEQ. ID No. 1; and performing rational drug design using a three dimensional structure that is based on the obtained structure coordinates.

The protein crystals may optionally have a crystal lattice with a $P6_122$ space group and unit cell dimensions, +/−5%, of a=80.45 Å, b=80.45 Å and c=172.18 Å.

The method may optionally further comprise selecting one or more entities based on the rational drug design and contacting the selected entities with the protein. The method may also optionally further comprise measuring an activity of the protein when contacted with the one or more entities. The method also may optionally further comprise comparing activity of the protein in a presence of and in the absence of the one or more entities; and selecting entities where activity of the protein changes depending whether a particular entity is present. The method also may optionally further comprise contacting cells expressing the protein with the one or more entities and detecting a change in a phenotype of the cells when a particular entity is present.

BRIEF DESCRIPTION OF THE FIGURES

FIG. 1 illustrates SEQ. ID Nos. 1, 2, and 3 referred to in this application.

FIG. 3 lists a set of atomic structure coordinates for AIK as derived by X-ray crystallography from a crystal that comprises a portion of the protein, i.e., residues 24-295 of SEQ ID NO:3, which comprises residues 125-391 of SEQ ID NO: 1. The following abbreviations are used in FIG. 3: "X, Y, Z" crystallographically define the atomic position of the element measured; "B" is a thermal factor that measures movement of the atom around its atomic center; "Occ" is an occupancy factor that refers to the fraction of the molecules in which each atom occupies the position specified by the coordinates (a value of "1" indicates that each atom has the same conformation, i.e., the same position, in all molecules of the crystal).

DETAILED DESCRIPTION OF THE INVENTION

Figure 2:
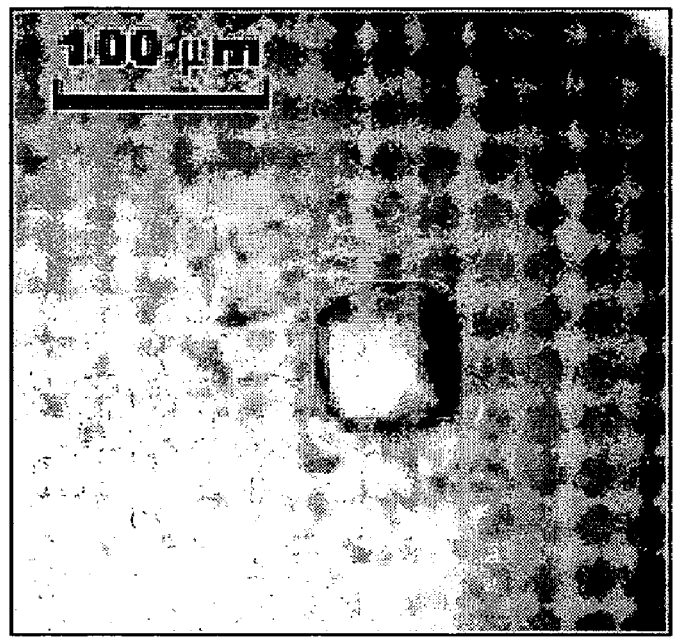
FIG. 2 illustrates a crystal of an AIK-ATPγS complex.

The present invention relates to one of the family of tyrosine kinases known as AIK. More specifically, present invention relates to AIK in crystalline form, methods of forming crystals comprising AIK, methods of using crystals comprising AIK, a crystal structure of AIK, and methods of using the crystal structure.

In describing protein structure and function herein, reference is made to amino acids comprising the protein. The amino acids may also be referred to by their conventional abbreviations; A=Ala=Alanine; T=Thr=Threonine; V=Val=Valine; C=Cys=Cysteine; L=Leu=Leucine; Y=Tyr=Tyrosine; I=Ile=Isoleucine; N=Asn=Asparagine; P=Pro=Proline; Q=Gln=Glutamine; F=Phe=Phenylalanine; D=Asp=Aspartic Acid; W=Trp=Tryptophan; E=Glu=Glutamic Acid; M=Met=Methionine; K=Lys=Lysine; G=Gly=Glycine; R=Arg=Arginine; S=Ser=Serine; and H=His=Histidine.

1. AIK

AIK is a cell-cycle-regulated serine-threonine kinase that regulates centrosome maturation, chromosome segregation and cytokinesis, ensuring genetic integrity of progenic cells.

AIK amplification and overexpression has been detected in breast tumors, ovarian tumors and may play a role in oncogenic transformation.

It should be understood that the methods and compositions provided herein relating to AIK are not intended to be limited to wild type AIK but instead are also directed to fragments and variants of AIK as described herein.

In one embodiment, AIK comprises the wild-type form of full length AIK, set forth herein as SEQ. ID No. 1. (GenBank Accession Number NP_003591; Sen, S., Zhou, H. and White, R. A., "A putative serine/threonine kinase encoding gene BTAK on chromosome 20q13 is amplified and overexpressed in human breast cancer cell lines", *Oncogene* 14 (18), 2195-2200, 1997).

In another embodiment, AIK comprises residues 125-391 of SEQ. ID No. 1 which comprises the kinase domain of wild-type AIK.

In another embodiment, AIK comprises residues 126-388 of SEQ. ID No. 1 which comprises the portion of the kinase domain of wild-type AIK that are represented in the set of structure coordinates shown in FIG. 3.

It should be recognized that the invention may be readily extended to various variants of wild-type AIK and variants of fragments thereof. In another embodiment, AIK comprises a sequence that has at least 65% identity, preferably at least 70%, 80%, 90%, 95% or higher identity with any one of the above sequences (e.g., all of SEQ. ID No. 1 or residues 125-391 or 126-388 of SEQ. ID No. 1).

It is also noted that the above sequences of AIK is also intended to encompass isoforms, mutants and fusion proteins of these sequences. Preferred fusion proteins are exemplified by SEQ. ID No. 3 which includes a poly-histidine ($His_6$) region.

With the crystal structure provided herein, where amino acid residues are positioned in the structure are now known. As a result, the impact of different substitutions can be more easily predicted and understood.

For example, based on the crystal structure, applicants have determined that AIK amino acids in Table 2 are within 4 Angstroms of and therefore close enough to interact with ATPγS. Applicants have also determined that the amino acids of Table 3 are within 7 Angstroms of bound ATPγS and therefore are also close enough to interact with that substrate or analogs thereof. Further it has been determined that the amino acids of Table 4 are within 10 Angstroms of the bound ATPγS. One or either of these sets of amino acids is preferably conserved in a variant of AIK. Hence, AIK may optionally comprise a sequence that has at least 65% identity, preferably at least 70%, 80%, 90%, 95% or higher identity with any one of the above sequences (e.g., all of SEQ. ID No. 1 or residues 125-391 or 126-388 of SEQ. ID No. 1) where at least the residues shown in Tables 2, 3, and/or 4 are conserved with the exception of 0, 1, 2, 3, or 4 residues. It should be recognized that one might optionally also vary some of the binding site residues in order to determine the effect such changes have on structure or activity.

TABLE 2

ATP binding site residues within 4 Angstroms of ATPγS.

| LEU | 139 | ALA | 160 | THR | 217 |
|---|---|---|---|---|---|
| GLY | 140 | LYS | 162 | GLU | 260 |
| LYS | 141 | LEU | 194 | ASN | 261 |
| GLY | 142 | LEU | 210 | LEU | 263 |
| LYS | 143 | GLU | 211 | ASP | 274 |
| VAL | 147 | ALA | 213 | | |

TABLE 3

ATP binding site residues within 7 Angstroms of ATPγS.

| LEU | 139 | VAL | 163 | TYR | 219 |
|---|---|---|---|---|---|
| GLY | 140 | LEU | 164 | ARG | 220 |
| LYS | 141 | GLU | 181 | ASP | 256 |
| GLY | 142 | GLN | 185 | LYS | 258 |
| LYS | 143 | LEU | 194 | PRO | 259 |
| PHE | 144 | ARG | 195 | GLU | 260 |
| GLY | 145 | LEU | 210 | ASN | 261 |
| ASN | 146 | GLU | 211 | LEU | 262 |
| VAL | 147 | TYR | 212 | LEU | 263 |
| TYR | 148 | ALA | 213 | LEU | 264 |
| LEU | 159 | PRO | 214 | ALA | 273 |
| ALA | 160 | LEU | 215 | ASP | 274 |
| LEU | 161 | GLY | 216 | PHE | 275 |
| LYS | 162 | THR | 217 | GLY | 276 |

TABLE 4

ATP binding site residues within 10 Angstroms of ATPγS.

| ARG | 137 | LEU | 169 | ARG | 220 |
|---|---|---|---|---|---|
| PRO | 138 | VAL | 174 | GLU | 221 |
| LEU | 139 | GLN | 177 | GLN | 223 |
| GLY | 140 | LEU | 178 | HIS | 254 |
| LYS | 141 | GLU | 181 | ASP | 256 |
| GLY | 142 | GLN | 185 | LYS | 258 |
| LYS | 143 | ILE | 193 | PRO | 259 |
| PHE | 144 | LEU | 194 | GLU | 260 |
| GLY | 145 | ARG | 195 | ASN | 261 |
| ASN | 146 | LEU | 196 | LEU | 262 |
| VAL | 147 | TYR | 197 | LEU | 263 |
| TYR | 148 | LEU | 208 | LEU | 264 |
| LEU | 149 | ILE | 209 | GLY | 265 |
| ALA | 150 | LEU | 210 | SER | 266 |
| ILE | 158 | GLU | 211 | LYS | 271 |
| LEU | 159 | TYR | 212 | ILE | 272 |
| ALA | 160 | ALA | 213 | ALA | 273 |
| LEU | 161 | PRO | 214 | ASP | 274 |
| LYS | 162 | LEU | 215 | PHE | 275 |
| VAL | 163 | GLY | 216 | GLY | 276 |
| LEU | 164 | THR | 217 | TRP | 277 |
| PHE | 165 | VAL | 218 | SER | 278 |

With the benefit of the crystal structure and guidance provided by Tables 2, 3, and 4, a wide variety of AIK variants (e.g., insertions, deletions, substitutions, etc.) that fall within the above specified identity ranges may be designed and manufactured utilizing recombinant DNA techniques well known to those skilled in the art, particularly in view of the knowledge of the crystal structure provided herein. These modifications can be used in a number of combinations to produce the variants. The present invention is useful for crystallizing and then solving the structure of the range of variants of AIK.

Variants of AIK may be insertional variants in which one or more amino acid residues are introduced into a predetermined site in the AIK sequence. For instance, insertional variants can be fusions of heterologous proteins or polypeptides to the amino or carboxyl terminus of the subunits.

Variants of AIK also may be substitutional variants in which at least one residue has been removed and a different residue inserted in its place. Non-natural amino acids (i.e. amino acids not normally found in native proteins), as well as isosteric analogs (amino acid or otherwise) may optionally be employed in substitutional variants. Examples of suitable substitutions are well known in the art, such as the Glu→Asp, Ser→Cys, Cys→Ser, and His→Ala for example.

Another class of variants is deletional variants, which are characterized by the removal of one or more amino acid residues from the AIK sequence.

Other variants may be produced by chemically modifying amino acids of the native protein (e.g., diethylpyrocarbonate treatment that modifies histidine residues). Preferred are chemical modifications that are specific for certain amino acid side chains. Specificity may also be achieved by blocking other side chains with antibodies directed to the side chains to be protected. Chemical modification includes such reactions as oxidation, reduction, amidation, deamidation, or substitution of bulky groups such as polysaccharides or polyethylene glycol.

Exemplary modifications include the modification of lysinyl and amino terminal residues by reaction with succinic or other carboxylic acid anhydrides. Modification with these agents has the effect of reversing the charge of the lysinyl residues. Other suitable reagents for modifying amino-containing residues include imidoesters such as methyl picolinimidate; pyridoxal phosphate; pyridoxal chloroborohydride; trinitrobenzenesulfonic acid; 0-methylisourea, 2,4-pentanedione; and transaminaseN: talyzed reaction with glyoxylate, and N-hydroxysuccinamide esters of polyethylene glycol or other bulky substitutions.

Arginyl residues may be modified by reaction with a number of reagents, including phenylglyoxal, 2,3-butanedione, 1,2-cyclohexanedione, and ninhydrin. Modification of arginine residues requires that the reaction be performed in alkaline conditions because of the high $pK_a$, of the guanidine functional group. Furthermore, these reagents may react with the groups of lysine as well as the arginine epsilon-amino group.

Tyrosyl residues may also be modified to introduce spectral labels into tyrosyl residues by reaction with aromatic diazonium compounds or tetranitromethane, forming O-acetyl tyrosyl species and 3-nitro derivatives, respectively. Tyrosyl residues may also be iodinated using $^{125}I$ or $^{131}I$ to prepare labeled proteins for use in radioimmunoassays.

Carboxyl side groups (aspartyl or glutamyl) may be selectively modified by reaction with carbodiimides or they may be converted to asparaginyl and glutaminyl residues by reaction with ammonium ions. Conversely, asparaginyl and glutaminyl residues may be deamidated to the corresponding aspartyl or glutamyl residues, respectively, under mildly acidic conditions. Either form of these residues falls within the scope of this invention.

Other modifications that may be formed include the hydroxylation of proline and lysine, phosphorylation of hydroxyl groups of seryl or threonyl groups of lysine, arginine and histidine side chains (T. E. Creighton, *Proteins: Structure and Molecular Properties*, W.H. Freeman & Co., San Francisco, pp. 79-86, 1983), acetylation of the N-terminal amine and amidation of any C-terminal carboxyl group.

As can be seen, modifications of the nucleic sequence encoding AIK may be accomplished by a variety of well-known techniques, such as site-directed mutagenesis (see, Gillman and Smith, *Gene* 8: 81-97 (1979) and Roberts, S. et al., *Nature* 328: 731-734 (1987)). When modifications are made, these modifications may optionally be evaluated for there affect on a variety of different properties including, for example, solubility, crystallizability and a modification to the protein's structure and activity.

In one variation, the variant and/or fragment of wild-type AIK is functional in the sense that the resulting protein is capable of associating with at least one same chemical entity that is also capable of selectively associating with a protein comprising the kinase domain of wild-type AIK (e.g., residues 125-391 of SEQ. ID No. 1) since this common associative ability evidences that at least a portion of the native structure has been conserved.

It is noted the activity of the native protein need not necessarily be conserved. Rather, amino acid substitutions, additions or deletions that interfere with native activity but which do not significantly alter the three-dimensional structure of the domain are specifically contemplated by the invention. Crystals comprising such variants of AIK, and the atomic structure coordinates obtained there from, can be used to identify compounds that bind to the native domain. These compounds may affect the activity or the native domain.

Amino acid substitutions, deletions and additions that do not significantly interfere with the three-dimensional structure of AIK will depend, in part, on the region where the substitution, addition or deletion occurs in the crystal structure. These modifications to the protein can now be made far more intelligently with the crystal structure information provided herein. In highly variable regions of the molecule, non-conservative substitutions as well as conservative substitutions may be tolerated without significantly disrupting the three-dimensional structure of the molecule. In highly conserved regions, or regions containing significant secondary structure, conservative amino acid substitutions are preferred.

Conservative amino acid substitutions are well known in the art, and include substitutions made on the basis of similarity in polarity, charge, solubility, hydrophobicity, hydrophilicity and/or the amphipathic nature of the amino acid residues involved. For example, negatively charged amino acids include aspartic and glutamic acid; positively charged amino acids include lysine and arginine; amino acids with uncharged polar head groups having similar hydrophilicity values include the following: leucine, isoleucine, valine; glycine, alanine; asparagine, glutamine; serine, threonine; phenylalanine, tyrosine. Other conservative amino acid substitutions are well known in the art.

It should be understood that the protein may be produced in whole or in part by chemical synthesis. As a result, the selection of amino acids available for substitution or addition is not limited to the genetically encoded amino acids. Indeed, mutants may optionally contain non-genetically encoded amino acids. Conservative amino acid substitutions for many of the commonly known non-genetically encoded amino acids are well known in the art. Conservative substitutions for other amino acids can be determined based on their physical properties as compared to the properties of the genetically encoded amino acids.

In some instances, it may be particularly advantageous or convenient to substitute, delete and/or add amino acid residues in order to provide convenient cloning sites in cDNA encoding the polypeptide, to aid in purification of the polypeptide, etc. Such substitutions, deletions and/or additions which do not substantially alter the three dimensional structure of AIK will be apparent to those having skills in the art, particularly in view of the three dimensional structure of AIK provided herein.

2. Cloning, Expression and Purification of AIK

The gene encoding AIK can be isolated from RNA, cDNA or cDNA libraries. In this case, the portion of the gene encoding residues 125-391 was isolated and is shown as SEQ. I.D. No. 2.

Construction of expression vectors and recombinant proteins from the DNA sequence encoding AIK may be performed by various methods well known in the art. For example, these techniques may be performed according to Sambrook et al., Molecular Cloning-A Laboratory Manual, Cold Spring Harbor, N.Y. (1989), and Kriegler, M., Gene Transfer and Expression, A Laboratory Manual, Stockton Press, New York (1990).

A variety of expression systems and hosts may be used for the expression of AIK. Example 1 provides one such expression system.

Once expressed, purification steps are employed to produce AIK in a relatively homogeneous state. In general, a higher purity solution of a protein increases the likelihood that the protein will crystallize. Typical purification methods include the use of centrifugation, partial fractionation, using salt or organic compounds, dialysis, conventional column chromatography, (such as ion exchange, molecular sizing chromatography, etc.), high performance liquid chromatography (HPLC), and gel electrophoresis methods (see, e.g., Deutcher, "Guide to Protein Purification" in Methods in Enzymology (1990), Academic Press, Berkeley, Calif.).

AIK may optionally be affinity labeled during cloning, preferably with a poly-histidine ($His_6$) region, in order to facilitate purification. With the use of an affinity label, it is possible to perform a one-step purification process on a purification column that has a unique affinity for the label. The affinity label may be optionally removed after purification. These and other purification methods are known and will be apparent to one of skill in the art.

3. Crystallization & Crystals Comprising AIK

One aspect of the present invention relates to methods for forming crystals comprising AIK as well as crystals comprising AIK.

In one embodiment, a method for forming crystals comprising AIK is provided comprising forming a crystallization volume comprising AIK, precipitant, optionally a buffer, optionally a monovalent or divalent salt and optionally an organic solvent; and storing the crystallization volume under conditions suitable for crystal formation.

In another embodiment, a method for forming crystals comprising AIK is provided comprising forming a crystallization volume comprising AIK, one or more precipitants selected from the group comprising ethylene glycol, polyethylene glycol, glycerol, MPD or ammonium salt (or mixtures thereof), optionally a buffer, optionally a monovalent or divalent salt and optionally an organic solvent; and storing the crystallization volume under conditions suitable for crystal formation.

In yet another embodiment, a method for forming crystals comprising AIK is provided comprising forming a crystallization volume comprising AIK in solution comprising the components shown in Table 5; and storing the crystallization volume under conditions suitable for crystal formation.

TABLE 5

Precipitant 1-50% w/v comprising one or more of MPD, PEG 100-6000, PEG MME 550-5000, ammonium salt, glycerol and ethylene glycol pH pH 6.5-10. Buffers that may be used include, but are not limited to MES, TRIS, CHES, cacodylate, bicine, imidazole, acetate, hepes, citrate, and combinations thereof.

Protein Concentration 1 mg/ml-50 mg/ml

Temperature

4° C.-25° C.

In yet another embodiment, a method for forming crystals comprising AIK is provided comprising forming a crystallization volume comprising AIK; introducing crystals comprising AIK as nucleation sites, and storing the crystallization volume under conditions suitable for crystal formation.

Crystallization experiments may optionally be performed in volumes commonly used in the art, for example typically 15, 10, 5, 2 microliters or less. It is noted that the crystallization volume optionally has a volume of less than 1 microliter, optionally 500, 250, 150, 100, 50 or less nanoliters.

It is also noted that crystallization may be performed by any crystallization method including, but not limited to batch, dialysis and vapor diffusion (e.g., sitting drop and hanging drop) methods. Micro and/or macro seeding of crystals may also be performed to facilitate crystallization.

It should be understood that forming crystals comprising AIK and crystals comprising AIK according to the invention are not intended to be limited to the wild-type, full length AIK shown in SEQ. ID No. 1 and to fragments comprising residues 125-391 or 126-388 of SEQ. ID No. 1. Rather, it should be recognized that the invention may be extended to various other fragments and variants of wild-type AIK as described above.

It should also be understood that forming crystals comprising AIK and crystals comprising AIK according to the invention may be such that AIK is complexed with one or more ligands. The ligand used to form the complex may be any ligand capable of binding to AIK. In one variation, the ligand is a natural substrate. In another variation, the ligand is an inhibitor.

In one particular variation, the ligand binds to the ATP binding site of the protein. Examples of such ligands include, but are not limited to, small molecule inhibitors of AIK as well as ATP, non-hydrolyzable ATP analogs and suicide substrates. Non-hydrolyzable ATP analogs useful in the crystallizable compositions of this invention include AMP-$PCH_2P$, AMP-PNP, AMP-PSP and AMP where the oxygen linking the second and third phosphates of the ATP analogs is replaced by $CH_2$, S (ATPγS) and NH, respectively. An example of a suicidal substrate is 5'-(p-fluorosulfonyl benzoyl) adenosine (FSBA). Preferably, the crystallizable compositions of this invention comprise ATPγS as the substrate.

Optionally, the AIK complex may further comprise divalent cations, especially magnesium or manganese cations, which may be introduced in any suitable manner. For example, the cations may be introduced by incubating the desired ligand with a suitable metal salt such as $MgCl_2$ prior to incubation with the AIK protein.

In one particular embodiment, AIK crystals have a crystal lattice in the $P6_122$ space group. AIK crystals may also optionally have unit cell dimensions, +/−5%, of a=80.45 Å, b=80.45 Å and c=172.18 Å.

AIK crystals also preferably are capable of diffracting X-rays for determination of atomic coordinates to a resolution of 4 Å, 3 Å, 2.5 Å, 2 Å or greater.

Crystals comprising AIK may be formed by a variety of different methods known in the art. For example, crystallizations may be performed by batch, dialysis, and vapor diffusion (sitting drop and hanging drop) methods. A detailed description of basic protein crystallization setups may be found in McRee, D. and David. P., *Practical Protein Crystallography* 2$^{nd}$ Ed. (1999), Academic Press Inc. Further descriptions regarding performing crystallization experiments are provided in Stevens, et al. (2000) *Curr. Opin. Struct. Biol.*: 10(5): 558-63, and U.S. Pat. Nos. 6,296,673, 5,419,278, and 5,096,676.

In one variation, crystals comprising AIK are formed by mixing substantially pure AIK with an aqueous buffer containing a precipitant at a concentration just below a concentration necessary to precipitate the protein. One suitable precipitant for crystallizing AIK is polyethylene glycol (PEG), which combines some of the characteristics of the salts and other organic precipitants (see, for example, Ward et al., *J. Mol. Biol.* 98: 161, 1975, and McPherson, *J. Biol. Chem.* 251: 6300, 1976).

During a crystallization experiment, water is removed by diffusion or evaporation to increase the concentration of the precipitant, thus creating precipitating conditions for the protein. In one particular variation, crystals are grown by vapor diffusion in hanging drops or sitting drops. According to these methods, a protein/precipitant solution is formed and then allowed to equilibrate in a closed container with a larger aqueous reservoir having a precipitant concentration for producing crystals. The protein/precipitant solution continues to equilibrate until crystals grow.

By performing submicroliter volume sized crystallization experiments, as detailed in U.S. Pat. No. 6,296,673, effective crystallization conditions for forming crystals of an AIK-ATPγS complex were obtained. In order to accomplish this, systematic broad screen crystallization trials were performed on an AIK-ATPγS complex using the sitting drop technique. In each experiment, a 100 nL mixture of AIK-ATPγS complex and precipitant was placed on a platform positioned over a well containing 100 μL of the precipitating solution. Precipitate and crystal formation was detected in the sitting drops. Fine screening was then carried out for those crystallization conditions that appeared to produce precipitate and/or crystal in the drops.

Based on the crystallization experiments that were performed, a thorough understanding of how different crystallization conditions affect AIK crystallization was obtained. Based on this understanding, a series of crystallization conditions were identified that may be used to form crystals comprising AIK. These conditions are summarized in Table 5. A particular example of crystallization conditions that may be used to form crystals diffraction quality crystals of the AIK-ATPγS complex is detailed in Example 2. FIG. 2 illustrates crystals of the AIK-ATPγS complex formed using the crystallization conditions provided in Table 5.

One skilled in the art will recognize that the crystallization conditions provided in Table 5 and Example 2 can be varied and still yield protein crystals comprising AIK. For example, it is noted that variations on the crystallization conditions described herein can be readily determined by taking the conditions provided in Table 5 and performing fine screens around those conditions by varying the type and concentration of the components in order to determine additional suitable conditions for crystallizing AIK, variants of AIK, and ligand complexes thereof.

Crystals comprising AIK have a wide range of uses. For example, now that crystals comprising AIK have been produced, it is noted that crystallizations may be performed using such crystals as a nucleation site within a concentrated protein solution. According to this variation, a concentrated protein solution is prepared and a crystalline material (microcrystals) is used to 'seed' the protein solution to assist nucleation for crystal growth. If the concentrations of the protein and any precipitants are optimal for crystal growth, the seed crystal will provide a nucleation site around which a larger crystal forms. Given the ability to form crystals comprising AIK according to the present invention, the crystals so formed can be used by this crystallization technique to initiate crystal growth of other AIK comprising crystals, including AIK complexed to other ligands.

As will be described herein in greater detail, crystals may also be used to perform X-ray or neutron diffraction analysis in order to determine the three-dimensional structure of AIK and, in particular, to assist in the identification of its active site. Knowledge of the binding site region allows rational design and construction of ligands including inhibitors. Crystallization and structural determination of AIK mutants having altered bioactivity allows the evaluation of whether such changes are caused by general structure deformation or by side chain alterations at the substitution site.

4. X-Ray Data Collection and Structure Determination

Crystals comprising AIK may be obtained as described above in Section 3. As described herein, these crystals may then be used to perform x-ray data collection and for structure determination.

In one embodiment, described in Example 2, crystals of an AIK-ATPγS complex were obtained where AIK has the sequence of residues shown in SEQ. ID No. 3 (the $His_6$ affinity tag was removed after purification). These particular crystals were used to determine the three dimensional structure of AIK. However, it is noted that other crystals comprising AIK including different AIK variants, fragments, and complexes thereof may also be used.

Diffraction data was collected from cryocooled crystals (100K) of the AIK-ATPγS complex at the Advanced Light Source beam line 5.0.3 using an ADSC CCD detector. The diffraction pattern of the AIK-ATPγS complex displayed symmetry consistent with space group $P6_122$, with unit cell dimensions of a=80.45 Å, b=80.45 Å and c=172.18 Å. Data were collected and integrated to 1.9 Å with MOSFLM and scaled with SCALA (CCP4 Study Weekend (eds. Sawyer, L., Isaacs, N. & Bailey, S.) 56-62 (SERC Daresbury Laboratory, England) (1993).

All crystallographic calculations were performed using the CCP4 program package (Collaborative Computational Project, N. The CCP4 Suite: Programs for Protein Crystallography. *Acta Cryst.* D50, 760-763 (1994)). The initial phases for AIK were obtained by the molecular replacement method using the program AMORE. The coordinates of yeast cAPK (PDB code 1FOT) were used as a search model (38% identity) for the solution of the AIK-ATPγS structure. The highest solution from the translational function was subjected to a rigid body rotation followed by refinement against the maximum likelihood method as implemented in REFMAC (CCP4). Rigid body refinement and torsional dynamics refinement was followed by multiple rounds of manual building with Xfit (McRee, D. E. XtalView/Xfit-A versatile program for manipulating atomic coordinates and electron density *J. Struct. Biol.* 125, 156-65 (1999)) and/or ARP_WARP map improvement (Perrakis, A., Morris, R. J. & Lamzin, V. S. Automated protein model building combined with iterative structure refinement). All stages of model refinement were carried with bulk solvent correction and anisotropic scaling. The data collection and data refinement statistics are given in Table 6.

TABLE 6

| Crystal data | |
| --- | --- |
| Ligand | ATPγS |
| Space group | $P6_122$ |
| Unit cell dimensions | a = b = 80.45 Å and c = 172.18 Å |

TABLE 6-continued

| Data collection | | AIK-ATPγS |
|---|---|---|
| X-ray source | | Bl 5.0.3 |
| Wavelength [Å] | | 1.0 |
| Resolution [Å] | | 44-1.9 |
| Observations (unique) | | 28,879 |
| Redundancy | | 7.4 |
| Completeness | overall (outer shell) | 98% (93%) |
| I/σ(I) | overall (outer shell) | 14.5 (1.6) |
| $R_{symm}^{1}$ | overall (outer shell) | 0.086 (0.578) |
| Refinement | | |
| Reflections used | | 25,081 |
| R-factor | | 22.5% |
| $R_{free}$ | | 26.8% |
| r.m.s bonds | | 0.019 |
| r.m.s angles | | 1.99 |

$^{1}R_{symm} = \Sigma_{hkl}\Sigma_i | I(hkl)_i - <I(hkl)> | /\Sigma_{hkl}\Sigma_i<I(hkl)_i>$ over I observations of a reflection hkl Each unit cell comprised one AIK-ATPγS-$(Mg^{2+})_2$ complex. Structure coordinates were determined for this molecule and the refined set of coordinates are presented in FIG. 3.

It is noted that the sequence of the structure coordinates presented in FIG. 3 differ in some regards from the sequence shown in SEQ. ID No. 1.

For some residues, the electron density obtained was insufficient to identify the side chain. As a result, the side chains of these residues were truncated such that a different amino acid is reported. Table 7 summarizes the differences between SEQ. ID No. 1 and the truncated residues appearing in FIG. 3.

TABLE 7

Truncated Residues in The Struectfire Coordinates of FIG. 3.

| | | |
|---|---|---|
| 126R-126A | 171K-170A | 339K-339A |
| 127Q-127A | 175E-175A | 375R-375A |
| 170E-170A | 183E-183A | |

It is also noted that structure coordinates are not reported for some residues because the electron density obtained was insufficient to identify the position of these residues. For FIG. 3, structure coordinates for residues 124-125, 286-287 and 389-391 are not reported.

Those of skill in the art understand that a set of structure coordinates (such as those in FIG. 3) for a protein or a protein-complex or a portion thereof, is a relative set of points that define a shape in three dimensions. Thus, it is possible that an entirely different set of structure coordinates could define a similar or identical shape. Moreover, slight variations in the individual coordinates may have little effect on overall shape. In terms of binding pockets, these variations would not be expected to significantly alter the nature of ligands that could associate with those pockets. The term "binding pocket" as used herein refers to a region of the protein that, as a result of its shape, favorably associates with a ligand These variations in coordinates may be generated because of mathematical manipulations of the AIK structure coordinates. For example, the sets of structure coordinates shown in FIG. 3 could be manipulated by crystallographic permutations of the structure coordinates, fractionalization of the structure coordinates, application of a rotation matrix, integer additions or subtractions to sets of the structure coordinates, inversion of the structure coordinates or any combination of the above.

Alternatively, modifications in the crystal structure due to mutations, additions, substitutions, and/or deletions of amino acids or other changes in any of the components that make up the crystal could also account for variations in structure coordinates. If such variations are within an acceptable standard error as compared to the original coordinates, the resulting three-dimensional shape should be considered to be the same. Thus, for example, a ligand that bound to the active site binding pocket of AIK would also be expected to bind to another binding pocket whose structure coordinates defined a shape that fell within the acceptable error.

Various computational methods may be used to determine whether a particular protein or a portion thereof (referred to here as the "target protein"), typically the binding pocket, has a high degree of three-dimensional spatial similarity to another protein (referred to here as the "reference protein") against which the target protein is being compared.

The process of comparing a target protein structure to a reference protein structure may generally be divided into three steps: 1) defining the equivalent residues and/or atoms for the target and reference proteins, 2) performing a fitting operation between the proteins; and 3) analyzing the results. These steps are described in more detail below. All structure comparisons reported herein and the structure comparisons claimed are intended to be based on the particular comparison procedure described below.

Equivalent residues or atoms can be determined based upon an alignment of primary sequences of the proteins, an alignment of their structural domains or as a combination of both. Sequence alignments generally implement the dynamic programming algorithm of Needleman and Wunsch [*J. Mol. Biol.* 48: 442-453, 1970]. For the purpose of this invention the sequence alignment was performed using the publicly available software program MOE (Chemical Computing Group Inc.) package version 2002.3, as described in the accompanying User's Manual. When using the MOE program, alignment was performed in the sequence editor window using the ALIGN option utilizing the following program parameters: Initial pairwise Build-up: ON, Substitution Matrix: Blosum62, Round Robin: ON, Gap Start: 7, Gap Extend: 1, Iterative Refinement: ON, Build-up: TREE-BASED, Secondary Structure: NONE, Structural Alignment: ENABLED, Gap Start: 1, Gap Extend: 0.1

Once aligned, a rigid body fitting operation is performed where the structure for the target protein is translated and rotated to obtain an optimum fit relative to the structure of the reference protein. The fitting operation uses an algorithm that computes the optimum translation and rotation to be applied to the moving structure, such that the root mean square deviation of the fit over the specified pairs of equivalent atoms is an absolute minimum. For the purpose of fitting operations made herein, the publicly available software program MOE (Chemical Computing Group Inc.) v. 2002.3 was used.

The results from this process are typically reported as an RMSD value between two sets of atoms. The term "root mean square deviation" means the square root of the arithmetic mean of the squares of deviations. It is a way to express the deviation or variation from a trend or object. As used herein, an RMSD value refers to a calculated value based on variations in the atomic coordinates of a reference protein from the atomic coordinates of a reference protein or portions of thereof. The structure coordinates for AIK, provided in FIG. 3, are used as the reference protein in these calculations.

The same set of atoms was used for initial fitting of the structures and for computing root mean square deviation values. For example, if a root mean square deviation (RMSD) between Cα atoms of two proteins is needed, the proteins in question should be superposed only on the Cα atoms and not on any other set of atoms. Similarly, if an RMSD calculation for all atoms is required, the superposition of two structures should be performed on all atoms.

Based on a review of protein structures deposited in the Protein Databank (PDB), 1O6K was identified as having the smallest RMSD values relative to the structure coordinates provided herein. Table 8 below provides a series of RMSD values that were calculated by the above described process using the structure coordinates in FIG. 3 as the reference protein and the structure coordinates from PDB code: 1O6K (Activated Pkb Kinase with GSK3 peptide and ANP-PNP) as the target protein.

TABLE 8

| AA RESIDUES USED TO PERFORM RMSD COMPARISON WITH PDB:1O6K | PORTION OF EACH AA RESIDUE USED TO PERFORM RMSD COMPARISON WITH PDB:1O6K | RMSD [Å] |
|---|---|---|
| Table 2 (4 Angstrom set) | alpha-carbon atoms[1] | 0.89 |
| | main-chain atoms[1] | 0.85 |
| | all non-hydrogen[2] | 1.22 |
| Table 3 (7 Angstrom set) | alpha-carbon atoms[1] | 1.00 |
| | main-chain atoms[1] | 0.93 |
| | all non-hydrogen[2] | 1.32 |
| Table 4 (10 Angstrom set) | alpha-carbon atoms[1] | 1.64 |
| | main-chain atoms[1] | 1.60 |
| | all non-hydrogen[2] | 1.86 |
| 126-388 of SEQ. ID No. 1 | alpha-carbon atoms[1] | 2.33 |
| | main-chain atoms[1] | 2.31 |
| | all non-hydrogen[2] | 2.38 |

[1] the RMSD computed between the atoms of all amino acids that are common to both the target and the reference in the aligned and superposed structure. The amino acids need not to be identical.
[2] the RMSD computed only between identical amino acids, which are common to both the target and the reference in the aligned and superposed structure.

It is noted that mutants and variants of AIK as well as other kinase are likely to have similar structures despite having different sequences. For example, the binding pockets of these related proteins are likely to have similar contours. Accordingly, it should be recognized that the structure coordinates and binding pocket models provided herein have utility for these other related proteins.

Accordingly, in one embodiment, the invention relates to data, computer readable media comprising data, and uses of the data where the data comprises all or a portion of the structure coordinates shown in FIG. 3 or structure coordinates having a root mean square deviation (RMSD) equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1.

As noted, there are many different ways to express the surface contours of the AIK structure other than by using the structure coordinates provided in FIG. 3. Accordingly, it is noted that the present invention is also directed to any data, computer readable media comprising data, and uses of the data where the data defines a computer model for a protein binding pocket, at least a portion of the computer model having a surface contour that has a root mean square deviation equal to or less than a given RMSD value specified in Columns 3, 4 or 5 of Table 1 when the coordinates used to compute the surface contour are compared to the structure coordinates of FIG. 3, wherein (a) the root mean square deviation is calculated by the calculation method set forth herein, (b) the portion of amino acid residues associated with the given RMSD value in Table 1 (specified in Column 2 of Table 1) are superimposed according to the RMSD calculation, and (c) the root mean square deviation is calculated based only on those amino acid residues present in both the protein being modeled and the portion of the protein associated with the given RMSD in Table 1 (specified in Column 1 of Table 1).

5. AIK-ATPγS Structure

The present invention is also directed to a three-dimensional crystal structure of AIK. This crystal structure may be used to identify binding sites, to provide mutants having desirable binding properties, and ultimately, to design, characterize, or identify ligands that interact with AIK.

The three-dimensional crystal structure of AIK may be generated, as is known in the art, from the structure coordinates shown in FIG. 3 and similar such coordinates.

The refined crystal structure of AIK-ATPγS determined according to the present invention contains amino acids residues 126-388 as numbered according to SEQ. ID No. 1 (based on the coordinates of FIG. 3), one bound ATPγS molecule, and two $Mg^{2+}$ ions. A total of 73 water molecules were included.

Figure 4:
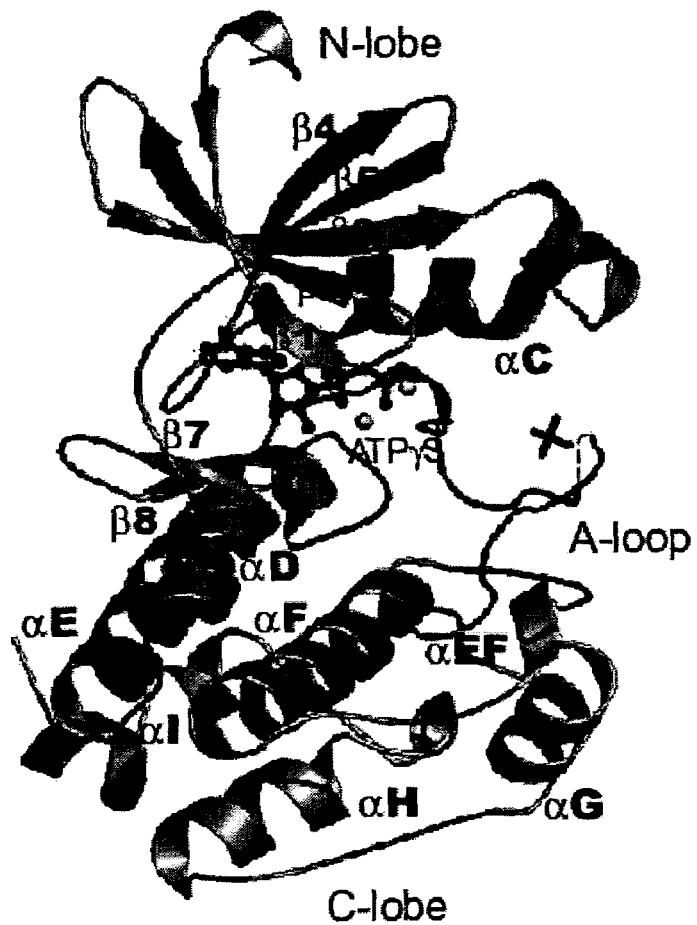
FIG. 4 illustrates a ribbon diagram overview of the structure of AIK, highlighting the secondary structural elements of the protein.

FIG. 4 illustrates a ribbon diagram overview of the structure of AIK, highlighting the secondary structural elements of the protein. As can be seen, the structure exhibits bilobal architecture typical of protein kinase catalytic domains. The smaller N-terminal lobe contains a five-stranded anti-parallel β-sheet (β1-β5) and an α-helix (αC). The larger C-terminal lobe consists of eight α-helices (αD-αJ). The C-terminal lobe contains functionally important loop regions: the glycine-rich nucleotide binding loop, the catalytic loop and the activation loop (A-loop) involved in polypeptide substrate binding. The nucleotide ligands bind in a cleft between the two lobes.

Kinases show considerable variability in the relative orientation of the N and C lobes, in the position and orientation of the αC, and in the conformation of the activation loop. This relative orientation of the N- and C-terminal lobes is important in kinase function. A catalytically active conformation is generally a closed structure in which the two lobes clamp together bringing conserved residues into catalytically optimal positions. In particular, in the active conformation, the αC helix becomes parallel with the cleft between the lobes and makes tertiary contacts with the C-lobe. In the inactive conformation observed in several unphosphorylated kinase structures the two lobes are spaced apart at a much higher angle and the αC helix is rotated away from the C-lobe.

The conformation of AIK closely resembles the closed, active conformations of cAPK, and cyclin-dependent kinase 2 (cdk2). The αC helix adopts the active conformation. The two lobes clamp together, bringing residues of the catalytic cleft into alignment.

Figure 5:
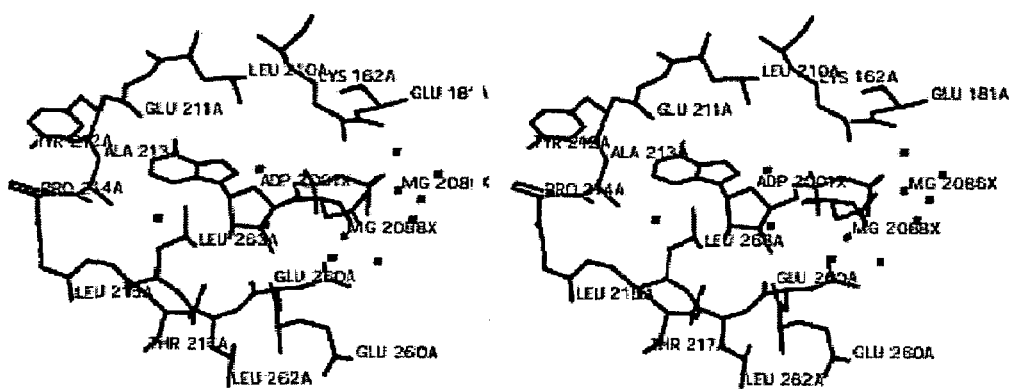
FIG. 5 illustrates ATPγS bound in the active site of AIK based on the determined crystal structure for the molecule in the asymmetric unit corresponding to the structure coordinates shown in FIG. 3.

FIG. 5 illustrates ATPγS bound in the active site of AIK based on the determined crystal structure for the molecule in the asymmetric unit corresponding to the structure coordinates shown in FIG. 3.

The αC helix is positioned so that the conserved residue E181 makes a salt bridge with K162, in close proximity to the β-phosphate of the bound ADP ligand (FIG. 4). The activation loop (A-loop; residues 274-297) is well ordered with the exception of residues 286 and 287. The loop is stabilized by numerous interactions both within the loop and with other regions of the kinase. Residues 278-279 and 282-283 form two short stretches of anti-parallel beta sheet with residues 252-253 and 305-306 respectively, and the side chain of R285 forms a hydrogen bond with the backbone of 1301. Those contacts anchor the N-terminal portion of the activation loop to the core of the C-terminal lobe. The conformation of the A-loop allows access to the substrate-binding site. The observation of an active AIK conformation was unanticipated since most kinases require phosphorylation of their activation loop to adopt the active conformation. Although unphosphorylated protein was used in crystallization, there is a free phosphate ion bound 1.3 Å from the Oγ of T288. The phosphate is bound in a pocket created by side chains of R180, H176 and R255. These side chains are in positions analogous to those in phosphorylated, activated kinases, suggesting that the phosphate-bound AIK structure mimics a catalytically active conformation.

The similarity of the phosphate binding pocket and the overall structure of AIK and other activated kinases suggests that the phosphate-bound AIK structure mimics the active, phosphorylated state of the enzyme. It is likely that the activation of AIK follows a similar mechanism as the activation of cdk2 and cAPK. In the unphosphorylated state, the A-loop blocks the access of the substrate to the catalytic cleft. Upon phosphorylation, the phosphate group acts as an organizing center that induces conformational change in the A-loop by moving it into a position that allows productive substrate binding and catalysis.

6. AIK Binding Pocket and Ligand Interaction

The term "binding site" or "binding pocket", as the terms are used herein, refers to a region of a protein that, as a result of its shape, favorably associates with a ligand or substrate. The term "AIK-like binding pocket" refers to a portion of a molecule or molecular complex whose shape is sufficiently similar to the AIK binding pockets as to bind common ligands. This commonality of shape may be quantitatively defined by a root mean square deviation (rmsd) from the structure coordinates of the backbone atoms of the amino acids that make up the binding pockets in AIK (as set forth in FIG. 3).

The "active site binding pockets" or "active site" of AIK refers to the area on the surface of AIK where the substrate binds.

FIG. 5 illustrates ATPγS bound in the active site of AIK based on the determined crystal structure of the present invention. As can be seen, ATPγS binds in a cleft between the two lobes and is coordinated by residues on the N-terminal lobe. Residues in the C-terminal lobe coordinate substrate binding and catalysis. Although the ATPγS was used during crystallization, the γ-phosphate is not visible in the structure suggesting hydrolysis driven by a high pH of the crystallization conditions. The ATPγS interacts with the protein through both direct and water mediated contacts. The adenine base inserts into a hydrophobic pocket formed by the side chains of L139, V147, L210, Y212, A213 and L263. The N1 nitrogen and amino group of the adenine ring hydrogen bond to the main chain of A213 and E211. The ribose moiety is anchored to the protein via hydrogen bonding between 3'OH and the carbonyl of E260. The active site of AIK displays a network of ordered water molecules that participate in hydrogen bonding within the binding site. Two fully coordinated $Mg^{2+}$ ions are present in the AIK structure. Both metal ions are directly coordinated by the side chain of D274 and bridge the α- and β-phosphates of ATPγS.

The ATP binding site of protein kinases is a primary target for the design of small molecule inhibitors. The ATP binding site appears well conserved among protein kinases and involves residues protruding from the β1-β2-β3 sheet, helix C, the loop region linking β5 and the C-lobe, and the catalytic loop. The structure of the ATP binding pocket in the AIK-ATPγS complex shows considerable sequence variability with other kinases, which is reflective of diversity among kinase sub-families. The ATP binding cleft shows subtle differences in ATP site architecture that may be explored to confer specificity of inhibition. The position of the bound ATPγS is similar, but not identical, to other structures.

In resolving the crystal structure of AIK in complex with ATPγS, applicants determined that AIK amino acids in Table 2 (above) are within 4 Angstroms of and therefore close enough to interact with ATPγS. Applicants have also determined that the amino acids of Table 3 (above) are within 7 Angstroms of bound ATPγS and therefore are also close enough to interact with that substrate or analogs thereof. Further it has been determined that the amino acids of Table 4 (above) are within 10 Angstroms of the bound ATPγS. The 4, 7, and/or 10 Angstroms sets of amino acids are preferably conserved in variants of AIK. While it is desirable to largely conserve these residues, it should be recognized however that variants may also involve varying 1, 2, 3, 4 or more of the residues set forth in Tables 2, 3, and 4 in order to evaluate the roles these amino acids play in the binding pocket.

With the knowledge of the AIK crystal structure provided herein, Applicants define an AIK binding pocket as a binding pocket where the relative positioning of the 4, 7, and/or 10 Angstroms sets of amino acids are substantially conserved. Again, it is noted that it may be desirable to form variants where 1, 2, 3, 4 or more of the residues set forth in Tables 2, 3, and 4 are varied in order to evaluate the roles these amino acids play in the binding pocket. Accordingly, any set of structure coordinates for a protein from any source having a root mean square deviation of non-hydrogen atoms of less than 2 Å when superimposed on the non-hydrogen atom positions of the corresponding atomic coordinates of FIG. 3 for the 4, 7, and/or 10 Angstroms sets of amino acids shall be considered identical. As noted previously, the root mean square deviation is intended to be limited to only those non-hydrogen atoms of amino acid residues that are common to both the protein fragment represented in FIG. 3 and the protein whose structure coordinates are being compared to the coordinates shown in FIG. 3 since the sequence of the protein may be varied somewhat.

Accordingly, in one embodiment, the invention relates to data, computer readable media comprising data, and uses of the data where the data comprises the structure coordinates shown in FIG. 3 or structure coordinates having a root mean square deviation of non-hydrogen atoms of less than 3 Å when superimposed on the non-hydrogen atom positions of the corresponding atomic coordinates of FIG. 3 for the 4, 7, and/or 10 Angstroms sets of amino acids.

Again, it is noted that the root mean square deviation is intended to be limited to only those non-hydrogen atoms of amino acid residues that are common to both the protein fragment represented in one or more of the tables and the protein whose structure coordinates are being compared to the coordinates shown in FIG. 3.

As noted above, there are many different ways to express the surface contours of the AIK structure other than by using the structure coordinates provided in FIG. 3. Accordingly, it is noted that the present invention is also directed to any data, computer readable media comprising data, and uses of the data where the data defines a computer model for a protein binding pocket, at least a portion of the computer model having a surface contour that has a root mean square deviation of less than 3 Å when superimposed on a surface contour defined by atomic coordinates of FIG. 3, the root mean square deviation being calculated based only on non-hydrogen atoms in the structure coordinates of FIG. 3 that are present in residues shown in Tables 2, 3, and/or 4.

Optionally, the root mean square deviation of non-hydrogen atoms is less than 1.5 Å, 1 Å, 0.5 Å, or less.

It will be readily apparent to those of skill in the art that the numbering of amino acids in other isoforms of AIK may be different than that set forth for AIK. Corresponding amino acids in other isoforms of AIK are easily identified by visual inspection of the amino acid sequences or by using commercially available homology software programs, as further described below.

7. System for Displaying the Three Dimensional Structure of AIK

The present invention is also directed to machine-readable data storage media having data storage material encoded with machine-readable data that comprises structure coordinates for AIK. The present invention is also directed to a machine readable data storage media having data storage material encoded with machine readable data, which, when read by an appropriate machine, can display a three dimensional representation of a structure of AIK.

All or a portion of the AIK coordinate data shown in FIG. 3, when used in conjunction with a computer programmed with software to translate those coordinates into the three-dimensional structure of AIK may be used for a variety of purposes, especially for purposes relating to drug discovery. Software for generating three-dimensional graphical representations are known and commercially available. The ready use of the coordinate data requires that it be stored in a computer-readable format. Thus, in accordance with the present invention, data capable of being displayed as the three-dimensional structure of AIK and/or portions thereof and/or their structurally similar variants may be stored in a machine-readable storage medium, which is capable of displaying a graphical three-dimensional representation of the structure.

For example, in various embodiments, a computer is provided for producing a three-dimensional representation of at least an AIK-like binding pocket, the computer comprising:

machine readable data storage medium comprising a data storage material encoded with machine-readable data, the machine readable data comprising structure coordinates that have a root mean square deviation equal to or less than the RMSD value specified in Columns 3, 4 or of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1;

a working memory for storing instructions for processing the machine-readable data;

a central-processing unit coupled to the working memory and to the machine-readable data storage medium, for processing the machine-readable data into the three-dimensional representation; and an output hardware coupled to the central processing unit, for receiving the three dimensional representation.

Another embodiment of this invention provides a machine-readable data storage medium, comprising a data storage material encoded with machine readable data which, when used by a machine programmed with instructions for using said data, displays a graphical three-dimensional representation comprising AIK or a portion or variant thereof.

In various variations, the machine readable data comprises data for representing a protein based on structure coordinates where the structure coordinates have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1.

According to another embodiment, the machine-readable data storage medium comprises a data storage material encoded with a first set of machine readable data which comprises the Fourier transform of structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1, and which, when using a machine programmed with instructions for using said data, can be combined with a second set of machine readable data comprising the X-ray diffraction pattern of another molecule or molecular complex to determine at least a portion of the structure coordinates corresponding to the second set of machine readable data. For example, the Fourier transform of the structure coordinates set forth in FIG. 3 may be used to determine at least a portion of the structure coordinates of other AIK-like enzymes, and isoforms of AIK.

Optionally, a computer system is provided in combination with the machine-readable data storage medium provided herein. In one embodiment, the computer system comprises a working memory for storing instructions for processing the machine-readable data; a processing unit coupled to the working memory and to the machine-readable data storage medium, for processing the machine-readable data into the three-dimensional representation; and an output hardware coupled to the processing unit, for receiving the three-dimensional representation.

Figure 6:
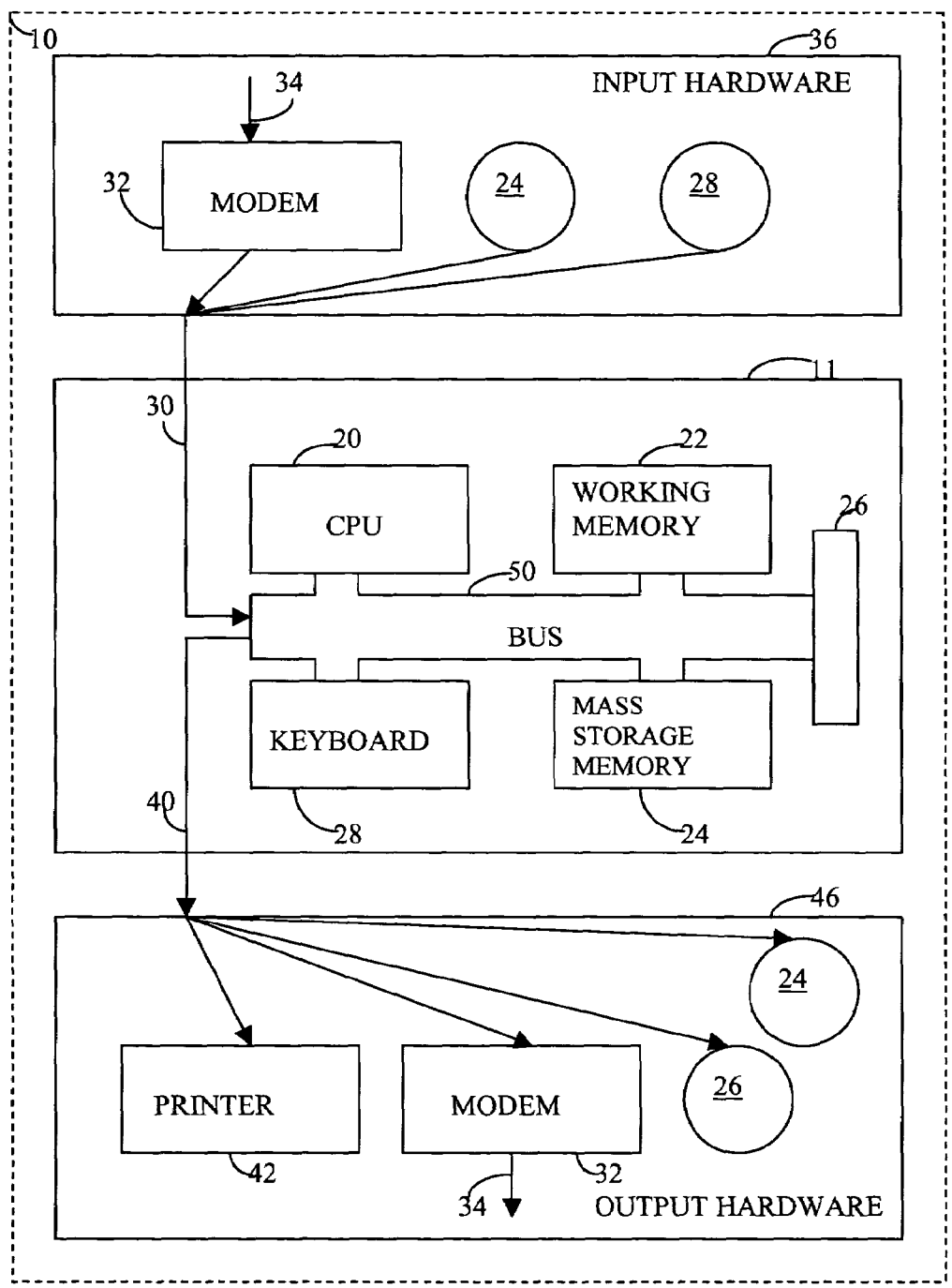
FIG. 6 illustrates a system that may be used to carry out instructions for displaying a crystal structure of AIK encoded on a storage medium.

FIG. 6 illustrates an example of a computer system that may be used in combination with storage media according to the present invention. As illustrated, the computer system 10 includes a computer 11 comprising a central processing unit ("CPU") 20, a working memory 22 which may be, e.g., RAM (random-access memory) or "core" memory, mass storage memory 24 (such as one or more disk drives or CD-ROM drives), one or more cathode-ray tube ("CRT") display terminals 26, one or more keyboards 28, one or more input lines 30, and one or more output lines 40, all of which are interconnected by a conventional bi-directional system bus 50.

Input hardware 36, coupled to computer 11 by input lines 30, may be implemented in a variety of ways. For example, machine-readable data of this invention may be inputted via the use of a modem or modems 32 connected by a telephone line or dedicated data line 34. Alternatively or additionally, the input hardware 36 may comprise CD-ROM drives or disk drives 24. In conjunction with display terminal 26, keyboard 28 may also be used as an input device.

Conventional devices may, similarly implement output hardware 46, coupled to computer 11 by output lines 40. By way of example, output hardware 46 may include CRT display terminal 26 for displaying a graphical representation of a binding pocket of this invention using a program such as MOE as described herein. Output hardware might also include a printer 42, so that hard copy output may be produced, or a disk drive 24, to store system output for later use.

In operation, CPU 20 coordinates the use of the various input and output devices 36, 46 coordinates data accesses from mass storage 24 and accesses to and from working memory 22, and determines the sequence of data processing steps. A number of programs may be used to process the machine-readable data of this invention. Such programs are discussed in reference to using the three dimensional structure of AIK described herein.

The storage medium encoded with machine-readable data according to the present invention can be any conventional data storage device known in the art. For example, the storage medium can be a conventional floppy diskette or hard disk. The storage medium can also be an optically readable data storage medium, such as a CD-ROM or a DVD-ROM, or a rewritable medium such as a magneto-optical disk that is optically readable and magneto-optically writable.

8. Uses of the Three Dimensional Structure of AIK

The three-dimensional crystal structure of the present invention may be used to identify AIK binding sites, be used as a molecular replacement model to solve the structure of unknown crystallized proteins, to design mutants having desirable binding properties, and ultimately, to design, characterize, identify entities capable of interacting with AIK and other structurally similar proteins as well as other uses that would be recognized by one of ordinary skill in the art. Such entities may be chemical entities or proteins. The term "chemical entity", as used herein, refers to chemical compounds, complexes of at least two chemical compounds, and fragments of such compounds.

The AIK structure coordinates provided herein are useful for screening and identifying drugs that inhibit AIK and other structurally similar proteins. For example, the structure encoded by the data may be computationally evaluated for its ability to associate with putative substrates or ligands. Such compounds that associate with AIK may inhibit AIK, and are potential drug candidates. Additionally or alternatively, the structure encoded by the data may be displayed in a graphical three-dimensional representation on a computer screen. This allows visual inspection of the structure, as well as visual inspection of the structure's association with the compounds.

Thus, according to another embodiment of the present invention, a method is provided for evaluating the potential of an entity to associate with AIK or a fragment or variant thereof by using all or a portion of the structure coordinates provided in FIG. 3 or functional equivalents thereof. A method is also provided for evaluating the potential of an entity to associate with AIK or a fragment or variant thereof by using structure coordinates similar to all or a portion of the structure coordinates provided in FIG. 3 or functional equivalents thereof.

The method may optionally comprise the steps of: creating a computer model of all or a portion of a protein structure (e.g., a binding pocket) using structure coordinates according to the present invention; performing a fitting operation between the entity and the computer model; and analyzing the results of the fitting operation to quantify the association between the entity and the model. The portion of the protein structure used optionally comprises all of the amino acids listed in Tables 2, 3 and 4 that are present in the structure coordinates being used.

It is noted that the computer model may not necessarily directly use the structure coordinates. Rather, a computer model can be formed that defines a surface contour that is the same or similar to the surface contour defined by the structure coordinates.

The structure coordinates provided herein can also be utilized in a method for identifying a ligand (e.g., entities capable of associating with a protein) of a protein comprising an AIK-like binding pocket. One embodiment of the method comprises: using all or a portion of the structure coordinates provided herein to generate a three-dimensional structure of an AIK-like binding pocket; employing the three-dimensional structure to design or select a potential ligand; synthesizing the potential ligand; and contacting the synthesized potential ligand with a protein comprising an AIK-like binding pocket to determine the ability of the potential ligand to interact with protein. According to this method, the structure coordinates used may have a root mean square deviation equal to or less than the RMSD values specified in Columns 3, 4 or 5 of Table 1 when compared to the structure coordinates of FIG. 3 according to the RMSD calculation method set forth herein, provided that the portion of amino acid residues specified in Column 2 of Table 1 of each set of structure coordinates are superimposed and the root mean square deviation is calculated based only on those amino acid residues in the structure coordinates that are also present in the portion of the protein specified in Column 1 of Table 1. The portion of the protein structure used optionally comprises all of the amino acids listed in Tables 2, 3, and/or 4 that are present.

As noted previously, the three-dimensional structure of an AIK-like binding pocket need not be generated directly from structure coordinates. Rather, a computer model can be formed that defines a surface contour that is the same or similar to the surface contour defined by the structure coordinates.

A method is also provided for evaluating the ability of an entity, such as a compound or a protein to associate with an AIK-like binding pocket, the method comprising: constructing a computer model of a binding pocket defined by structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1; selecting an entity to be evaluated by a method selected from the group consisting of (i) assembling molecular fragments into the entity, (ii) selecting an entity from a small molecule database, (iii) de novo ligand design of the entity, and (iv) modifying a known ligand for AIK, or a portion thereof; performing a fitting program operation between computer models of the entity to be evaluated and the binding pocket in order to provide an energy-minimized configuration of the entity in the binding pocket; and evaluating the results of the fitting operation to quantify the association between the entity and the binding pocket model in order to evaluate the ability of the entity to associate with the said binding pocket.

The computer model of a binding pocket used in this embodiment need not be generated directly from structure coordinates. Rather, a computer model can be formed that defines a surface contour that is the same or similar to the surface contour defined by the structure coordinates.

Also according to the method, the method may further include synthesizing the entity; and contacting a protein having an AIK-like binding pocket with the synthesized entity.

With the structure provided herein, the present invention for the first time permits the use of molecular design techniques to identify, select or design potential inhibitors of AIK, based on the structure of an AIK-like binding pocket. Such a predictive model is valuable in light of the high costs associated with the preparation and testing of the many diverse compounds that may possibly bind to the AIK protein.

According to this invention, a potential AIK inhibitor may now be evaluated for its ability to bind an AIK-like binding pocket prior to its actual synthesis and testing. If a proposed entity is predicted to have insufficient interaction or association with the binding pocket, preparation and testing of the entity can be obviated. However, if the computer modeling indicates a strong interaction, the entity may then be obtained and tested for its ability to bind.

A potential inhibitor of an AIK-like binding pocket may be computationally evaluated using a series of steps in which chemical entities or fragments are screened and selected for their ability to associate with the AIK-like binding pockets.

One skilled in the art may use one of several methods to screen entities (whether chemical or protein) for their ability to associate with an AIK-like binding pocket. This process may begin by visual inspection of, for example, an AIK-like binding pocket on a computer screen based on the AIK structure coordinates in FIG. 3 or other coordinates which define a similar shape generated from the machine-readable storage medium. Selected fragments or chemical entities may then be positioned in a variety of orientations, or docked, within that binding pocket as defined above. Docking may be accomplished using software such as Quanta and Sybyl, followed by energy minimization and molecular dynamics with standard molecular mechanics force fields, such as CHARMM and AMBER.

Specialized computer programs may also assist in the process of selecting entities. These include: GRID (P. J. Goodford, "A Computational Procedure for Determining Energetically Favorable Binding Sites on Biologically Important Macromolecules", J. Med. Chem., 28, pp. 849-857 (1985)). GRID is available from Oxford University, Oxford, UK; MCSS (A. Miranker et al., "Functionality Maps of Binding Sites: A Multiple Copy Simultaneous Search Method." Proteins: Structure, Function and Genetics, 11, pp. 29-34 (1991)). MCSS is available from Molecular Simulations, San Diego, Calif.; AUTODOCK (D. S. Goodsell et al., "Automated Docking of Substrates to Proteins by Simulated Annealing", Proteins: Structure, Function, and Genetics, 8, pp. 195-202 (1990)). AUTODOCK is available from Scripps Research Institute, La Jolla, Calif.; & DOCK (I. D. Kuntz et al., "A Geometric Approach to Macromolecule-Ligand Interactions", J. Mol. Biol., 161, pp. 269-288 (1982)). DOCK is available from University of California, San Francisco, Calif.

Once suitable entities have been selected, they can be designed or assembled. Assembly may be preceded by visual inspection of the relationship of the fragments to each other on the three-dimensional image displayed on a computer screen in relation to the structure coordinates of AIK. This may then be followed by manual model building using software such as MOE, QUANTA or Sybyl [Tripos Associates, St. Louis, Mo].

Useful programs to aid one of skill in the art in connecting the individual chemical entities or fragments include: CAVEAT (P. A. Bartlett et al, "CAVEAT: A Program to Facilitate the Structure-Derived Design of Biologically Active Molecules", in "Molecular Recognition in Chemical and Biological Problems", Special Pub., Royal Chem. Soc., 78, pp. 182-196 (1989); G. Lauri and P. A. Bartlett, "CAVEAT: a Program to Facilitate the Design of Organic Molecules", J. Comput. Aided Mol. Des., 8, pp. 51-66 (1994)). CAVEAT is available from the University of California, Berkeley, Calif.; 3D Database systems such as ISIS (MDL Information Systems, San Leandro, Calif.). This area is reviewed in Y. C. Martin, "3D Database Searching in Drug Design", J. Med. Chem., 35, pp. 2145-2154 (1992); HOOK (M. B. Eisen et al, "HOOK: A Program for Finding Novel Molecular Architectures that Satisfy the Chemical and Steric Requirements of a Macromolecule Binding Site", Proteins: Struct., Funct., Genet., 19, pp. 199-221 (1994). HOOK is available from Molecular Simulations, San Diego, Calif.

Instead of proceeding to build an inhibitor of an AIK-like binding pocket in a step-wise fashion one fragment or entity at a time as described above, inhibitory or other AIK binding compounds may be designed as a whole or "de novo" using either an empty binding site or optionally including some portion(s) of a known inhibitor(s). There are many de novo ligand design methods including: LUDI (H.-J. Bohm, "The Computer Program LUDI: A New Method for the De Novo Design of Enzyme Inhibitors", J. Comp. Aid. Molec. Design, 6, pp. 61-78 (1992)). LUDI is available from Molecular Simulations Incorporated, San Diego, Calif.; LEGEND (Y. Nishibata et al., Tetrahedron, 47, p. 8985 (1991)). LEGEND is available from Molecular Simulations Incorporated, San Diego, Calif.; LEAPFROG (available from Tripos Associates, St. Louis, Mo.); & SPROUT (V. Gillet et al, "SPROUT: A Program for Structure Generation)", J. Comput. Aided Mol. Design, 7, pp. 127-153 (1993)). SPROUT is available from the University of Leeds, UK.

Other molecular modeling techniques may also be employed in accordance with this invention (see, e.g., Cohen et al., "Molecular Modeling Software and Methods for Medicinal Chemistry, J. Med. Chem., 33, pp. 883-894 (1990); see also, M. A. Navia and M. A. Murcko, "The Use of Structural Information in Drug Design", Current Opinions in Structural Biology, 2, pp. 202-210 (1992); L. M. Balbes et al., "A Perspective of Modem Methods in Computer-Aided Drug Design", in Reviews in Computational Chemistry, Vol. 5, K. B. Lipkowitz and D. B. Boyd, Eds., VCH, New York, pp. 337-380 (1994); see also, W. C. Guida, "Software For Structure-Based Drug Design", Curr. Opin. Struct. Biology, 4, pp. 777-781 (1994)).

Once an entity has been designed or selected, for example, by the above methods, the efficiency with which that entity may bind to an AIK binding pocket may be tested and optimized by computational evaluation. For example, an effective AIK binding pocket inhibitor preferably demonstrates a relatively small difference in energy between its bound and free states (i.e., a small deformation energy of binding). Thus, the most efficient AIK binding pocket inhibitors should preferably be designed with deformation energy of binding of not greater than about 10 kcal/mole, more preferably, not greater than 7 kcal/mole. AIK binding pocket inhibitors may interact with the binding pocket in more than one of multiple conformations that are similar in overall binding energy. In those cases, the deformation energy of binding is taken to be the difference between the energy of the free entity and the average energy of the conformations observed when the inhibitor binds to the protein.

An entity designed or selected as binding to an AIK binding pocket may be further computationally optimized so that in its bound state it would preferably lack repulsive electrostatic interaction with the target enzyme and with the surrounding water molecules. Such non-complementary electrostatic interactions include repulsive charge-charge, dipole-dipole and charge-dipole interactions.

Specific computer software is available in the art to evaluate compound deformation energy and electrostatic interactions. Examples of programs designed for such uses include:

Gaussian 94, revision C (M. J. Frisch, Gaussian, Inc., Pittsburgh, Pa. COPYRGT 1995); AMBER, version 4.1 (P. A. Kollman, University of California at San Francisco, COPYRGT 1995); QUANTA/CHARMM (Molecular Simulations, Inc., San Diego, Calif. COPYRGT 1995); Insight II/Discover (Molecular Simulations, Inc., San Diego, Calif. COPYRGT 1995); DelPhi (Molecular Simulations, Inc., San Diego, Calif. COPYRGT 1995); and AMSOL (Quantum Chemistry Program Exchange, Indiana University). These programs may be implemented, for instance, using a Silicon Graphics workstation such as an Indigo.sup.2 with "IMPACT" graphics. Other hardware systems and software packages will be known to those skilled in the art.

Another approach provided by this invention, is the computational screening of small molecule databases for chemical entities or compounds that can bind in whole, or in part, to an AIK binding pocket. In this screening, the quality of fit of such entities to the binding site may be judged either by shape complementarities or by estimated interaction energy [E. C. Meng et al., J. Comp. Chem., 13, 505-524 (1992)].

According to another embodiment, the invention provides compounds that associate with an AIK-like binding pocket produced or identified by various methods set forth above.

The structure coordinates set forth in FIG. 3 can also be used to aid in obtaining structural information about another crystallized molecule or molecular complex. This may be achieved by any of a number of well-known techniques, including molecular replacement.

For example, a method is also provided for utilizing molecular replacement to obtain structural information about a protein whose structure is unknown comprising the steps of: generating an X-ray diffraction pattern of a crystal of the protein whose structure is unknown; generating a three-dimensional electron density map of the protein whose structure is unknown from the X-ray diffraction pattern by using at least a portion of the structure coordinates set forth in FIG. 3 as a molecular replacement model.

By using molecular replacement, all or part of the structure coordinates of the AIK provided by this invention (and set forth in FIG. 3) can be used to determine the structure of another crystallized molecule or molecular complex more quickly and efficiently than attempting an ab initio structure determination. One particular use includes use with other structurally similar proteins. Molecular replacement provides an accurate estimation of the phases for an unknown structure. Phases are a factor in equations used to solve crystal structures that cannot be determined directly. Obtaining accurate values for the phases, by methods other than molecular replacement, is a time-consuming process that involves iterative cycles of approximations and refinements and greatly hinders the solution of crystal structures. However, when the crystal structure of a protein containing at least a homologous portion has been solved, the phases from the known structure provide a satisfactory estimate of the phases for the unknown structure.

Thus, this method involves generating a preliminary model of a molecule or molecular complex whose structure coordinates are unknown, by orienting and positioning the relevant portion of AIK according to FIG. 3 within the unit cell of the crystal of the unknown molecule or molecular complex so as best to account for the observed X-ray diffraction pattern of the crystal of the molecule or molecular complex whose structure is unknown. Phases can then be calculated from this model and combined with the observed X-ray diffraction pattern amplitudes to generate an electron density map of the structure whose coordinates are unknown. This, in turn, can be subjected to any well-known model building and structure refinement techniques to provide a final, accurate structure of the unknown crystallized molecule or molecular complex [E. Lattman, "Use of the Rotation and Translation Functions", in Meth. Enzymol., 115, pp. 55-77 (1985); M. G. Rossmann, ed., "The Molecular Replacement Method", Int. Sci. Rev. Ser., No. 13, Gordon & Breach, New York (1972)].

The structure of any portion of any crystallized molecule or molecular complex that is sufficiently homologous to any portion of AIK can be resolved by this method.

In one embodiment, the method of molecular replacement is utilized to obtain structural information about the present invention and any other AIK-like molecule. The structure coordinates of AIK, as provided by this invention, are particularly useful in solving the structure of other isoforms of AIK or AIK complexes.

The structure coordinates of AIK as provided by this invention are useful in solving the structure of AIK variants that have amino acid substitutions, additions and/or deletions (referred to collectively as "AIK mutants", as compared to naturally occurring AIK). These AIK mutants may optionally be crystallized in co-complex with a ligand, such as an inhibitor, substrate analogue or a suicide substrate. The crystal structures of a series of such complexes may then be solved by molecular replacement and compared with that of AIK. Potential sites for modification within the various binding sites of the enzyme may thus be identified. This information provides an additional tool for determining the most efficient binding interactions such as, for example, increased hydrophobic interactions, between AIK and a ligand. It is noted that the ligand may be the protein's natural ligand or may be a potential agonist or antagonist of a protein.

All of the complexes referred to above may be studied using well-known X-ray diffraction techniques and may be refined versus 1.5-3 Å resolution X-ray data to an R value of about 0.22 or less using computer software, such as X-PLOR [Yale University, COPYRIGHT. 1992, distributed by Molecular Simulations, Inc.; see, e.g., Blundell & Johnson, supra; Meth. Enzymol., Vol. 114 & 115, H. W. Wyckoff et al., eds., Academic Press (1985)]. This information may thus be used to optimize known AIK inhibitors, and more importantly, to design new AIK inhibitors.

The structure coordinates described above may also be used to derive the dihedral angles, phi and psi, that define the conformation of the amino acids in the protein backbone. As will be understood by those skilled in the art, the phin angle refers to the rotation around the bond between the alpha-carbon and the nitrogen, and the PSin angle refers to the rotation around the bond between the carbonyl carbon and the alpha-carbon. The subscript "n" identifies the amino acid whose conformation is being described [for a general reference, see Blundell and Johnson, Protein Crystallography, Academic Press, London, 1976].

9. Uses of the Crystal and Diffraction Pattern of AIK

Crystals, crystallization conditions and the diffraction pattern of AIK that can be generated from the crystals also have a range of uses. One particular use relates to screening entities that are not known ligands of AIK for their ability to bind to AIK. For example, with the availability of crystallization conditions, crystals and diffraction patterns of AIK provided according to the present invention, it is possible to take a crystal of AIK; expose the crystal to one or more entities that may be a ligand of AIK; and determine whether a ligand/AIK complex is formed. The crystals of AIK may be exposed to potential ligands by various methods, including but not limited to, soaking a crystal in a solution of one or more potential ligands or co-crystallizing AIK in the presence of one or more potential ligands. Given the structure coordinates provided herein, once a ligand complex is formed, the structure coordinates can be used as a model in molecular replacement in order to determine the structure of the ligand complex.

Once one or more ligands are identified, structural information from the ligand/AIK complex(es) may be used to design new ligands that bind tighter, bind more specifically, have better biological activity or have better safety profile than known ligands.

In one embodiment, a method is provided for identifying a ligand that binds to AIK comprising: (a) attempting to crystallize a protein that comprises a sequence wherein at least a portion of the sequence has 55%, 65%, 75%, 85%, 90%, 95%, 97%, 99% or greater identity with SEQ. ID No. 3 in the presence of one or more entities; (b) if crystals of the protein are obtained in step (a), obtaining an X-ray diffraction pattern of the protein crystal; and (c) determining whether a ligand/protein complex was formed by comparing an X-ray diffraction pattern of a crystal of the protein formed in the absence of the one or more entities to the crystal formed in the presence of the one or more entities.

In another embodiment, a method is provided for identifying a ligand that binds to AIK comprising: soaking a crystal of a protein wherein at least a portion of the protein has 55%, 65%, 75%, 85%, 90%, 95%, 97%, 99% or greater identity with SEQ. ID No. 3 with one or more entities; determining whether a ligand/protein complex was formed by comparing an X-ray diffraction pattern of a crystal of the protein that has not been soaked with the one or more entities to the crystal that has been soaked with the one or more entities.

Optionally, the method may further comprise converting the diffraction patterns into electron density maps using phases of the protein crystal and comparing the electron density maps.

Libraries of "shape-diverse" compounds may optionally be used to allow direct identification of the ligand-receptor complex even when the ligand is exposed as part of a mixture. According to this variation, the need for time-consuming de-convolution of a hit from the mixture is avoided. More specifically, the calculated electron density function reveals the binding event, identifies the bound compound and provides a detailed 3-D structure of the ligand-receptor complex. Once a hit is found, one may optionally also screen a number of analogs or derivatives of the hit for tighter binding or better biological activity by traditional screening methods. The hit and information about the structure of the target may also be used to develop analogs or derivatives with tighter binding or better biological activity. It is noted that the ligand-AIK complex may optionally be exposed to additional iterations of potential ligands so that two or more hits can be linked together to make a more potent ligand. Screening for potential ligands by co-crystallization and/or soaking is further described in U.S. Pat. No. 6,297,021, which is incorporated herein by reference.

EXAMPLES

Example 1

Expression and Purification of AIK

This example describes the expression of AIK. It should be noted that a variety of other expression systems and hosts are also suitable for the expression of AIK, as would be readily appreciated by one of skill in the art.

The portion of the gene encoding residues 125-391 (from SEQ. ID No. 1) which correspond to the catalytic domains of human AIK was isolated from cDNA libraries (testis) by PCR and cloned into the BamH I site of pFastbacHTh (Gibco-BRL). This DNA sequence is presented in FIG. 1 as SEQ. ID No. 2.

Expression in this vector generated a fusion of the kinase domain with a cleavable (rTev) N-terminal 6×-histidine tag residues, the amino acid sequence of which is shown in FIG. 1 as SEQ. ID. 3. Recombinant baculoviruses incorporating the kinase cDNA constructs were generated by transposition using the Bac-to-Bac system (Gibco-BRL). High-titer viral stocks were generated by infection of *Spodoptera frugiperda* Sf9 cells and the expression of recombinant protein was carried out by infection of *Trichoplusia ni* Hi5 cells (Gibco-BRL) in 5 L Wave Bioreactors (Wave Biotech). Recombinant proteins were isolated from cellular extracts by passage over ProBond (InVitrogen) resin. It is noted that the polyhistidine tags may optionally be removed by treatment with rTEV protease (InVitrogen). In this instance, the polyhistidine tag was removed. The AIK protein purity as determined on denaturing SDS-PAGE gel was 90-95%. AIK was not phosphorylated during the isolation and purification procedures as confirmed by mass spectrometry. AIK was concentrated to a final concentration of 9.4 mg/ml and stored at 4° C. in a buffer containing 50 mM TRIS-HCl pH 7.6, 250 mM NaCl, 1 mM EDTA and 1 mM DTT.

Example 2

Crystallization of AIK-ATPγS Complex

This example describes the crystallization of AIK-ATPγS complex. It is noted that the precise crystallization conditions used may be further varied, for example by performing a fine screen based on these crystallization conditions.

AIK protein samples were incubated with 2 mM ATPγS and 4 mM $MgCl_2$ before setting crystallization trials. Crystals were obtained after an extensive and broad screen of conditions, followed by optimization. Table 2 summarizes effective crystallization conditions that were identified.

Diffraction quality crystals were grown as in 100 nL sitting droplets using the vapor diffusion method. 50 nL comprising the AIK-ATPγS complex (9.4 mg/ml) was mixed with 50 nL from a reservoir solution (100 μL) comprising 0.1M Bicine pH-9.0, 20% PEG MME 550 and 0.1M NaCl. The resulting solution was incubated over a period of one week at 20° C.

Crystals typically appeared after 8-24 hours and grew to a maximum size within 48 hours. Single crystals were separated from their parent cluster and transferred, briefly, into a cryoprotecting solution containing the reservoir solution supplemented with 20% v/v ethylene glycol. Crystals were then flash frozen by immersion in liquid nitrogen and then stored under liquid nitrogen. A crystal of AIK-ATPγS complex produced as described is illustrated in FIG. 2.

While the present invention is disclosed with reference to certain embodiments and examples detailed above, it is to be understood that these embodiments and examples are intended to be illustrative rather than limiting, as it is contemplated that modifications will readily occur to those skilled in the art, which modifications are intended to be within the scope of the invention and the appended claims. All patents, papers, and books cited in this application are incorporated herein in their entirety.

We claim:

1. A composition comprising a protein in crystalline form wherein the protein consists of residues 24-295 of SEQ ID NO: 3, wherein said protein is in complex with a ligand that is bound to the ATP binding site of the protein, and wherein the protein crystal has a crystal lattice in a P6$_1$22 space group and unit cell dimensions, +/−2%, of a=80.45 Å, b=80.45 Å and c=172.18 Å.

2. The composition according to claim 1 wherein the protein crystal diffracts X-rays for a determination of structure coordinates to a resolution of a value equal to or less than 3.0 Angstroms.

3. A method for forming a crystal of a protein comprising:
   forming a crystallization volume comprising a precipitant solution and a protein that consists of residues 24-295 of SEQ ID NO:3;
   storing the crystallization volume under conditions suitable for crystal formation of the protein; and
   forming a protein crystal, wherein said protein is in complex with an ATP binding site ligand and wherein the protein crystal has a crystal lattice in a P6$_1$22 space group and unit cell dimensions, +/−2%, of a=80.45 Å, b=80.45 Å and c=172.18 Å.

4. The method according to claim 3 wherein the formed protein crystal diffracts X-rays for a determination of structure coordinates to a resolution of a value equal to or less than 3.0 Angstroms.

5. The method according to claim 3, wherein a protein crystal is formed, the method further comprising diffracting the protein crystal to produce a diffraction pattern and solving the structure of the protein from the diffraction pattern.

6. The method according to claim 5, the method further comprising:

performing rational drug design using the solved structure; and identifying an entity that potentially associates with the protein.

7. The method according to claim 6 further comprising selecting one or more entities based on the rational drug design and contacting the selected entities with the protein.

8. The method according to claim 7 further comprising measuring an activity of the protein when contacted with the one or more entities.

9. A noncrystalline protein consisting of SEQ ID NO:3.

10. A non-crystalline protein consisting of residues 24-295 of SEQ ID NO:3.

11. An isolated noncrystalline protein consisting of residues 24-295 of SEQ ID NO:3.

12. An isolated noncrystalline protein consisting of SEQ ID NO:3.

* * * * *